United States Patent
Fessler et al.

(10) Patent No.: US 12,310,641 B2
(45) Date of Patent: May 27, 2025

(54) BONE FIXATION SYSTEM AND METHODS OF USE

(71) Applicant: DUET SPINE HOLDINGS, LLC, Winona Lake, IN (US)

(72) Inventors: Richard G. Fessler, Lake Forest, IL (US); Jon C. Serbousek, Winona Lake, IN (US); Jeffrey Nycz, Warsaw, IN (US); Jill A. Serbousek, Winona Lake, IN (US)

(73) Assignee: DUET SPINE HOLDINGS, LLC, Winona Lake, IN (US)

( * ) Notice: Subject to any disclaimer, the term of this patent is extended or adjusted under 35 U.S.C. 154(b) by 0 days.

(21) Appl. No.: 18/166,967

(22) Filed: Feb. 9, 2023

(65) Prior Publication Data

US 2023/0181229 A1 Jun. 15, 2023

Related U.S. Application Data

(63) Continuation of application No. 17/748,816, filed on May 19, 2022, now Pat. No. 11,576,709, which is a
(Continued)

(51) Int. Cl.
*A61B 17/86* (2006.01)
*A61B 17/70* (2006.01)

(52) U.S. Cl.
CPC ...... *A61B 17/8605* (2013.01); *A61B 17/7001* (2013.01); *A61B 17/7052* (2013.01); *A61B 17/8625* (2013.01); *A61B 17/864* (2013.01)

(58) Field of Classification Search
CPC .................. A61B 17/7034; A61B 17/8605
See application file for complete search history.

(56) References Cited

U.S. PATENT DOCUMENTS

| | | |
|---|---|---|
| 6,048,343 A | 4/2000 | Mathis |
| 7,326,248 B2 | 2/2008 | Michelson |

(Continued)

FOREIGN PATENT DOCUMENTS

| | | |
|---|---|---|
| CN | 102751945 | 10/2012 |
| JP | 2001252283 | 9/2001 |

(Continued)

OTHER PUBLICATIONS

Examination Report received in Australian Application No. 2019418411, dated Jul. 4, 2022, 5 pages.

(Continued)

*Primary Examiner* — Olivia C Chang
(74) *Attorney, Agent, or Firm* — Heslin Rothenberg Farley & Mesiti P.C.; Jacquelyn A. Graff, Esq.

(57) ABSTRACT

A bone fixation system comprises a first fastener configured to anchor into a first vertebrae, a second fastener configured to anchor into a second vertebrae, and a set screw to retain the second fastener to the first fastener. The first fastener includes a shaft extending along a longitudinal axis and a head. The shaft includes a first cylindrical body. The head of the first fastener includes a second cylindrical body defining a passageway having an interior surface. The passageway defines a longitudinal axis that is different than the longitudinal axis of the shaft. The first cylindrical body of the shaft and the second cylindrical body of the head are angled relative to each other. A head of the second fastener is configured to engage the interior surface of the passageway of the head of the first fastener. The set screw retains the head of the second fastener in the passageway.

20 Claims, 78 Drawing Sheets

Related U.S. Application Data continuation of application No. 17/359,210, filed on Jun. 25, 2021, now Pat. No. 11,344,349, which is a continuation of application No. PCT/US2019/067149, filed on Dec. 18, 2019.

(60) Provisional application No. 62/787,571, filed on Jan. 2, 2019.

(56) References Cited

U.S. PATENT DOCUMENTS

| | | |
|---|---|---|
| 8,123,810 B2 | 2/2012 | Gordon |
| 8,303,589 B2 | 11/2012 | Tyber |
| 8,328,806 B2 | 12/2012 | Tyber |
| 8,343,199 B2 | 1/2013 | Tyber |
| 8,480,716 B2 | 7/2013 | Perrow |
| 9,017,329 B2 | 4/2015 | Tyber |
| 9,044,272 B2 | 6/2015 | Shaffrey |
| 9,044,282 B2 | 6/2015 | Tyber |
| 9,060,808 B2 | 6/2015 | Overes |
| 9,084,646 B2 | 7/2015 | Gordon |
| 9,149,316 B2 | 10/2015 | Appenzeller |
| 9,364,271 B2 | 6/2016 | Tyber |
| 9,589,220 B2 | 3/2017 | Nissen |
| 9,636,154 B2 | 5/2017 | Overes |
| 9,649,133 B2 | 5/2017 | Strnad |
| 9,877,752 B2 | 1/2018 | Tyber |
| 9,913,674 B2 | 3/2018 | Tyber |
| 9,918,763 B2 | 3/2018 | Hynes |
| 10,045,804 B2 | 8/2018 | Sevrain |
| 10,517,644 B2 | 12/2019 | Fessler |
| D912,821 S | 3/2021 | Serbousek |
| 2005/0059973 A1* | 3/2005 | Dierks ............... A61B 17/7041 606/278 |
| 2006/0189991 A1 | 8/2006 | Bickley |
| 2007/0055249 A1 | 3/2007 | Jensen |
| 2009/0118772 A1 | 5/2009 | Diederich |
| 2010/0145397 A1 | 6/2010 | Overes |
| 2011/0184470 A1 | 7/2011 | Gorek |
| 2011/0230920 A1 | 9/2011 | Gorek |
| 2011/0282398 A1* | 11/2011 | Overes ............... A61B 17/8877 606/310 |
| 2014/0058457 A1 | 2/2014 | Appenzeller |
| 2016/0128732 A1 | 5/2016 | Strnad |
| 2017/0189071 A1 | 7/2017 | Fessler |
| 2018/0250034 A1 | 9/2018 | Fessler |
| 2019/0029744 A1 | 1/2019 | Cundiff |
| 2019/0336189 A1 | 11/2019 | Cundiff |

FOREIGN PATENT DOCUMENTS

| | | |
|---|---|---|
| WO | 9848717 | 11/1998 |
| WO | 2011155931 | 12/2011 |
| WO | 2016044845 | 3/2016 |

OTHER PUBLICATIONS

International Search Report and Written Opinion received in Patent Cooperation Treaty Application No. PCT/US2019/067149, dated Mar. 5, 2020.

* cited by examiner

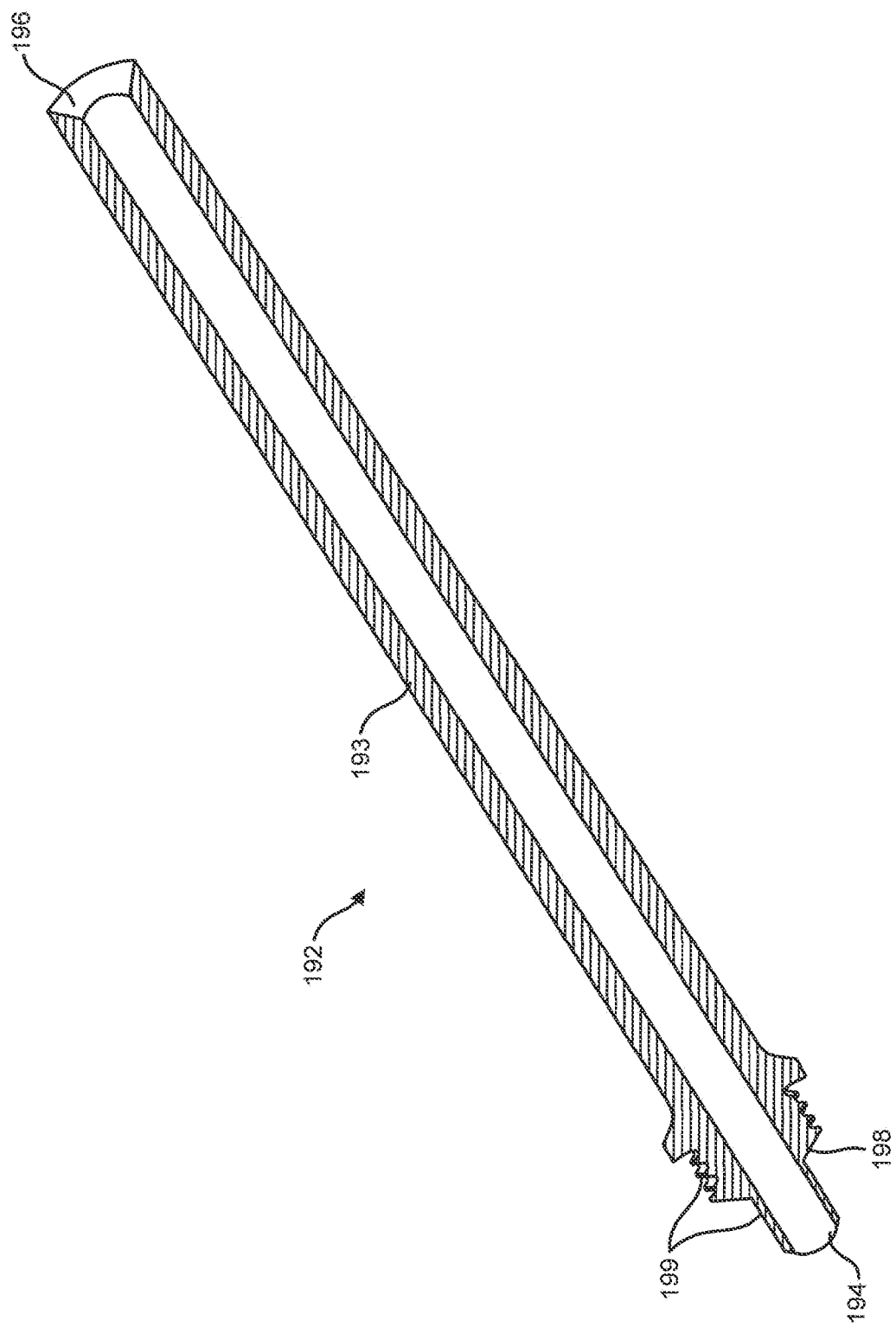

BONE FIXATION SYSTEM AND METHODS OF USE

PRIORITY STATEMENT AND CROSS-REFERENCE TO RELATED APPLICATIONS

This application is a continuation application of U.S. application Ser. No. 17/748,816, filed May 19, 2022, which is a continuation application of U.S. application Ser. No. 17/359,210, filed May 31, 2022, which is continuation application claiming priority to co-pending international application PCT/US2019/067149, which designates the United States, in the names of Richard G. Fessler et al. entitled "Bone Fixation System and Methods of Use;" and filed on Dec. 18, 2019; which claims priority from and the benefit of the filing date of U.S. Patent Application Ser. No. 62/787,571 in the names of Richard Fessler et al entitled "Bone Fixation System and Methods of Use" and filed on Jan. 2, 2019, both of which are hereby incorporated by reference, in entirety, for all purposes.

FIELD OF INVENTION

The present invention relates generally to general surgery, orthopedic and neurosurgical implants used for insertion within a patient's vertebrae. More specifically, but not exclusively, the present invention concerns bone fixation systems for implantation into a patient's spine to maintain or re-establish proper spacing and alignment of the spine.

BACKGROUND OF THE INVENTION

Spinal deformities may result from disease, age or trauma causing destabilization of the spine. To correct destabilization of a patient's spine, posterior fusion device systems may be used. The posterior fusion device systems that are currently available are designed to be applicable to single and multiple level stabilizations using a rod extending between adjacent bone screws for strength. These posterior fusion device systems and the instrumentation used for insertion into a patient's spine are extensive, complicated and expensive and susceptible to loosening of the rods and screws.

SUMMARY OF THE INVENTION

Aspects of the present invention provide bone fixation systems, including at a single level or multiple levels, and methods that can maintain or re-establish anatomic spacing within a patient's spine.

According to one aspect of the present invention, provided herein is a bone fixation system, including a first or primary fastener, a second or secondary fastener, and a set screw. The first fastener includes a shaft and an enlarged head. The enlarged head extends from and is angled relative to the shaft. The shaft including a first longitudinal axis. A portion of the shaft of the first fastener is configured to anchor into bone. The enlarged head of the first fastener includes a passageway having an interior surface. The passageway defines a second longitudinal axis that is dangled with respect to the first longitudinal axis of the shaft. The passageway includes a first end and a second end. The interior surface of the passageway defining a seat. The second fastener includes a shaft extending along a third longitudinal axis and a head. A portion of the shaft of the second fastener is configured to anchor into bone. The head of the second fastener is configured to engage the seat of the first fastener. The engagement of the seat and the head allows for a plurality of angular relationships between the second longitudinal axis relative to the third longitudinal axis. At least a portion of the set screw configured to secure within the passageway of the first fastener. The set screw including a bottom surface that contacts and retains the head of the second fastener against the seat.

In another aspect, the head of the first fastener and a portion of the second fastener are adapted for residing outside bone.

These and other objects, features and advantages of this invention will become apparent from the following detailed description of the various aspects and principles of the invention taken in conjunction with the accompanying drawings.

BRIEF DESCRIPTION OF THE DRAWINGS

The accompanying drawings, which are incorporated in and constitute a part of the specification, illustrate embodiments of the invention and, together with the detailed description herein, serve to explain the principles of the invention. The drawings are only for purposes of illustrating examples and are not to be construed as limiting the invention. It is emphasized that, in accordance with the standard practice in the industry, various features are not drawn to scale. In fact, the dimensions of the various features may be arbitrarily increased or reduced for clarity of discussion.

FIG. 8B illustrates a cross-sectional view of the drill guide of FIG. 8A, in accordance with one or more aspects of the present invention;

DETAILED DESCRIPTION FOR CARRYING OUT THE INVENTION

Figure 1:
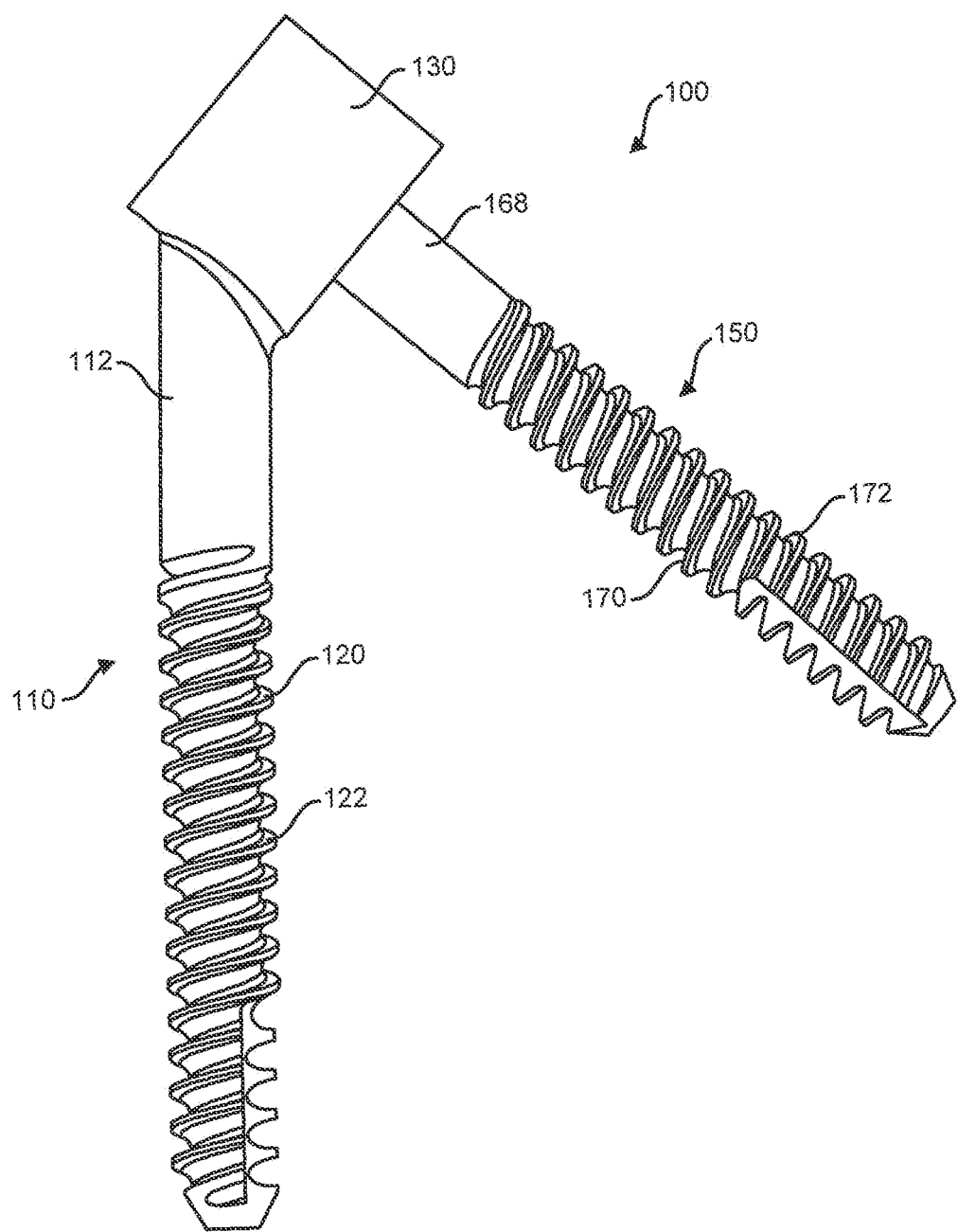
FIG. 1 illustrates a side view of one embodiment of a bone fixation system, in accordance with one or more aspects of the present invention.
Figure 2:
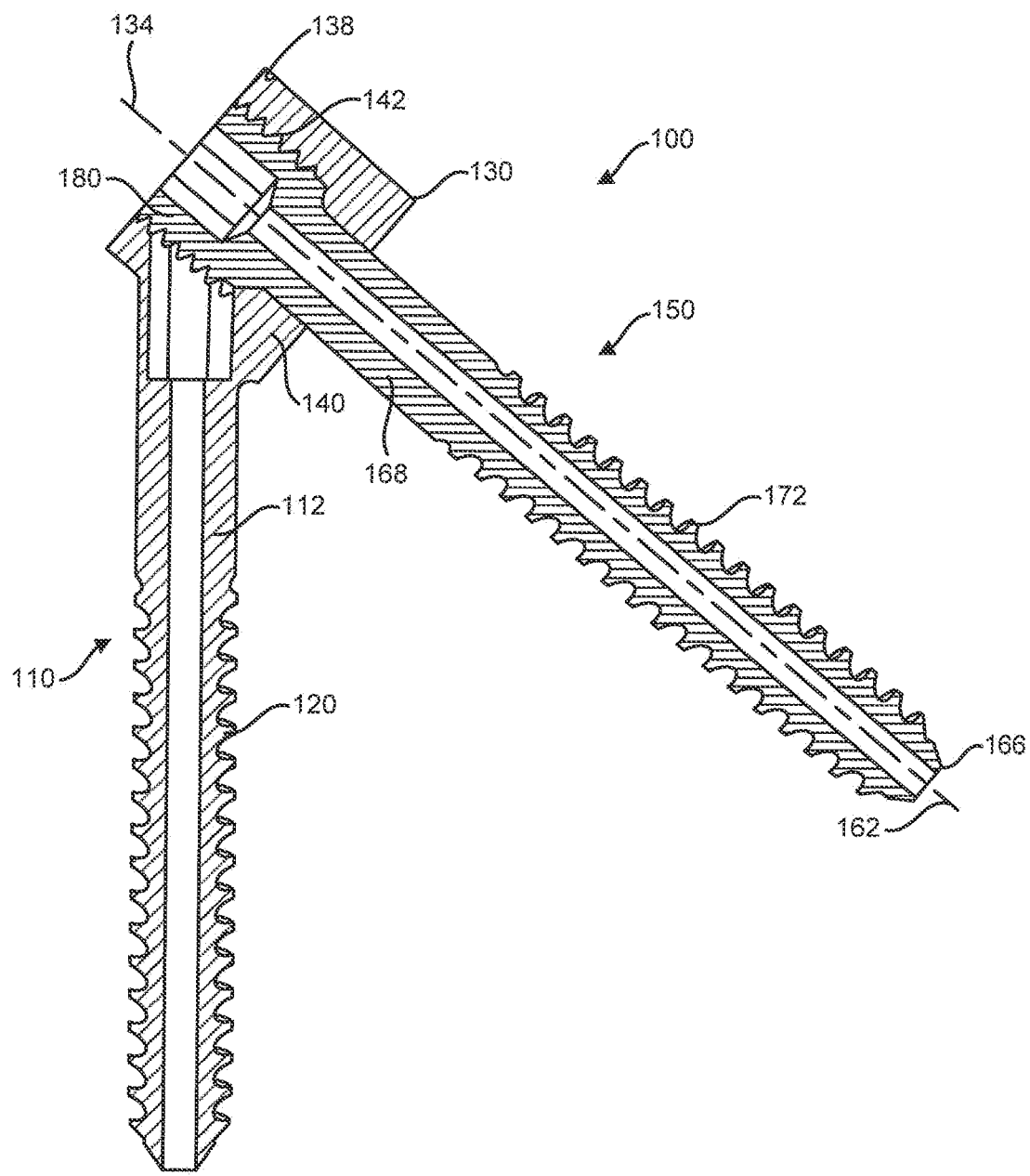
FIG. 2 illustrates a cross-sectional view of the bone fixation system of FIG. 1, in accordance with one or more aspects of the present invention.
Figure 3:
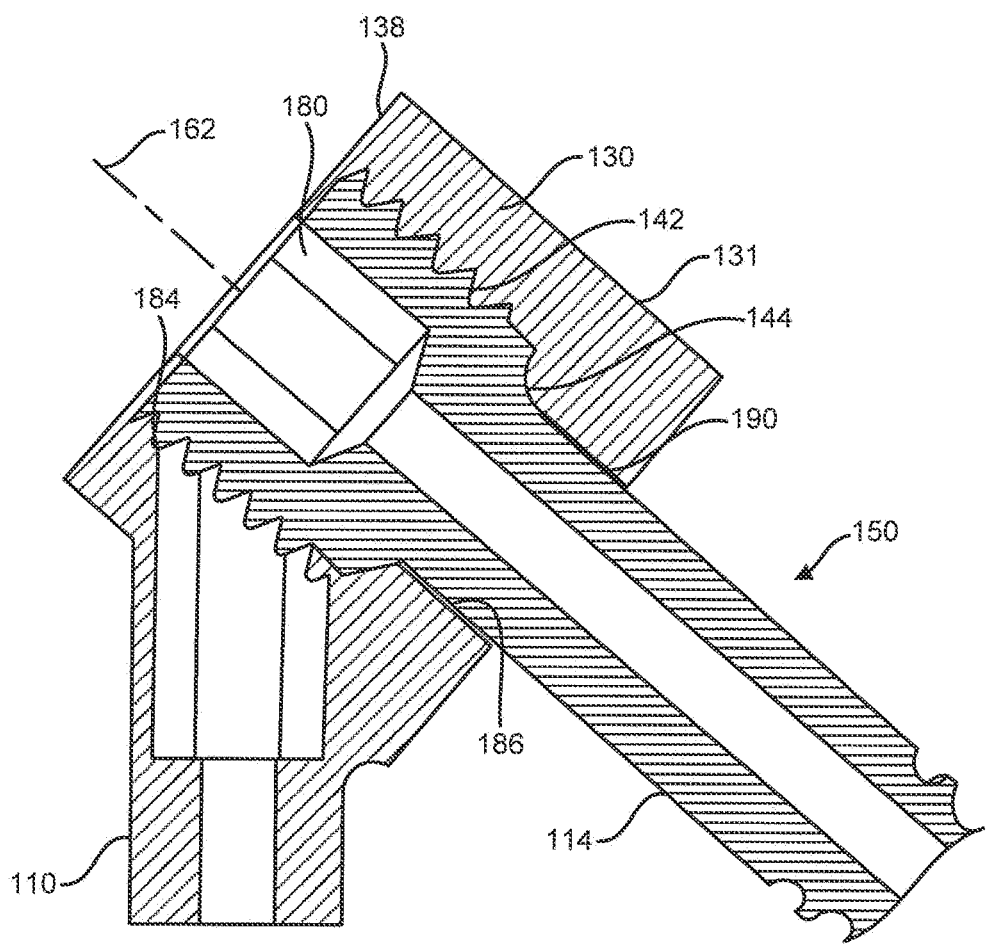
FIG. 3 illustrates a partial cross-sectional view of the bone fixation system of FIG. 1, in accordance with one or more aspects of the present invention.

Generally stated, disclosed herein are different embodiments and examples of a bone fixation system. The embodiments and examples described herein of a bone fixation system constructed in accordance with one or more aspects of the present invention avoid the need for using a rod to connect adjacent pedicle screws typically used in back surgery. Without use of a connecting rod, there are less parts involved and less movable parts and less chance of movement of the fusion system or loosening of its components after surgery with a bone fixation system constructed in accordance with one or more principles or aspects of the present invention. A bone fixation system constructed in accordance with one or more principles or aspects of the present invention also does not rely on a connecting rod for strength. Further, surgical methods for inserting the bone fixation systems are discussed.

In this detailed description and the following claims, the words proximal, distal, anterior, posterior, medial, lateral, superior, inferior, cephalad and caudally are defined by their standard usage for indicating a particular part of a bone or implant according to the relative disposition of the natural bone or directional terms of reference. For example, "proximal" means the portion of an implant nearest the insertion instrument, while "distal" indicates the portion of the implant farthest from the insertion instrument. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure, "cephalad" means a direction toward the head and "caudally" means a direction toward the inferior part of the body.

In general, the embodiments and examples described herein of a bone fixation system constructed in accordance with one or more principles or aspects of the present invention include a primary screw or fastener and a secondary screw or fastener. The primary fastener or fastener includes a shaft and a head angled relative to the shaft. In one example, the secondary fastener is directly coupled to the primary fastener by, for example, mating threads or an interference fit. In alternative embodiments, a set screw is used to retain the second fastener within the head of the primary fastener. In other examples, the head of the primary fastener provides a seat for the second fastener to enable variable angulations of the secondary fastener relative to the primary fastener.

In general, the head of the primary fastener is shaped and angled relative to the shaft to enable insertion of the secondary fastener through it and into an adjacent pedicle, thereby eliminating the need for a rod or plate. The shape of the head of the primary fastener provides a low profile and less trauma to soft tissues when inserted, for example, via minimally invasive techniques. In one example, the head of the primary fastener is enlarged with respect to the shaft of the primary fastener. For example, the cross-sectional width of the enlarged head, taken normal to the longitudinal axis of the head, is greater than the cross-sectional width of the shaft, taken normal to the longitudinal axis of the shaft. The head may include a body (e.g. cylindrical) that is angled relative to the shaft of the primary fastener. The position of the head of the primary fastener ensures closest proximity of the head to bone, thereby maximizing strength of the system. The angulation of the head relative to the shaft of the primary fastener enables appropriate direction of the secondary fastener to engage a second vertebra or pedicle, thus eliminating the need for a rod or plate. By minimizing the number of parts, the risk of failure through, for example, loosening of set screws to tulip heads in conventional bone fixation systems is reduced.

In general, the head of the primary fastener and a portion of the second fastener are configured to reside outside bone to allow for trajectory of the secondary fastener to engage adjacent pedicle or use at multiple adjacent vertebrae levels. The head of the primary fastener is incorporated partially into the longitudinal axis of the shaft of the primary fastener to minimize the overall size of the head, thereby decreasing soft tissue trauma on insertion and long-term irritation of adjacent muscle. The angulated head of the primary fastener enables, for example, in line insertion of a primary fastener screwdriver, and insertion of a secondary fastener and screwdriver through the same external entrance of the primary fastener during insertion.

The bone fixation system described herein may also include a tapering or a gradually increasing thickness of the shaft of the primary fastener as it approaches the head. This tapering or increased thickness at a region of greatest stress on the primary fastener reduces failure through fracture of the primary fastener and enhances the fastener to bone interface thereby providing enhanced stability by increasing compressive load.

The combination of the primary fastener and secondary fastener described by the examples herein enables insertion of the bone fixation system via either an MIS or OPEN technique without the need for additional instrumentation. The system design relies on angulation of two fasteners relative to each other for stability and minimizes the need for additional instrumentation or components, such as, for example, rods and multiple screw lengths and thicknesses. The design of the bone fixation system described herein combines the resistance to "pull out" imparted by the threads of the fasteners with that created by the angulation of the fasteners relative to each other, thereby making pull out virtually impossible.

Referring to the drawings, wherein like reference numerals are used to indicate like or analogous components throughout the several views, and with particular reference to FIGS. 1-8E, there is illustrated an exemplary embodiment of a bone fixation system 100. The bone fixation system 100 may include a first or primary fastener 110 for anchoring into, for example, a first bone or vertebrae and a second or secondary fastener 150 for anchoring into, for example, a second bone or vertebrae.

With continued reference to FIGS. 4A-4E, first fastener 110 may include a shaft 120, a head 130, and a longitudinal axis 121. Shaft 120 may include a neck 112 connecting shaft 120 to the head 130 and one or more bone engagement mechanisms 122 to facilitate a gripping engagement of first fastener 110 to bone. Shaft 120 also includes an outer surface 114. In one embodiment, outer surface 114 may taper radially outward from longitudinal axis 112 in the portion of neck 112 proximate head 130.

Figure 4A:
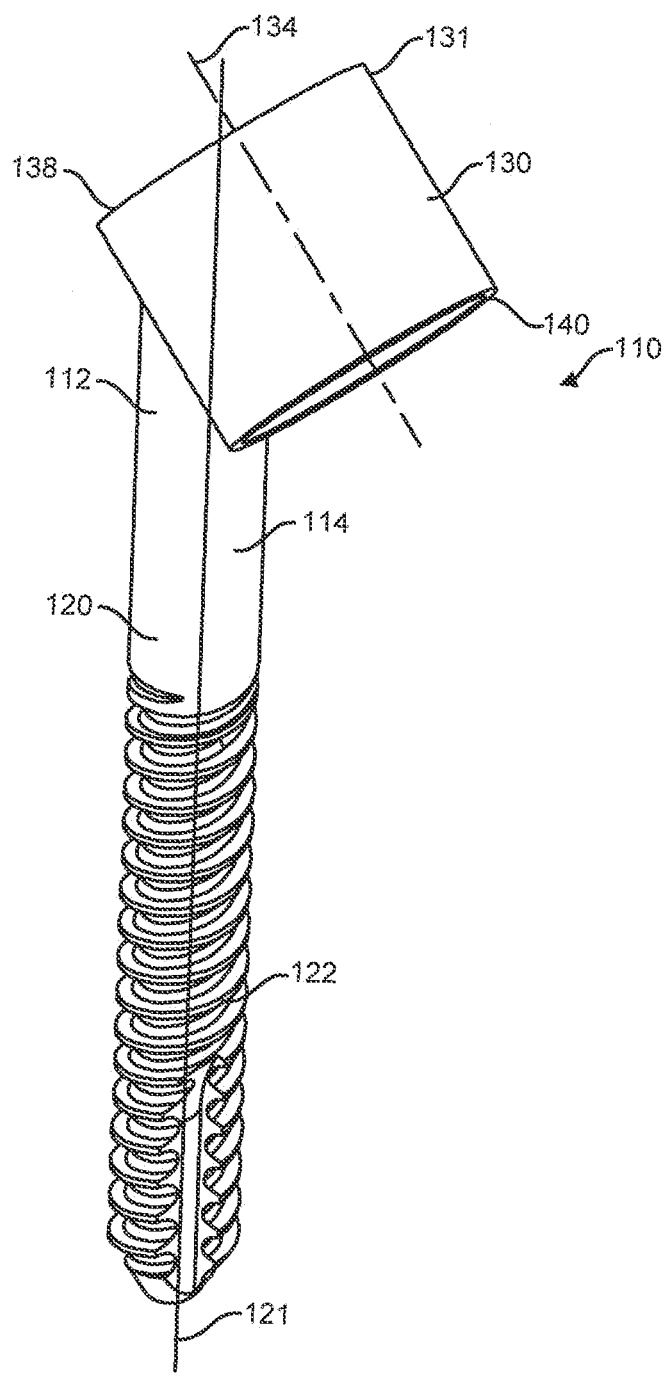
FIG. 4A illustrates a prospective view of one embodiment of a first fastener of the bone fixation system of FIG. 1, in accordance with one or more aspects of the present invention.

In one example illustrated in FIG. 4A, shaft 120 may be, for example, threaded along its entire length, threaded along only a portion of the length, or non-threaded. In the illustrated embodiment, the external thread, for example, is a single lead thread that extends from a distal tip of the shaft to the proximal head portion. Other suitable bone engagement mechanisms may include, but are not limited to, one or more annular ridges, multiple threads, dual lead threads, variable pitched threads, longitudinal splines or other geometries, and/or any conventional bone engagement mechanism.

As shown in FIGS. 4A-4E, head 130 includes a cylindrical body 131. In one embodiment, the diameter of cylindrical body 131 is greater than the diameter of shaft 120, when measured normal to their respective longitudinal axes. When connected to neck 112, head 130 appears like a halo over shaft 120. Head 130 may form a receiving portion, such as, for example, a passageway 132 having a longitudinal axis 134. Passageway 132 may be in the form of, for example, a through hole or, alternatively, a slot formed between two arms. Passageway 132 defines an interior cavity or space having an inner surface 136 extending from a first end 138 to a second end 140. In one embodiment, first end 138 and second end 140 extend beyond the outer surface 114 of shaft 120. Passageway 132 may be sized and configured to receive and allow pass through of at least a portion of second fastener 150 or other spinal connection element for anchoring the system 100 to, for example, a second bone or vertebrae. Passageway 132 may also be sized and configured to retain or secure at least a portion of head 180 of second fastener 150.

Figure 4B:
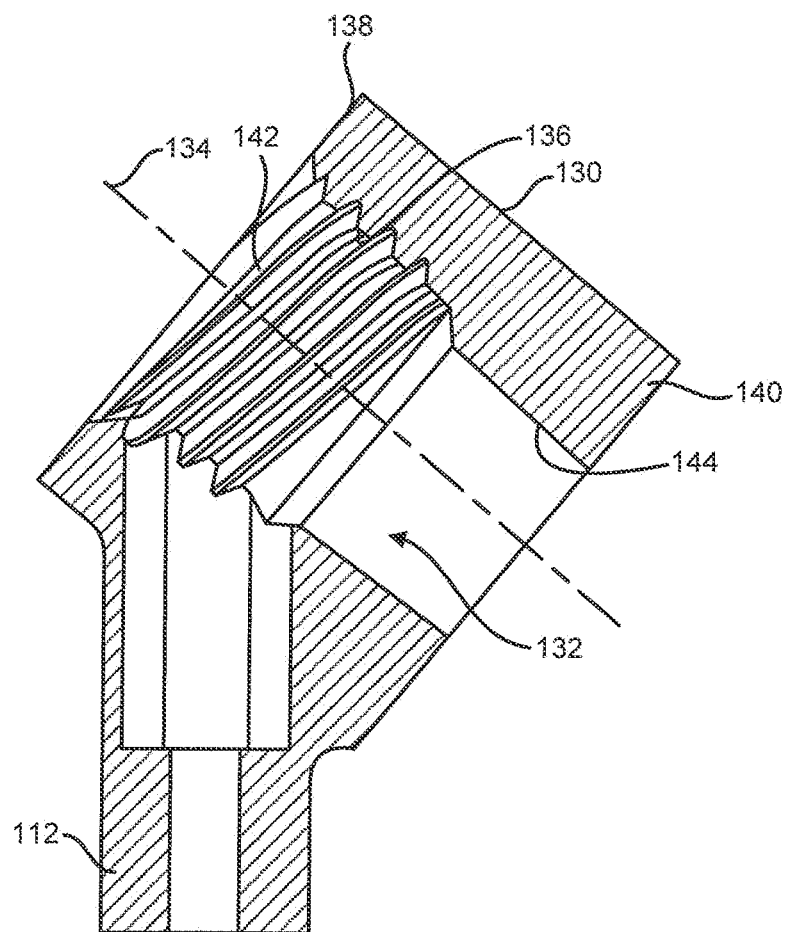
FIG. 4B illustrates a partial cross-sectional view of the first fastener of FIG. 4A, in accordance with one or more aspects of the present invention.
Figure 4C:
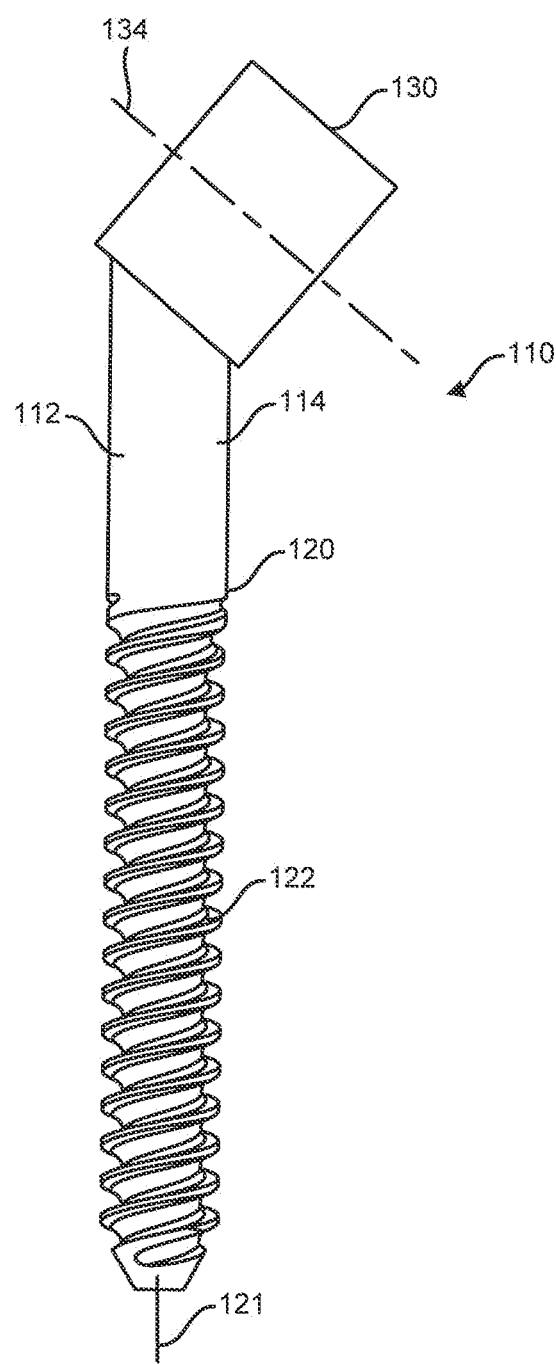
FIG. 4C illustrates a side view of the first fastener of FIG. 4A, in accordance with one or more aspects of the present invention.
Figure 4D:
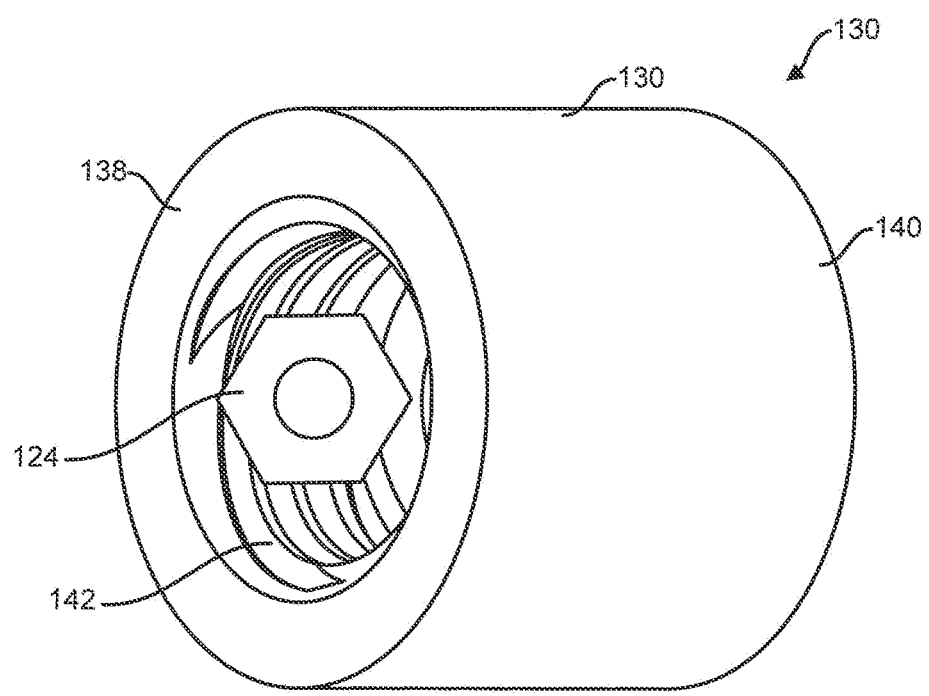
FIG. 4D illustrates a top view of the first fastener of FIG. 4A, in accordance with one or more aspects of the present invention.
Figure 4E:
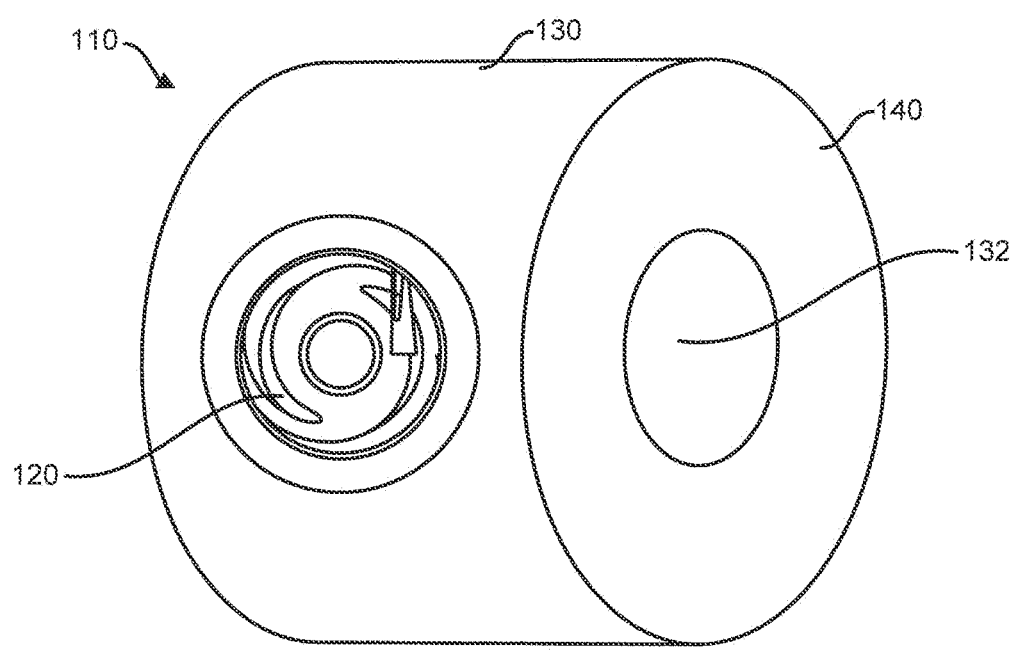
FIG. 4E illustrates a bottom view of the first fastener of FIG. 4A, in accordance with one or more aspects of the present invention.

In one embodiment illustrated in FIG. 4B, interior surface 136 of passageway 132 may include, for example, a threaded portion 142 that extends along at least a portion of interior surface 136 from first end 138. Passageway 132 may also include a seat 144 that may extend along at least another portion of interior surface 136 towards second end 140. In one example, seat 144 may be formed by interior surface 136 tapering inward towards longitudinal axis 134 as it approaches second end 140. A tool engagement opening 124 (see FIG. 4D) may be formed within passageway 132 and extending into neck 114 of shaft 120 for engagement with, for example, a screwdriver for inserting first fastener 110 into the bone. Tool engagement opening 124 may align with a cannulated bore extending through first fastener 110.

As illustrated in FIGS. 5A-5E, second fastener 150 may include a longitudinal axis 162, a proximal end 164, a distal end 166, a shaft 170, a head 180 and a neck 168 connecting shaft 170 to head 180. Shaft 170 may include one or more bone engagement mechanisms 172 to facilitate a gripping engagement of second fastener to bone. Shaft 170 may be, for example, threaded along its entire length, threaded along only a portion of the length, or non-threaded. In the illustrated embodiment, the external thread is a single lead thread that extend from a distal tip of the shaft to the proximal head portion. Other suitable bone engagement mechanisms may include, but are not limited to, one or more annular ridges, multiple threads, dual lead threads, variable pitched threads, longitudinal splines or other geometries, and/or any conventional bone engagement mechanism.

Figure 5A:
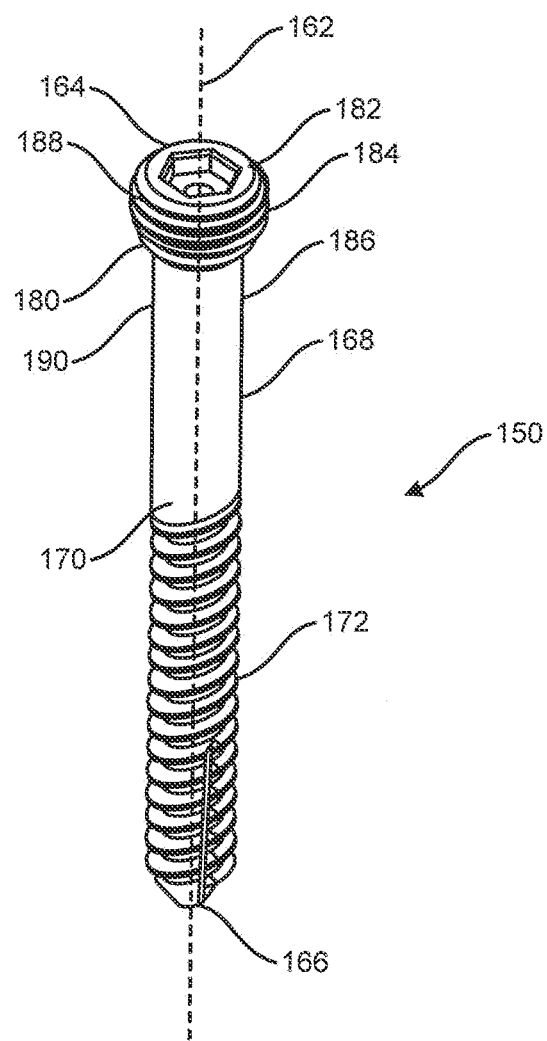
FIG. 5A illustrates a perspective view of one embodiment of a second fastener of the bone fixation system of FIG. 1, in accordance with one or more aspects of the present invention.
Figure 5B:
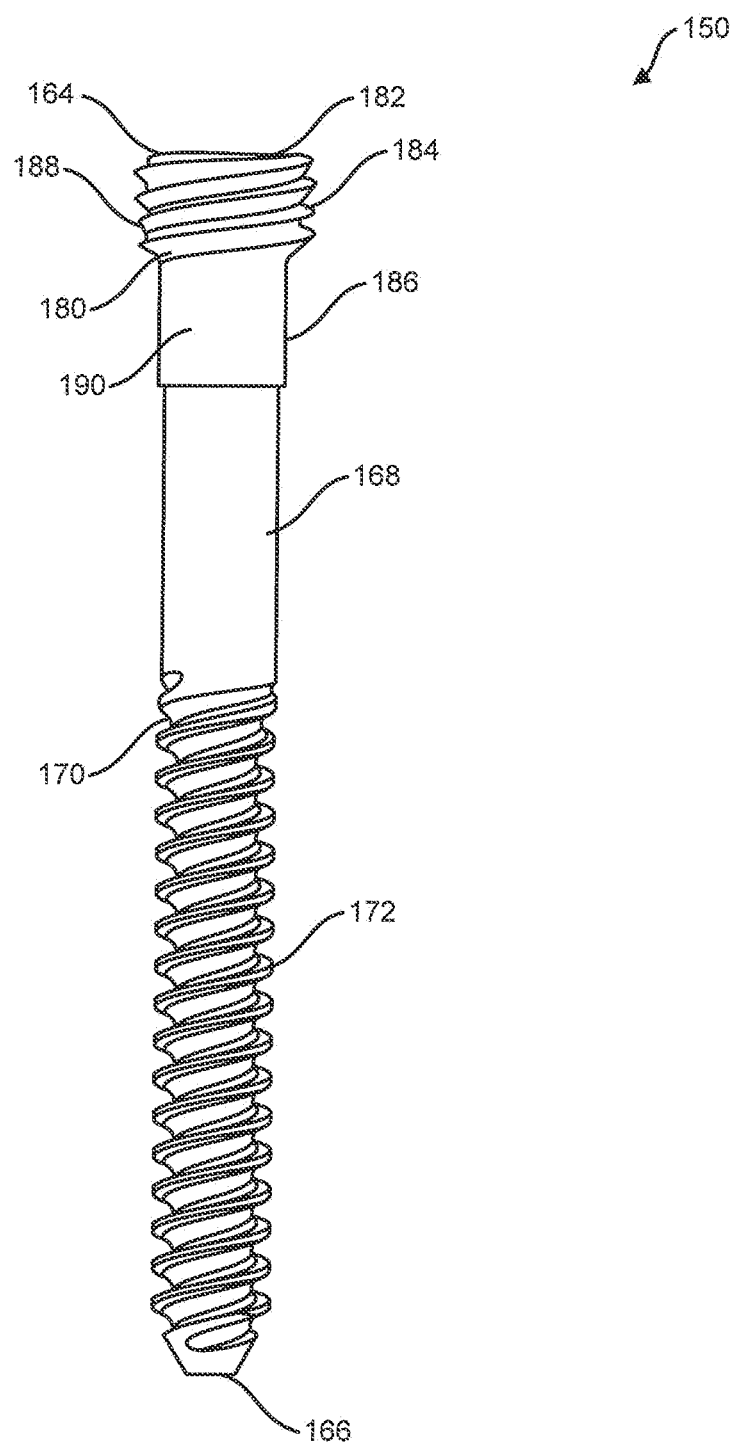
FIG. 5B illustrates a side view of the second fastener of FIG. 5A, in accordance with one or more aspects of the present invention.
Figure 5C:
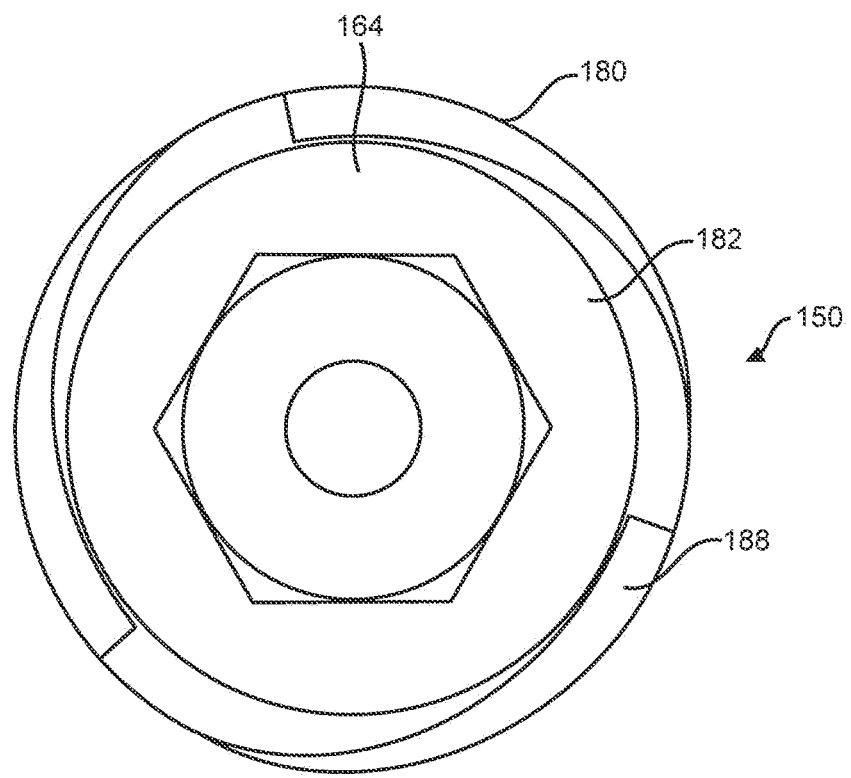
FIG. 5C illustrates a top view of the second fastener of FIG. 5A, in accordance with one or more aspects of the present invention.
Figure 5D:
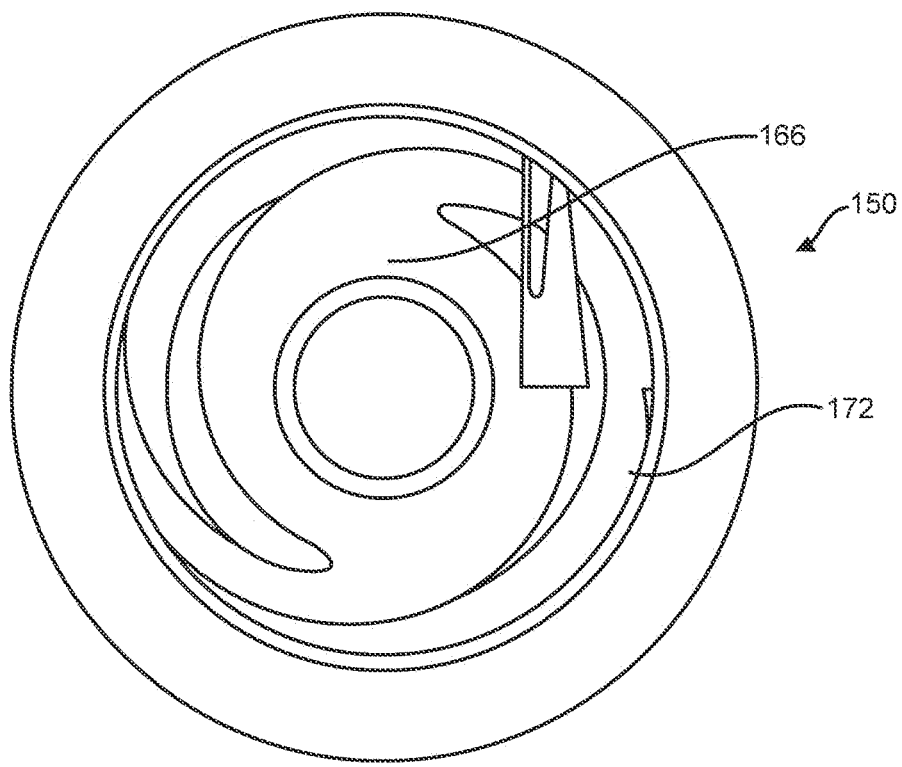
FIG. 5D illustrates a bottom view of the second fastener of FIG. 5A, in accordance with one or more aspects of the present invention.
Figure 5E:
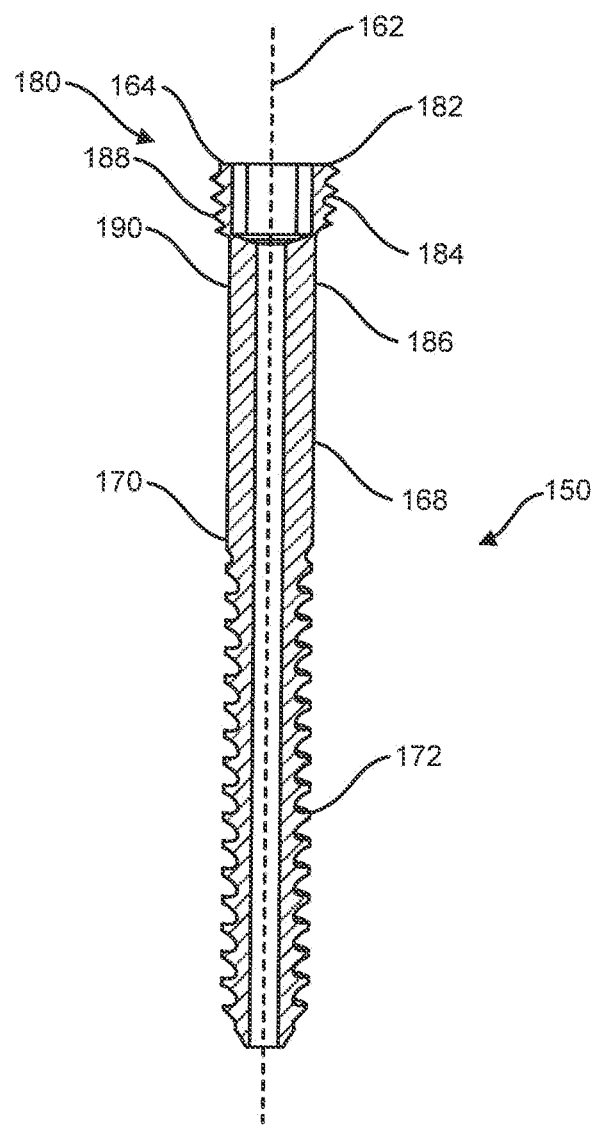
FIG. 5E illustrates a cross-sectional view of the second fastener of FIG. 5A, in accordance with one or more aspects of the present invention.
Figure 6:
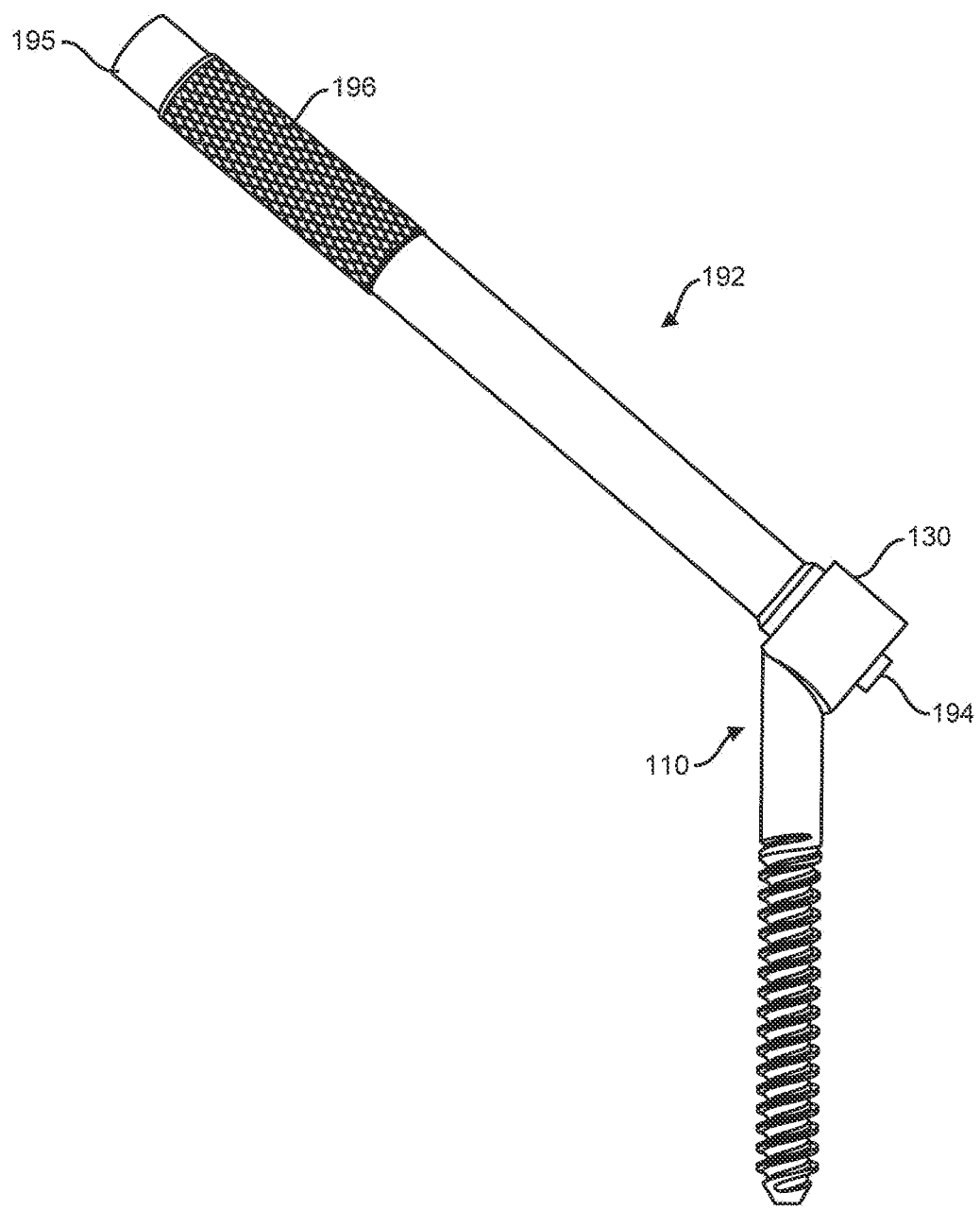
FIG. 6 illustrates a prospective view of one embodiment of a drill guide for use with the bone fixation system of FIG. 1, in accordance with one or more aspects of the present invention.

As shown in FIGS. 5A, 5C and 5E, head 180 may include a top surface 182, a first side portion 184 and a second side portion 186. Top surface 182 may include a tool engagement opening extending into head 180. First side portion 184 may include external threads 188 extending along at least a portion of the exterior surface of first side portion 184 from proximal end 164. External threads 188 are configured to engage threaded portion 142 of interior surface 136 of passageway 132 of first fastener 110. In one example illustrated in FIGS. 3 and 5E, second side portion 186 of head 180 may include an exterior surface 190 that tapers inward towards longitudinal axis. The tapered exterior surface 190 is configured to engage and mate with seat 144 of passageway 132 and allow first fastener 110 to direct second fastener 150 seamlessly through passageway 132, while also preventing second fastener 150 from migrating entirely through passageway 132 of first fastener 110.

The system 100 may be implanted by first preparing a patient's vertebrae for insertion of the bone fixation system 100. In one example, the preparation may be done using minimally invasive procedures. Next, a surgeon obtains a first fastener 110 and a second fastener 150. First fastener 110 is anchored or inserted into a desired bone such as, for example, a first vertebrae. In one example, a surgeon drives first fastener 110 into the first vertebrae using a screw driver engaged with tool engagement opening 124. Next, second fastener 150 is inserted through passageway 132 and anchored into another desired bone, such as, for example, a second or adjacent vertebrae. Second fastener 150 is inserted into passageway 132 until threads 188 of first side portion 184 mate or engage threaded portion 142 on surface 136 in passageway 132 of first fastener 110. In securing second fastener 150 to first fastener 110, second fastener 150 is screwed into head 130 until tapered exterior surface 190 of second fastener 150 engages seat 144 in passageway 132 of first fastener 110. In the system 100 illustrated in FIGS. 1-8E, second fastener 150 is orientated in a fixed angled relationship relative to first fastener 110. This fixed angle is created by engagement of threads 188 of first side portion 184 and tapered surface 190 of second side portion threads 142 of head 180 of second fastener 150 with threaded portion 142 and seat 144 of passageway 132 of head 130 of first fastener 110. When properly installed, the entire head 130 and a portion of shaft 120 of first fastener 110 and/or shaft 170 of second fastener 150 are positioned and reside outside the bone(s) in which first fastener 110 and second fastener 150 are inserted. By positioning head 130 outside the vertebrae, bone fixation system 100 is configured to aid in the fusion of multi-levels of vertebrae.

Figure 7:
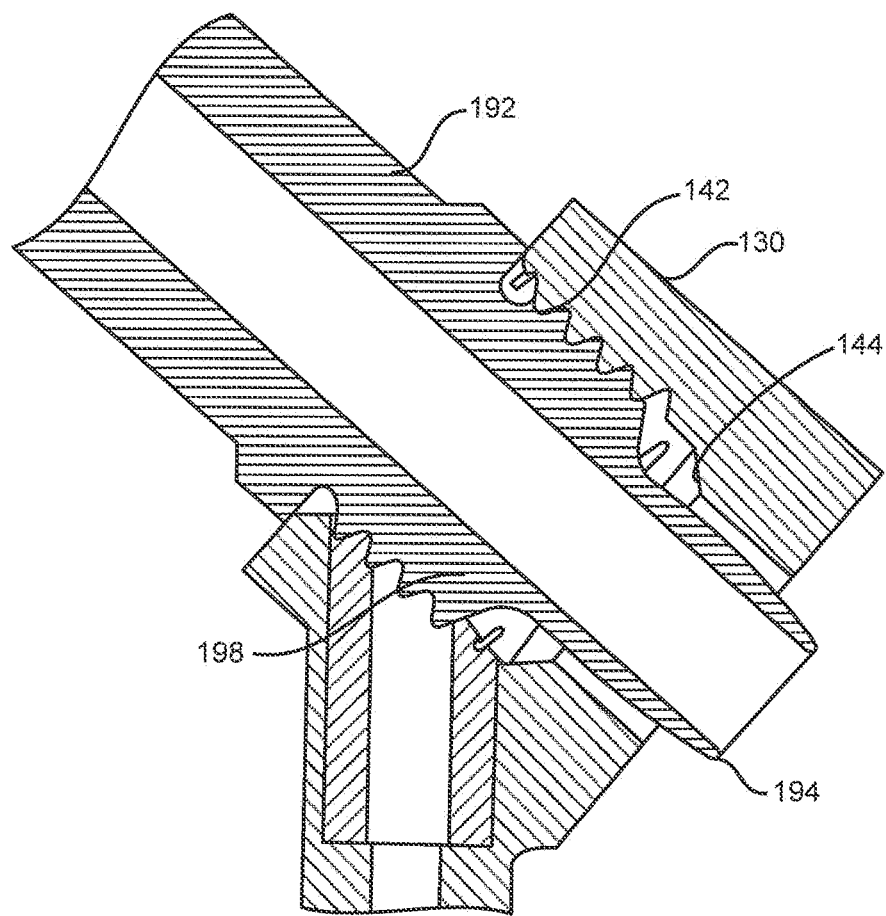
FIG. 7 illustrates a partial cross-sectional view of the drill guide of FIG. 6 inserted into the first fastener of FIG. 4A, in accordance with one or more aspects of the present invention.
Figure 8A:
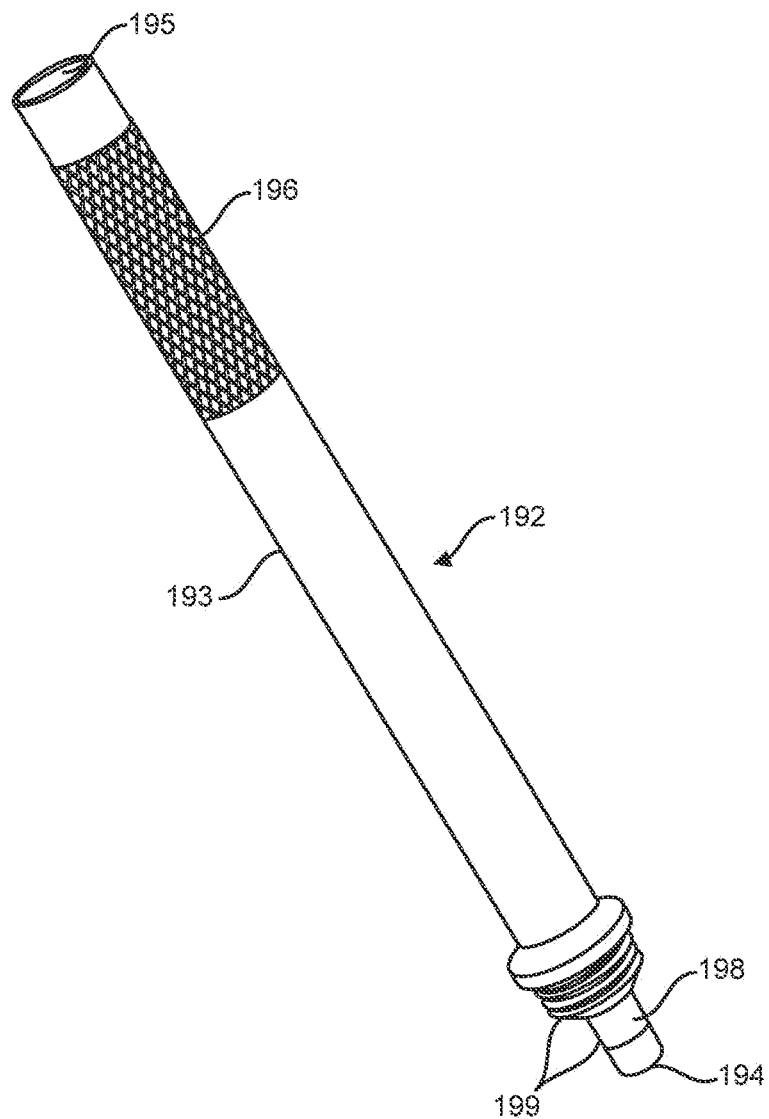
FIG. 8A illustrates a perspective view of one embodiment of a drill guide for use with the bone fixation system of FIG. 1, in accordance with one or more aspects of the present invention.
Figure 8C:
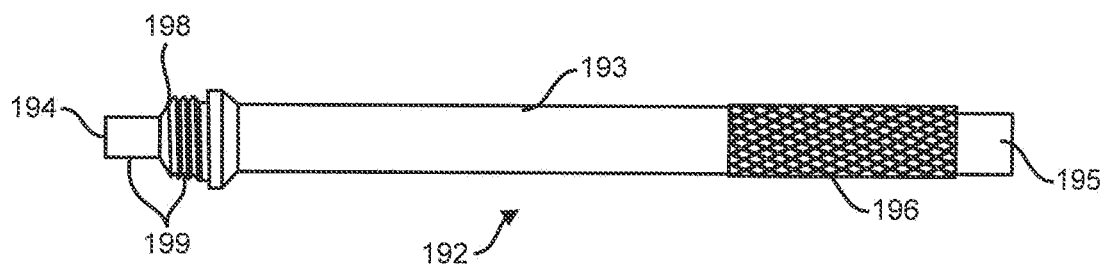
FIG. 8C illustrates a side view of the drill guide of FIG. 8A, in accordance with one or more aspects of the present invention.
Figure 8D:
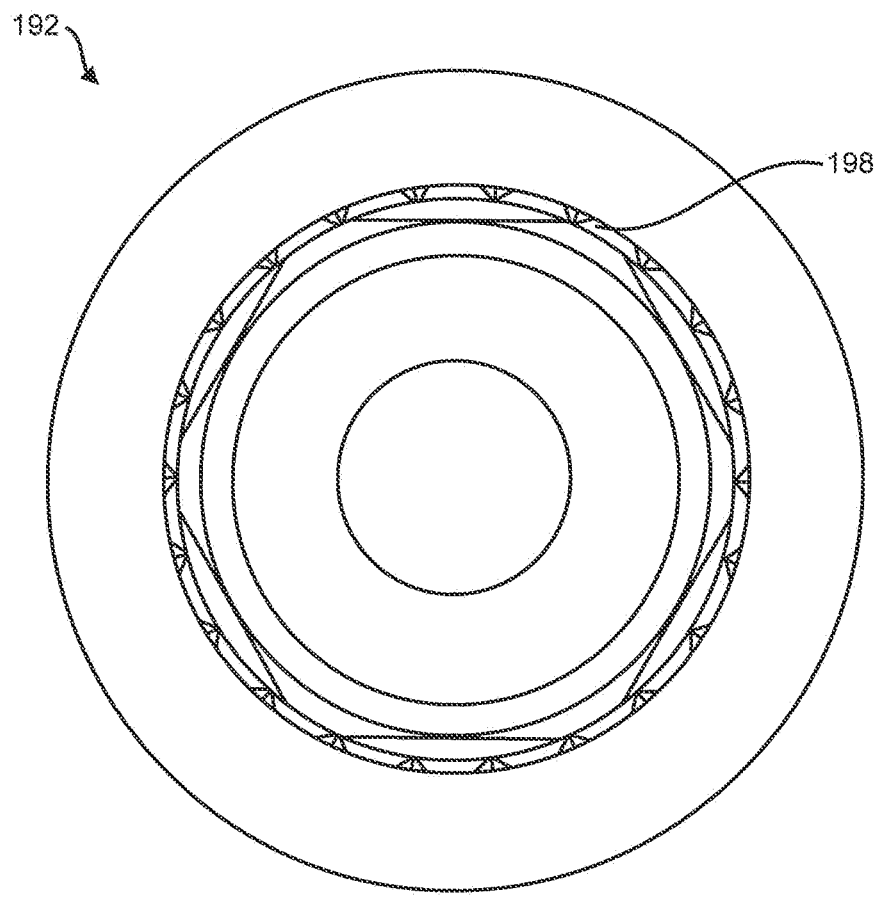
FIG. 8D illustrates an end view of the drill guide of FIG. 8A, in accordance with one or more aspects of the present invention.
Figure 8E:
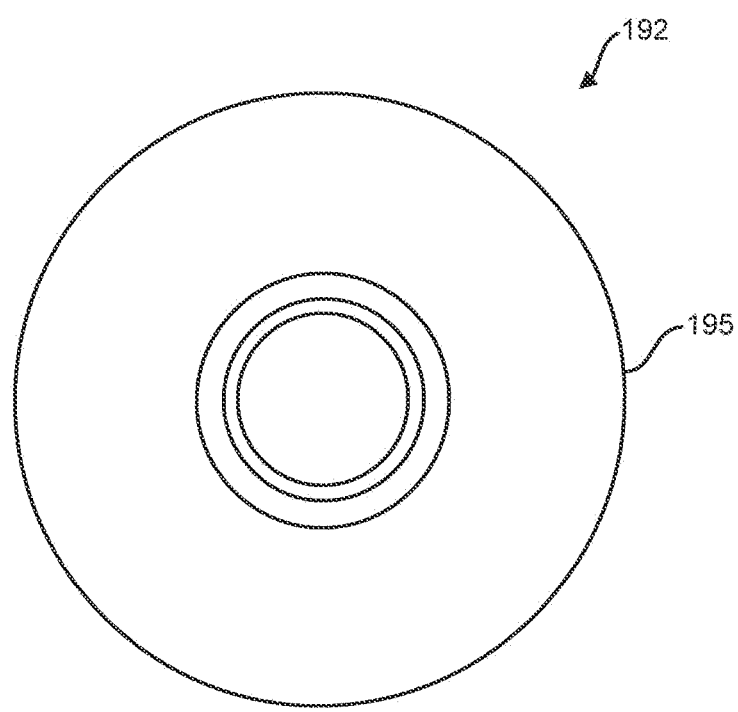
FIG. 8E illustrates an opposing end view of the drill guide of FIG. 8A, in accordance with one or more aspects of the present invention.
Figure 9:
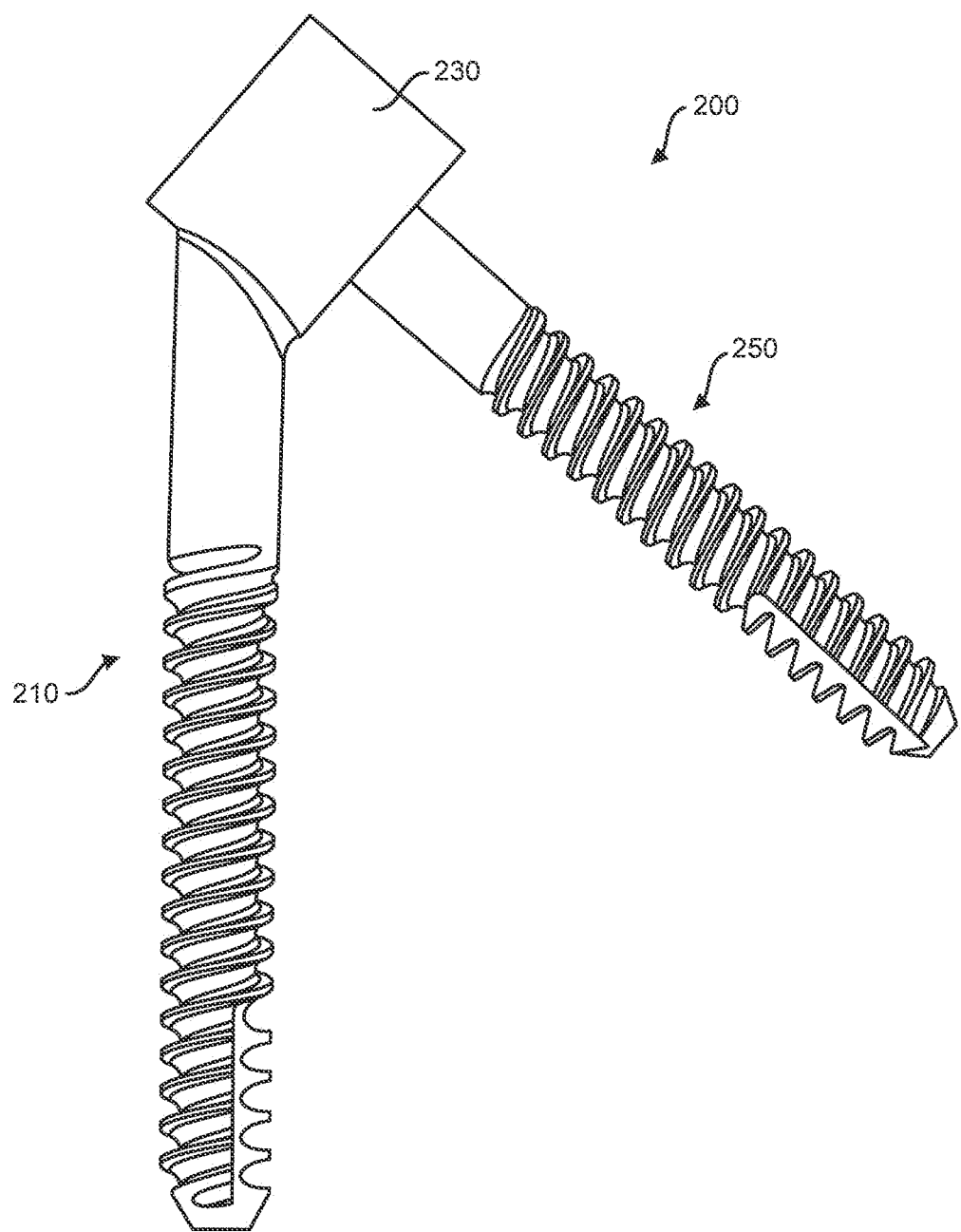
FIG. 9 illustrates a side view of another embodiment of a bone fixation system, in accordance with one or more aspects of the present invention.
Figure 10:
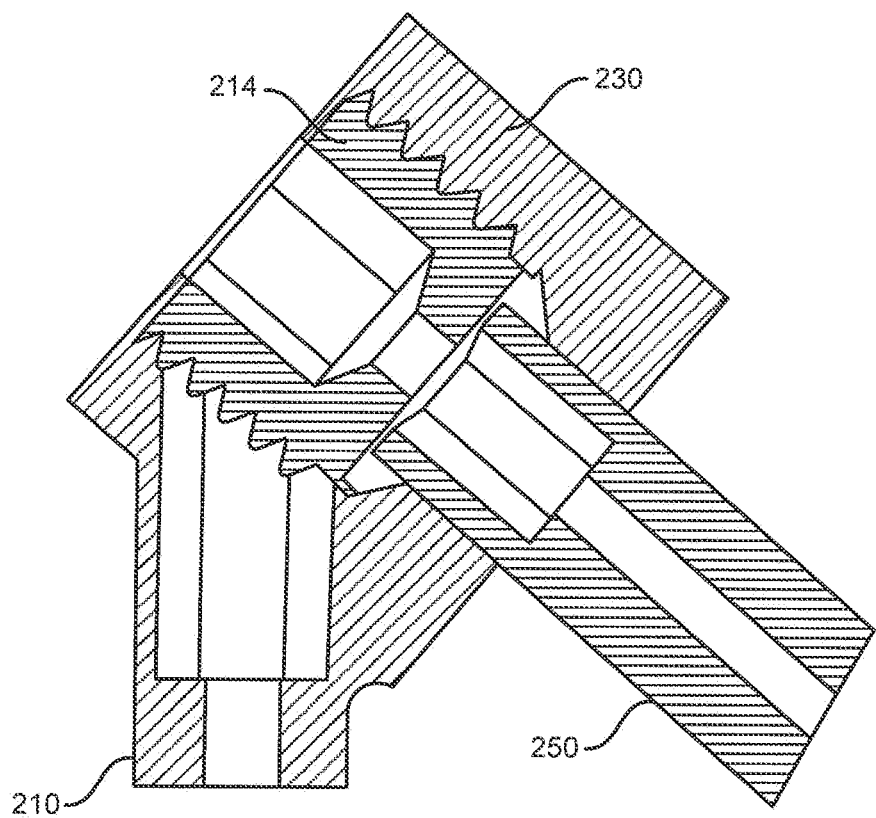
FIG. 10 illustrates a partial cross-sectional view of the bone fixation system of FIG. 9, in accordance with one or more aspects of the present invention.

Prior to insertion of second fastener 150 through first fastener 110 and into a second desired bone, a drill guide may be used to pre-drill a hole in the bone. FIGS. 6-8E illustrate one embodiment of a drill guide that may be used in system 100. As illustrated in FIG. 8A, drill guide 192 may include a hollow elongated shaft 193 having a first end 194, a second end 195, a handle portion 196 proximate second end 195 and a head 198 at first end 194. Head 198 includes an exterior surface 199. Exterior surface 199 may be configured, sized and shaped to engage threaded portion 142 and seat 144 of interior surface 136 of head 130 of first fastener 110. As illustrated in FIG. 7, head 198 of drill guide 192 is received by and inserted into passageway 132. The engagement of threads on exterior surface 199 of drill guide 192 and threaded portion 142 on interior surface 136 provide stability of drill guide 192 in relation to first fastener 110 for pre-drilling the hole for second fastener 150.

Another embodiment of a bone fixation system 200 is shown in FIGS. 9-13D. Bone fixation system 200 may include a first or primary fastener 210 for anchoring into, for example, a first vertebrae, a second or secondary fastener 250 for anchoring into, for example, a second vertebrae, and a set screw or locking cap 214.

With continued reference to FIGS. 11A-11E, first fastener 210 may include a shaft 220, a head 230 and a longitudinal axis 221. Shaft 220 may include a neck 212 connecting shaft 220 to the head 230. Shaft 220 also includes an outer surface 214. A portion of the outer surface 214 of shaft 220 may include one or more bone engagement mechanisms 222 to facilitate a gripping engagement of first bone anchor to bone. In one example illustrated in FIG. 11A, shaft 220 may be, for example, threaded along its entire length, threaded along only a portion of the length, or non-threaded. In the illustrated embodiment, the external thread is a single lead thread that extend from a distal tip of the shaft to the proximal head portion. Other suitable bone engagement mechanisms may include, but are not limited to, one or more annular ridges, multiple threads, dual lead threads, variable pitched threads, longitudinal splines or other geometries, and/or any conventional bone engagement mechanism.

Figure 11A:
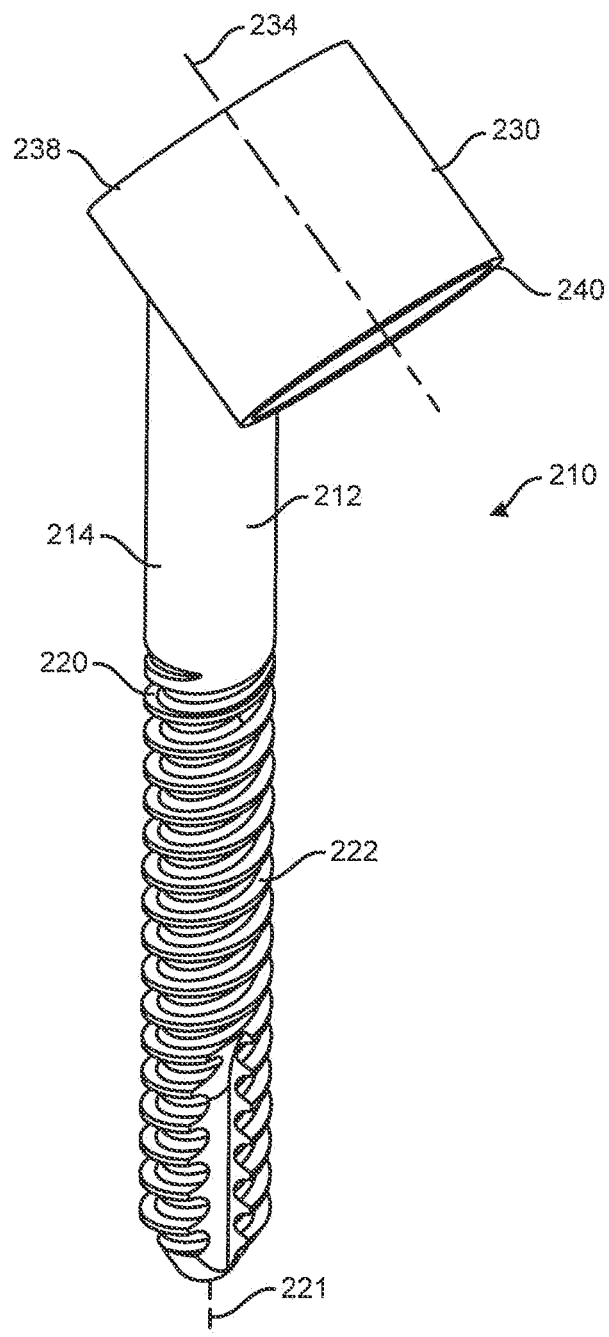
FIG. 11A illustrates a perspective view of one embodiment of a first fastener of the bone fixation system of FIG. 9, in accordance with one or more aspects of the present invention.
Figure 11B:
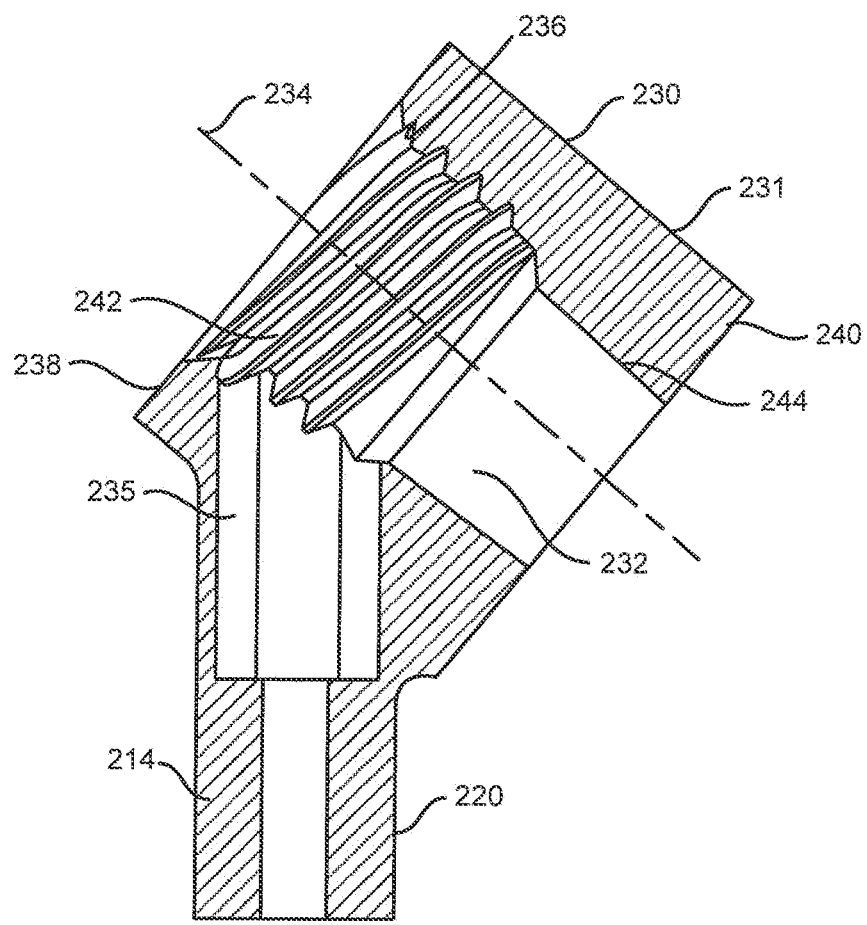
FIG. 11B illustrates a partial cross-sectional view of the first fastener of FIG. 11A, in accordance with one or more aspects of the present invention.
Figure 11C:
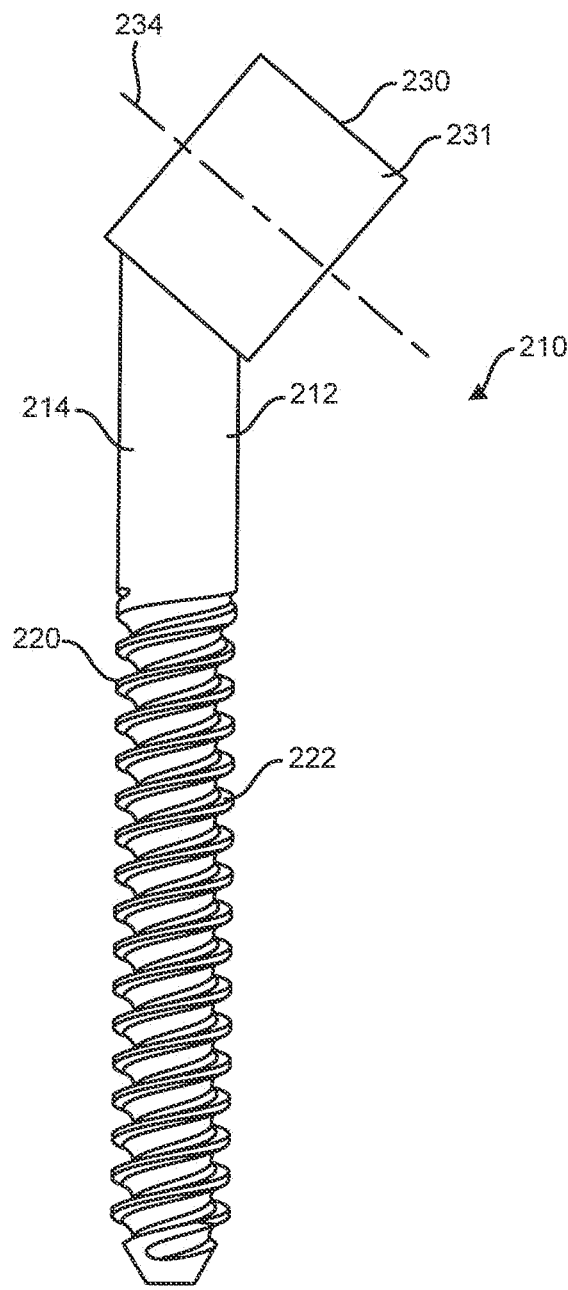
FIG. 11C illustrates a side view of the first fastener of FIG. 11A, in accordance with one or more aspects of the present invention.
Figure 11D:
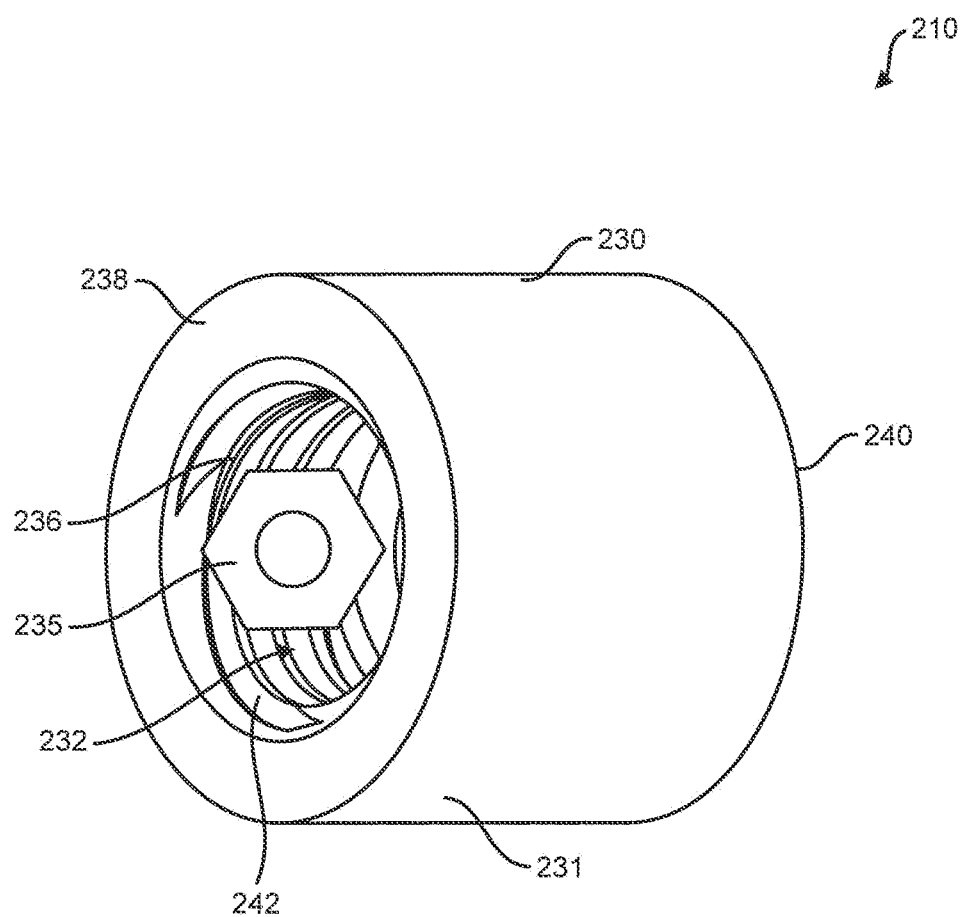
FIG. 11D illustrates a top view of the first fastener of FIG. 11A, in accordance with one or more aspects of the present invention.
Figure 11E:
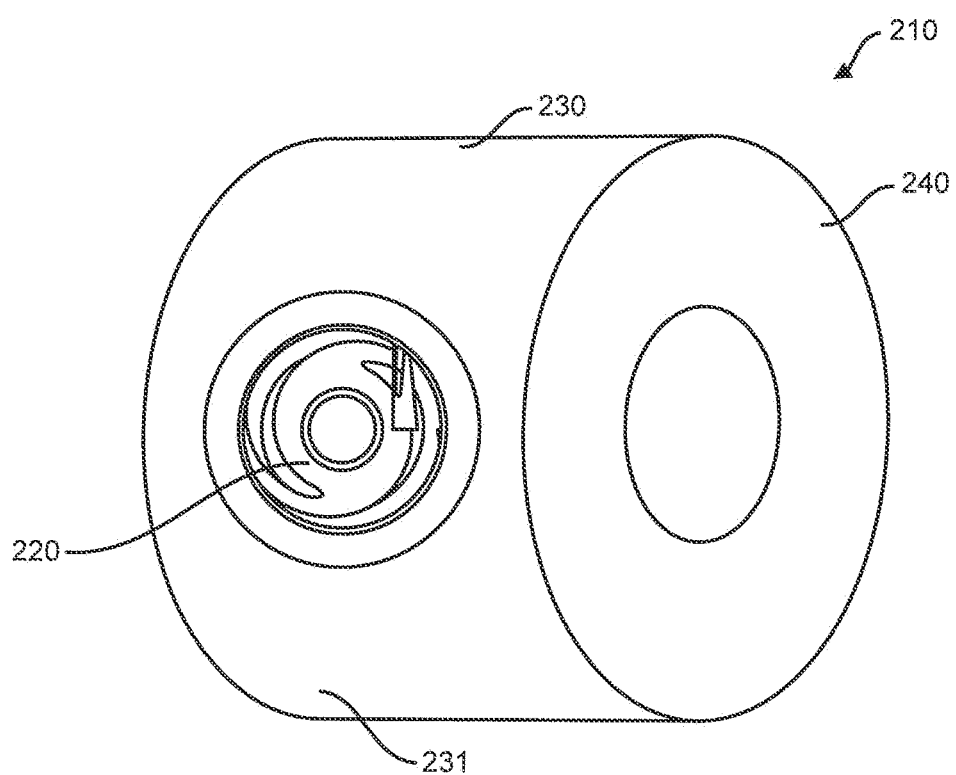
FIG. 11E illustrates a bottom view of the first fastener of FIG. 11A, in accordance with one or more aspects of the present invention.

As shown in FIG. 11B, head 230 includes a cylindrical body 231. In one embodiment, the diameter of cylindrical body 231 is greater than the diameter of shaft 220 extending to outer surface 214. When connected to neck 212, head 230 appears like a halo over shaft 220. Head 230 may form a receiving portion, such as, for example, a passageway 232 having a longitudinal axis 234. Passageway 232 may be in the form of, for example, a through hole or, alternatively, a slot formed between two arms. Passageway 232 defines an interior cavity or space having an inner surface 236 extending from a first end 238 to a second end 240. In one embodiment, first end 238 and second end 240 extend beyond the outer surface 214 of shaft 220. Passageway 232 may be sized and configured to receive and allow pass through of a second fastener 250 or other spinal connection element for anchoring the system 200 to, for example, a second bone or vertebrae. Passageway 232 is also configured to retain or secure set screw 214 and at least a portion of head 280 of second fastener 250.

In one embodiment illustrated in FIG. 11B, interior surface 236 of passageway 232 may include, for example, a threaded portion 242 that extends along at least a portion of interior surface 236 from first end 238. Passageway 232 may also include a seat 244 that may extend along at least another portion of interior surface 236 towards second end 240. In one example, seat 244 may be formed by interior surface 236 tapering inward towards longitudinal axis 234 as it approaches second end 240.

Figure 12A:
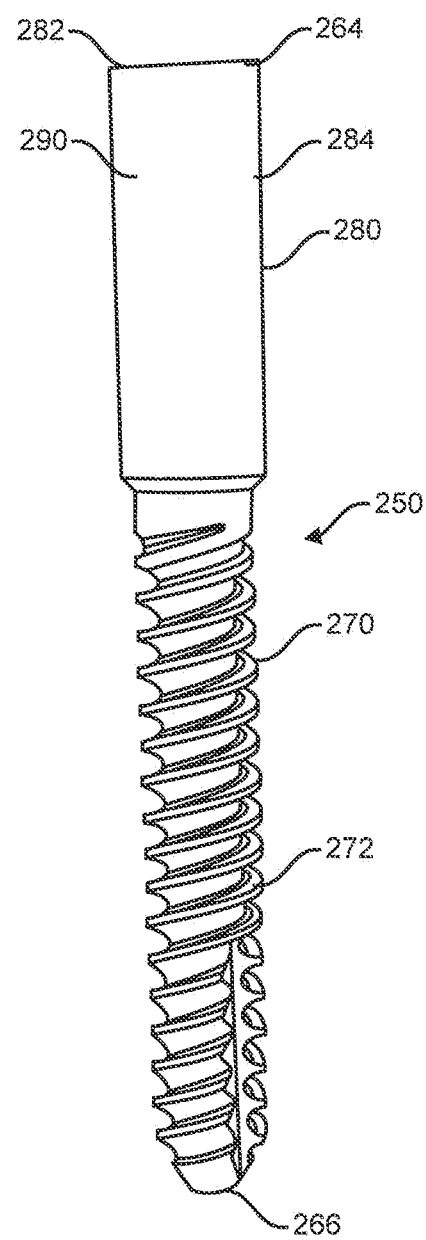
FIG. 12A illustrates a side view of one embodiment of a second fastener of the bone fixation system of FIG. 9, in accordance with one or more aspects of the present invention.
Figure 12B:
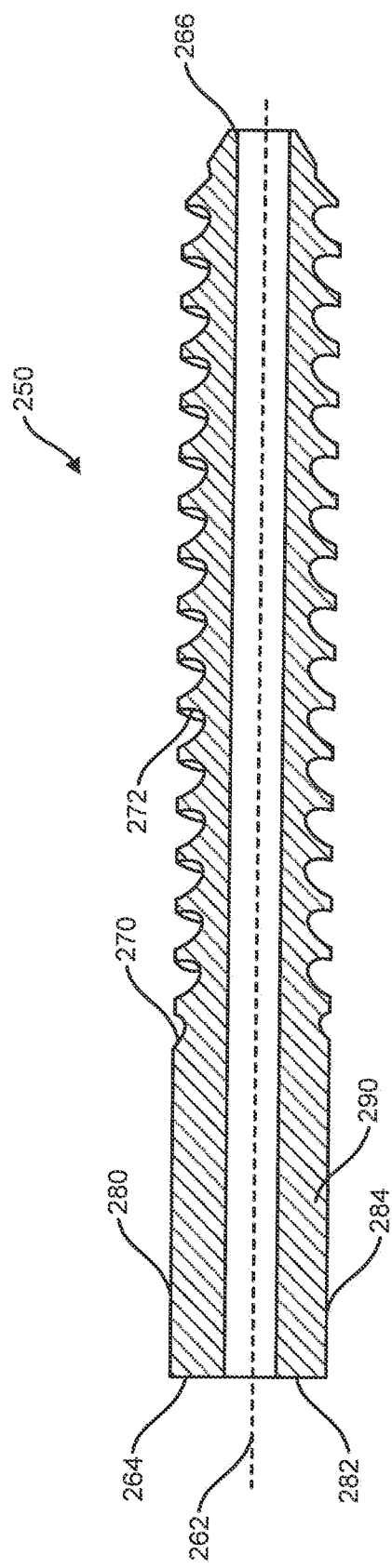
FIG. 12B illustrates a cross-sectional view of the second fastener of FIG. 12A, in accordance with one or more aspects of the present invention.
Figure 12C:
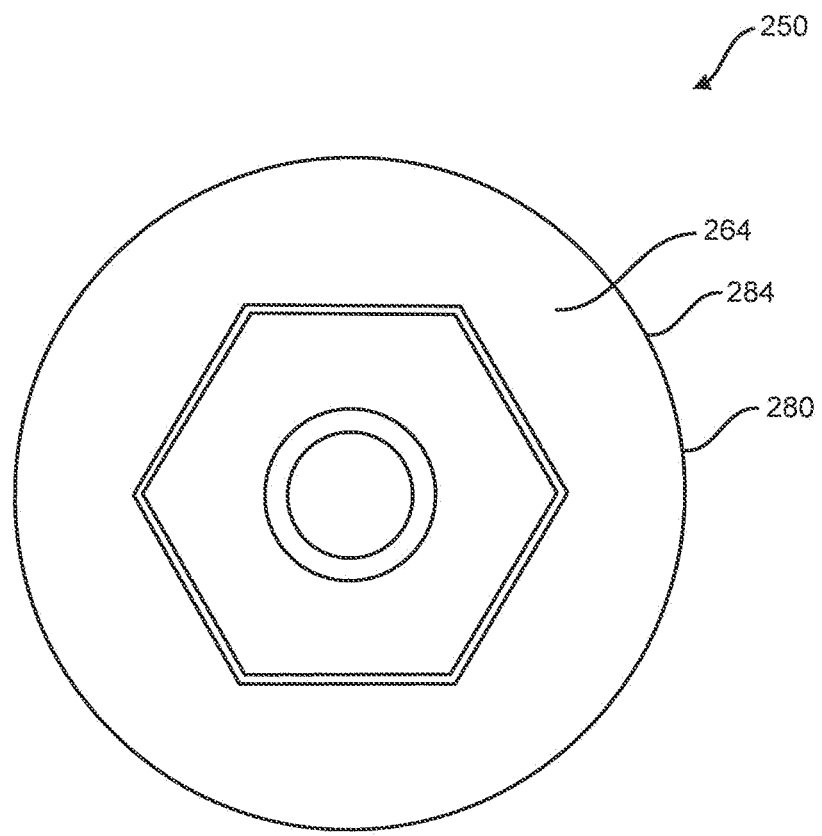
FIG. 12C illustrates a top view of the second fastener of FIG. 12A, in accordance with one or more aspects of the present invention.
Figure 13A:
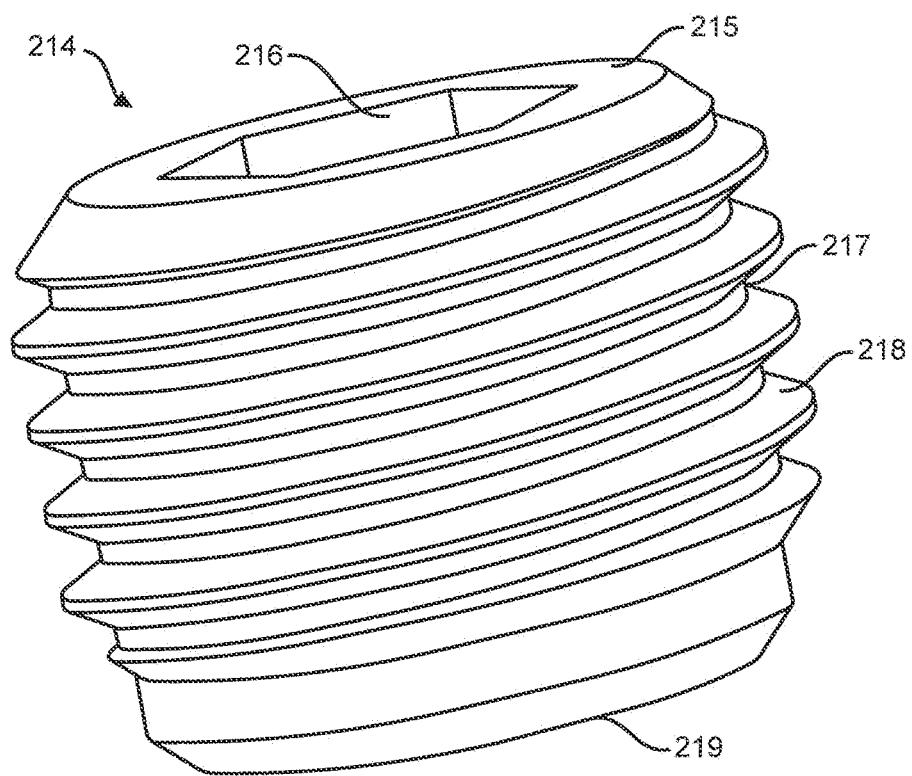
FIG. 13A illustrates a perspective view of one embodiment of a set screw of the bone fixation system of FIG. 9, in accordance with one or more aspects of the present invention.
Figure 13B:
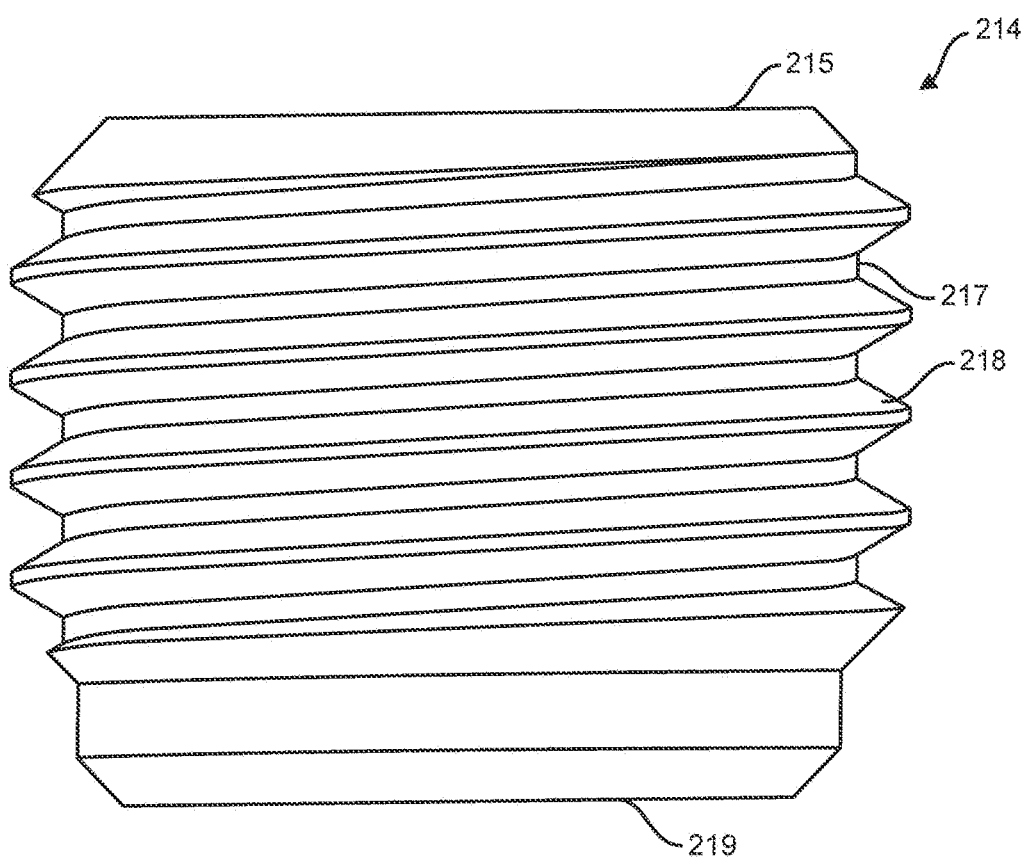
FIG. 13B illustrates a side view of the set screw of FIG. 13A, in accordance with one or more aspects of the present invention.
Figure 13C:
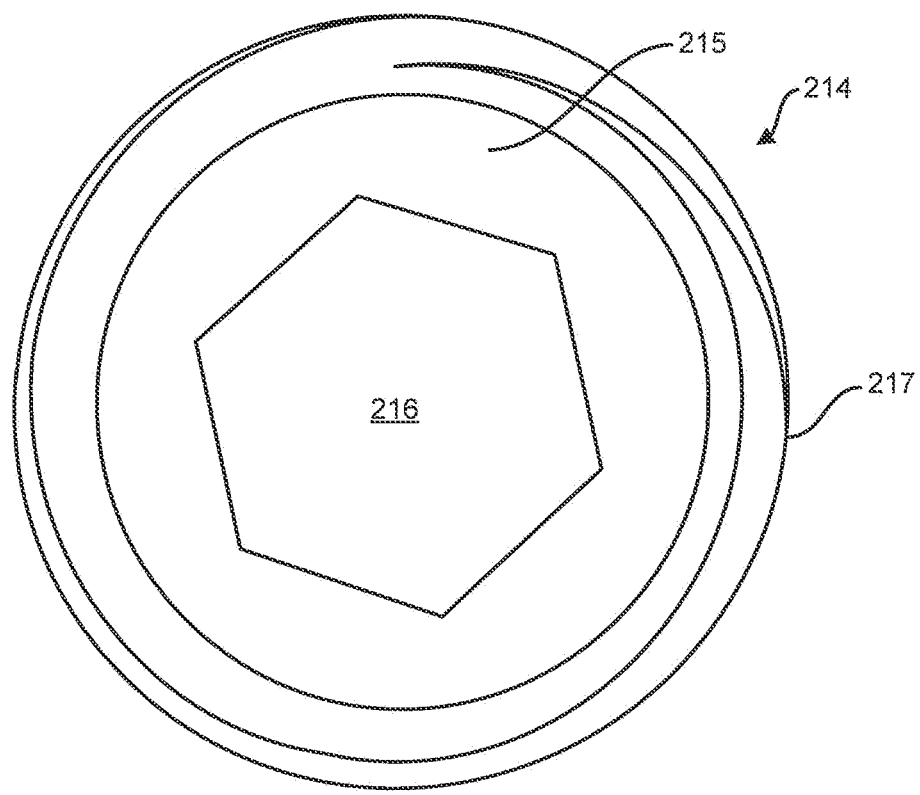
FIG. 13C illustrates a top view of the set screw of FIG. 13A, in accordance with one or more aspects of the present invention.
Figure 13D:
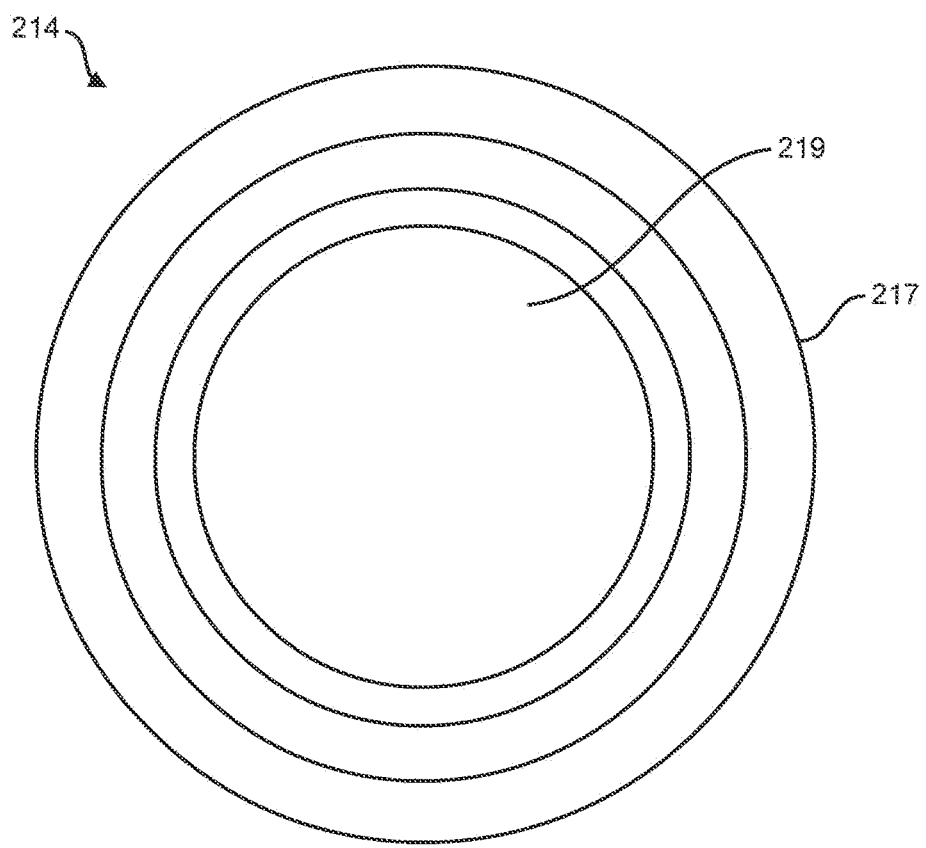
FIG. 13D illustrates a bottom view of the set screw of FIG. 13A, in accordance with one or more aspects of the present invention.
Figure 14:
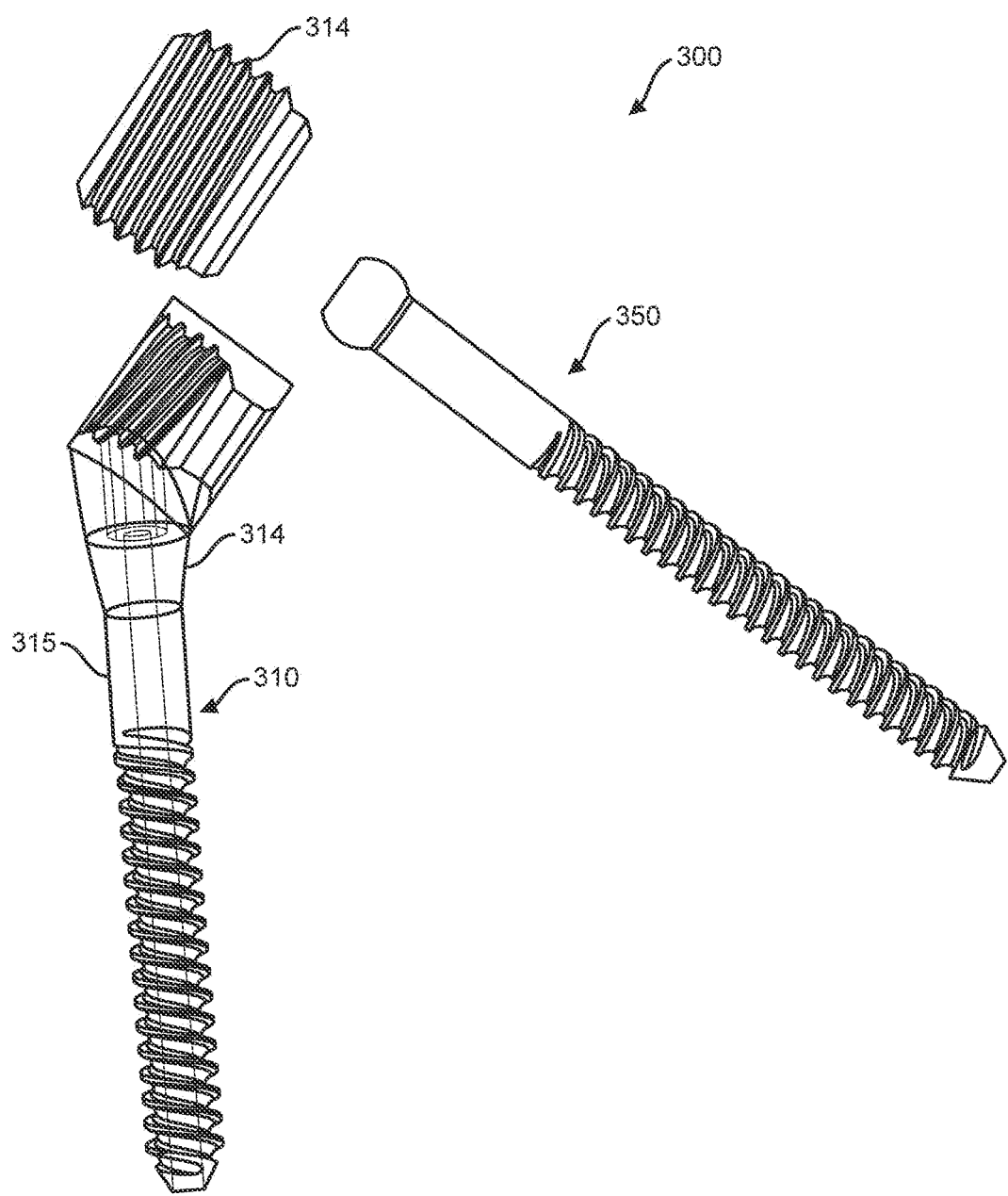
FIG. 14 illustrates an exploded side view of another embodiment of a bone fixation system, in accordance with one or more aspects of the present invention.
Figure 15:
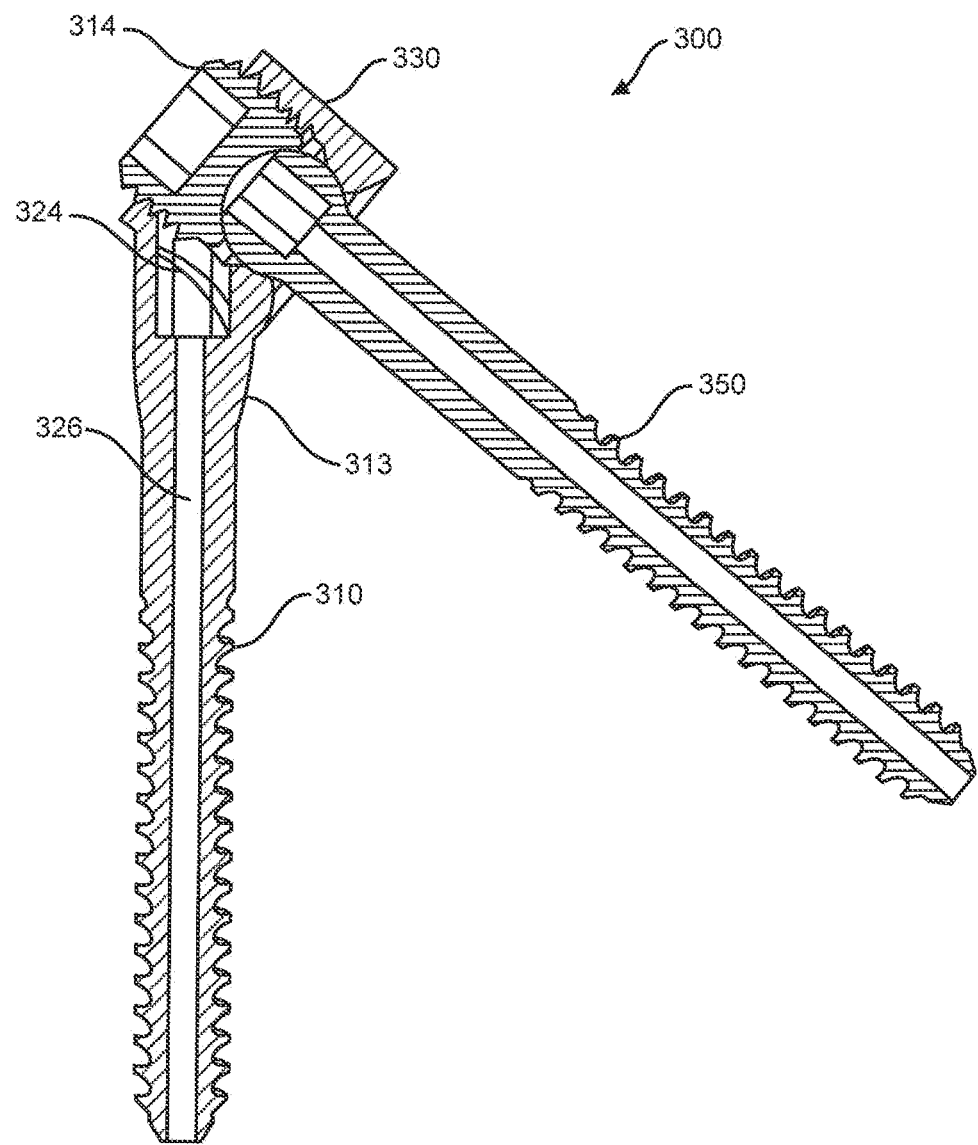
FIG. 15 illustrates a cross-sectional view of the bone fixation system of FIG. 14, in accordance with one or more aspects of the present invention.

As illustrated in FIGS. 12A-12C, second fastener 250 may include a longitudinal axis 262, a proximal end 264, a distal end 266, a shaft 270, and a head 280. Shaft 270 may include one or more bone engagement mechanisms 272 to facilitate a gripping engagement of second fastener to bone. Shaft 270 may be, for example, threaded along its entire length, threaded along only a portion of the length, or non-threaded. In the illustrated embodiment, the external thread, for example, is a single lead thread that extends from a distal tip of the shaft to the proximal head portion. Other suitable bone engagement mechanisms may include, but are not limited to, one or more annular ridges, multiple threads, dual lead threads, variable pitched threads, longitudinal splines or other geometries, and/or any conventional bone engagement mechanism.

As shown in FIG. 12A, head 280 may include a top surface 282 and a side portion 284. Top surface 282 may include a tool engagement opening (see FIG. 12C) extending into head 280. Side portion 284 of head 280 may include an exterior surface 290 that tapers inward towards longitudinal axis 262. The tapered exterior surface 290 is configured to engage and mate with seat 244 of passageway 232.

As shown in FIGS. 13A-13D, set screw 214 may include a top surface 215, side surface 217 and a bottom surface 219. Set screw 214 may also include a tool engagement opening 216 extending into set screw 214 from top surface 215 toward bottom surface 219. In addition, set screw 214 may include threads 218 on side surface 217 extending, for example, from top surface 215 to bottom surface 219, or along a portion thereof. Bottom surface 219 may be sized and shaped to engage at least a portion of head 280 of second fastener 250.

The system 200 may be implanted by first preparing a patient's vertebrae for insertion of the bone fixation system 200. Next, the first fastener 210 is screwed or inserted into the bone, e.g. vertebrae. In inserting first fastener 210 into the bone, a surgeon may use a screw driver that engages a tool engagement opening 235 (see FIG. 11D) formed within passageway 230. Next, second fastener 250 is inserted through head 230 of first fastener 210 and into a second desired bone until exterior tapered surface 290 engages seat 244 of passageway 232 of head 230 of first fastener 210. When properly installed, the entire head 230 and a portion of shaft 120 of first fastener 210 and/or shaft 270 of second fastener 250 are positioned and reside outside the bone(s) in which first fastener 210 and second fastener 250 are inserted. By positioning head 230 outside the vertebrae, bone fixation system 200 is configured to aid in the fusion of multi-levels of vertebrae.

Prior to insertion of second fastener 250 into first fastener 210, drill guide 192 may be used to pre-drill a hole in the bone. Next, set screw 214 may be inserted or screwed into passageway 232 to secure second fastener 250 in the desired position. Finally, the patient's incision may be closed. In the system 210 illustrated in FIGS. 9-13D, second fastener 250 is orientated in a fixed angled relationship relative to first fastener 210. This fixed angle is created by engagement of tapered surface 290 of side portion 284 of head 280 of second fastener 250 with seat 244 of passageway 232 of first fastener 210.

Another embodiment of a bone fixation system 300 is shown in FIGS. 14-22D. Bone fixation system 300 may include a first or primary fastener 310 for anchoring into, for example, a first vertebrae, a second or second fastener 350 for anchoring into, for example, a second vertebrae, and a set screw or locking cap 314. In one example, first fastener 310 may be cannulated with a threaded halo head, second fastener 350 may be cannulated with an articulating spherical head, and set screw 314 may be cannulated and include a bottom surface for capturing and securing the spherical head of second fastener 350.

Figure 17A:
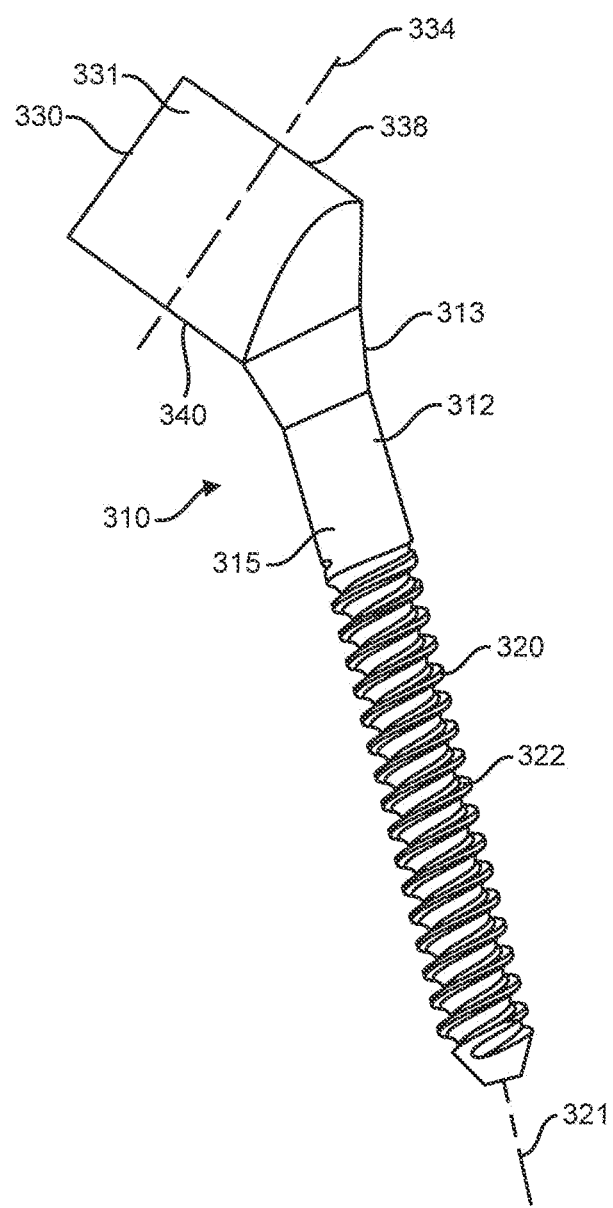
FIG. 17A illustrates a side view of one embodiment of a first fastener of the bone fixation system of FIG. 14, in accordance with one or more aspects of the present invention.
Figure 17B:
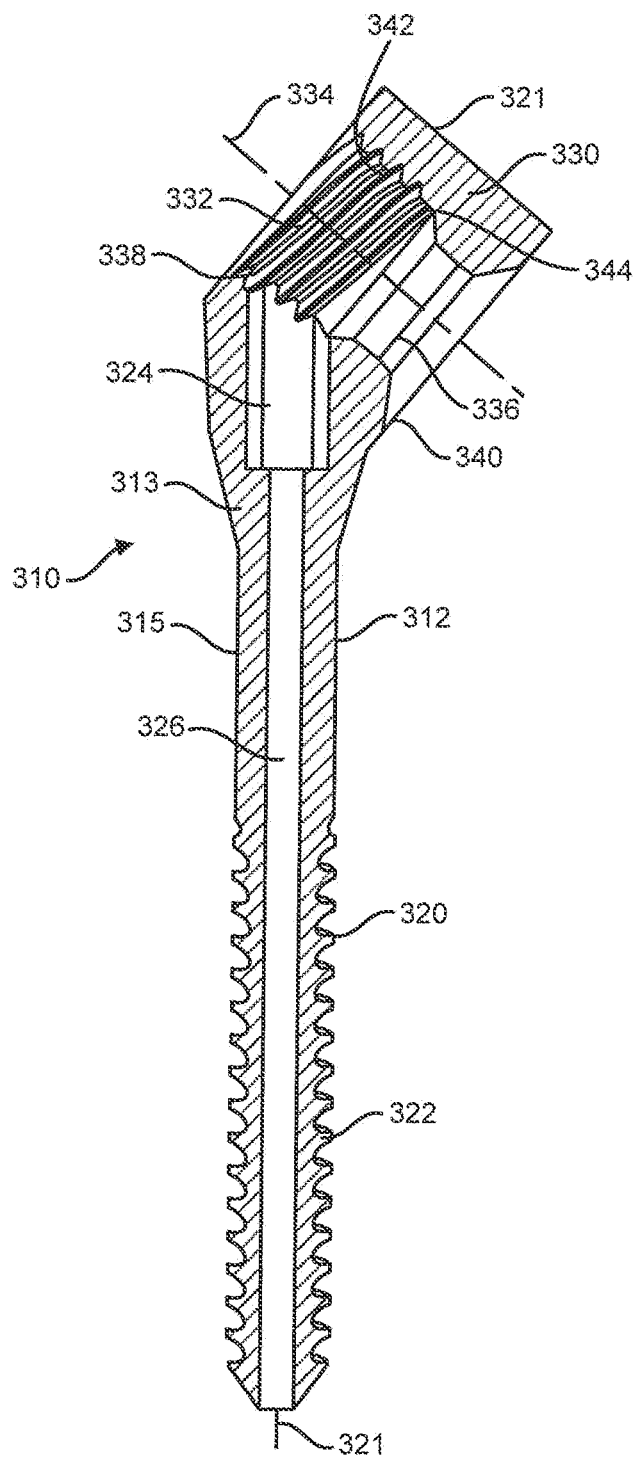
FIG. 17B illustrates a cross-sectional view of the first fastener of FIG. 17A, in accordance with one or more aspects of the present invention.
Figure 17C:
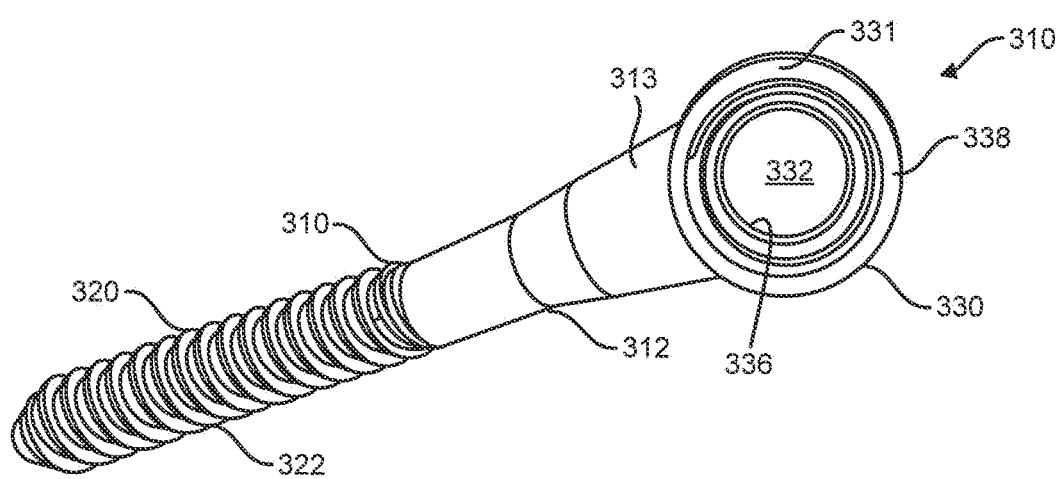
FIG. 17C illustrates a top view of the first fastener of FIG. 17A, in accordance with one or more aspects of the present invention.
Figure 17D:
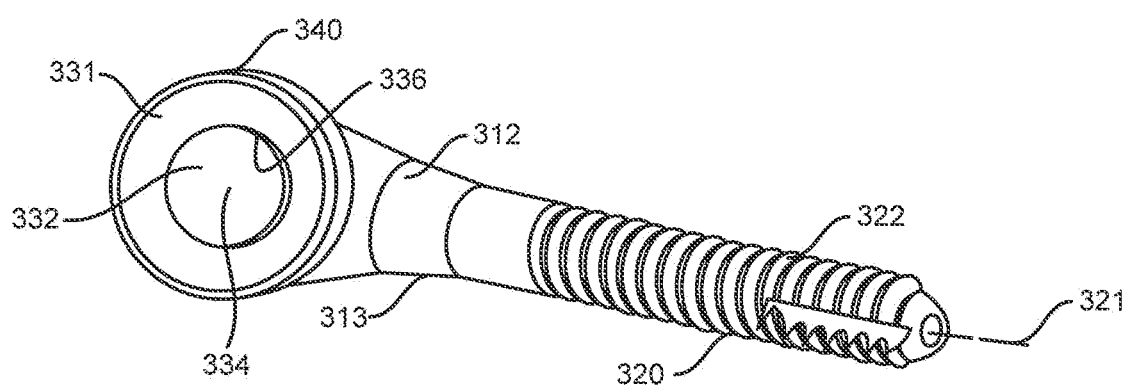
FIG. 17D illustrates a bottom view of the first fastener of FIG. 17A, in accordance with one or more aspects of the present invention.

As shown in FIGS. 17A-17D, first fastener 310 may include a cannulated shaft 320, a head 330 and a longitudinal axis 321. Shaft 320 may include a neck 312 connecting shaft 320 to the head 330 and an outer surface 313. In one example, as illustrated in FIGS. 17A and 17B, a portion of outer surface 313 of neck 312 may taper radially outward relative to longitudinal axis 321 to provide additional thickness to neck 312 of shaft 320 as it approaches head 330. This taper or increased thickness provides, for example, enhancement of the fastener to bone interface thereby providing enhanced stability by increasing compressive load and reduces failure through facture of the fastener.

A portion of outer surface 313 of shaft 320 may include one or more bone engagement mechanisms 322 to facilitate a gripping engagement of first bone anchor to bone. In one example illustrated in FIG. 17A, shaft 320 may be, for example, threaded along its entire length, threaded along only a portion of the length, or non-threaded. In the illustrated embodiment, the external threads, for example, may be a single lead thread that extend from a distal tip of the shaft to the proximal head portion. Other suitable bone engagement mechanisms may include, but are not limited to, one or more annular ridges, multiple threads, dual lead threads, variable pitched threads, longitudinal splines or other geometries, and/or any conventional bone engagement mechanism.

As illustrated in FIG. 17B, head 330 includes a cylindrical body 331. In one embodiment, the diameter of cylindrical body 331 is greater than the diameter of shaft 320 extending to outer surface 313. Head 330 may form a receiving portion, such as, for example, a passageway 332 having a longitudinal axis 334. Passageway 332 may be in the form of, for example, a through hole or, alternatively, a slot formed between two arms. Passageway 332 defines an interior cavity or space having an inner surface 336 extending from a first end 338 to a second end 340. In one embodiment, first end 338 and second end 340 extend beyond the outer surface 313 of shaft 320. Passageway 332 may be sized and configured to receive and allow pass through of a second fastener 350 or other spinal connection element for anchoring the system 300 to, for example, a second bone or vertebrae. Passageway 332 is also configured to retain or secure set screw 314 and at least a portion of head 380 of second fastener 350.

In one embodiment illustrated in FIG. 17B, interior surface 336 of passageway 323 may include, for example, a threaded portion 342 that extends along at least a portion of interior surface 336 from first end 338. Passageway 332 may also include a seat 344 that may extend along at least another portion of interior surface 336 towards second end 340. In one example, seat 344 may be shaped to correspond and mate with the shape of a portion of head 380 of second fastener 350.

Passageway 332 is in communication with the cannulated tube or passageway extending through shaft 320 of first fastener 310. In one example, passageway 323 and the cannulated tube or passageway extending through shaft 320 are configured to receive a K-wire to assist in inserting first fastener 310 into the bone or vertebrae at a proper location and position. A tool engagement opening 324 such as, for example, a cannulated hex receiver hole, is formed in interior surface 336 and into shaft 320 between passageway 323 and the cannulated tube 326. Tool engagement opening 324 receives a hex driver or screwdriver and assists in inserting or screwing first fastener 310 into the bone.

As illustrated in FIGS. 18A-18D, second fastener 350 may include a longitudinal axis 362, a proximal end 364, a distal end 366, a cannulated shaft 370, a head 380 and a neck 368 connecting shaft 370 to head 380. The outer surface of shaft 370 may include one or more bone engagement mechanisms 372 to facilitate a gripping engagement of second fastener to bone. Shaft 370 may be, for example, threaded along its entire length, threaded along only a portion of the length, or non-threaded. In the illustrated embodiment, the external thread is a single lead thread that extend from a distal tip of the shaft to the proximal head portion. Other suitable bone engagement mechanisms may include, but are not limited to, one or more annular ridges, multiple threads, dual lead threads, variable pitched threads, longitudinal splines or other geometries, and/or any conventional bone engagement mechanism.

Figure 18A:
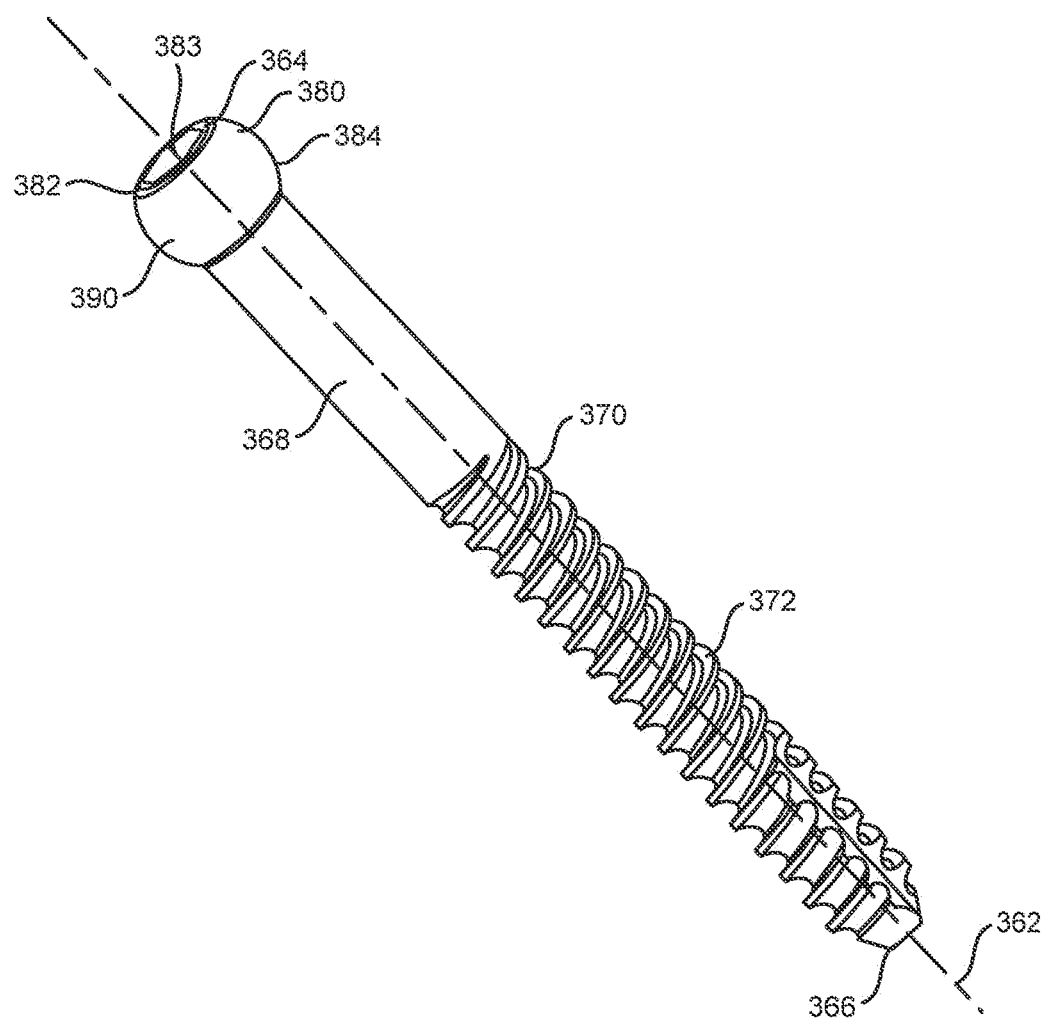
FIG. 18A illustrates a perspective view of one embodiment of a second fastener of the bone fixation system of FIG. 14, in accordance with one or more aspects of the present invention.
Figure 18B:
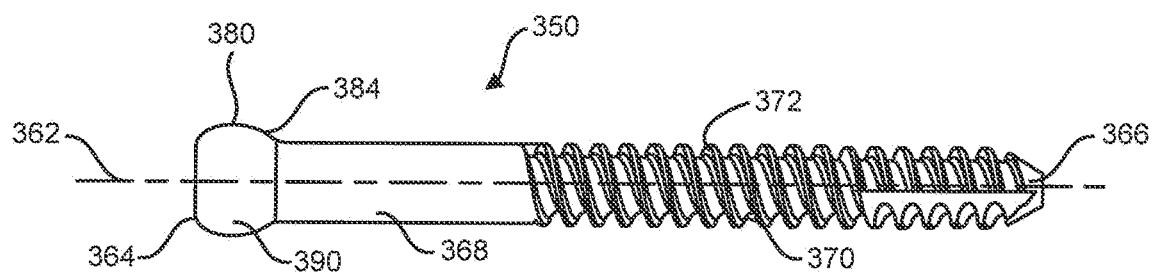
FIG. 18B illustrates a side view of the second fastener of FIG. 18A, in accordance with one or more aspects of the present invention.
Figure 18C:
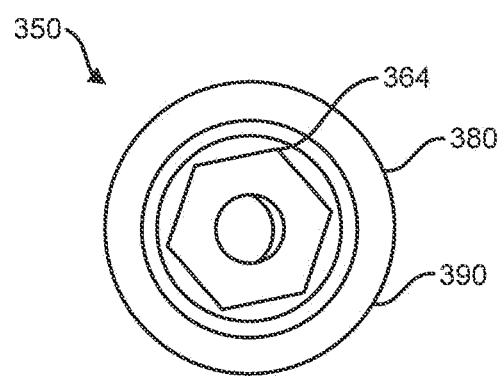
FIG. 18C illustrates a top view of the second fastener of FIG. 18A, in accordance with one or more aspects of the present invention.
Figure 18D:
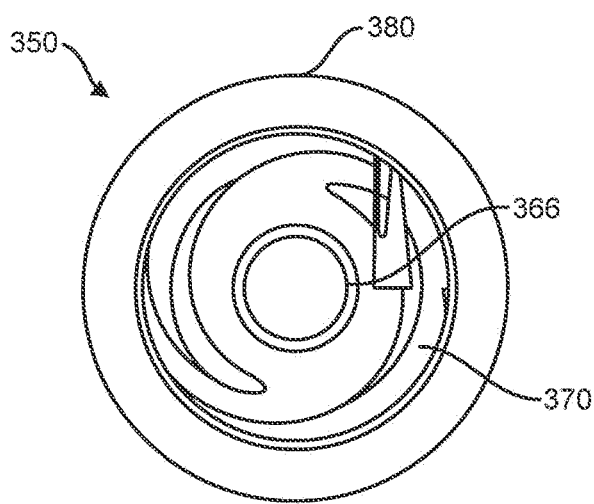
FIG. 18D illustrates a bottom view of the second fastener of FIG. 18A, in accordance with one or more aspects of the present invention.

As illustrated in FIG. 18A, head 380 may include a top surface 382 and a side portion 384. Top surface 382 may include a tool engagement opening 383 extending into head 380. Side portion 384 of head 380 may include an exterior surface 390 shaped like, for example, a polyaxial screw head in the form of, for example, a bulbous head, hemispherical, or partially spherical head. Exterior surface 390 may be shaped to lie in or mate with seat 344 formed in interior surface 336 of passageway 332 of head 330 of first fastener 310 near second end 340. Seat 344 preferably has a shape that matches or corresponds to the shape of a portion of the polyaxial side portion 384 and allows, for example, pivoting, spinning and rotation of second fastener 350 relative to longitudinal axis 334 of head 330 of first fastener 310. This configuration allows a range of motion along several different axes, e.g. multi-directional movement or rotation or angulation, of second fastener 350 relative to longitudinal axis 334. For example, a round head 380 of second fastener 350 mating with a mating concave-shaped seat 344 enables a variation of angulation to accommodate pedicle screw insertion in variable anatomy. Such a round head 380 transfers the variable angulation from the tulip head of a traditional pedicle screws to the secondary fastener 350.

Figure 16A:
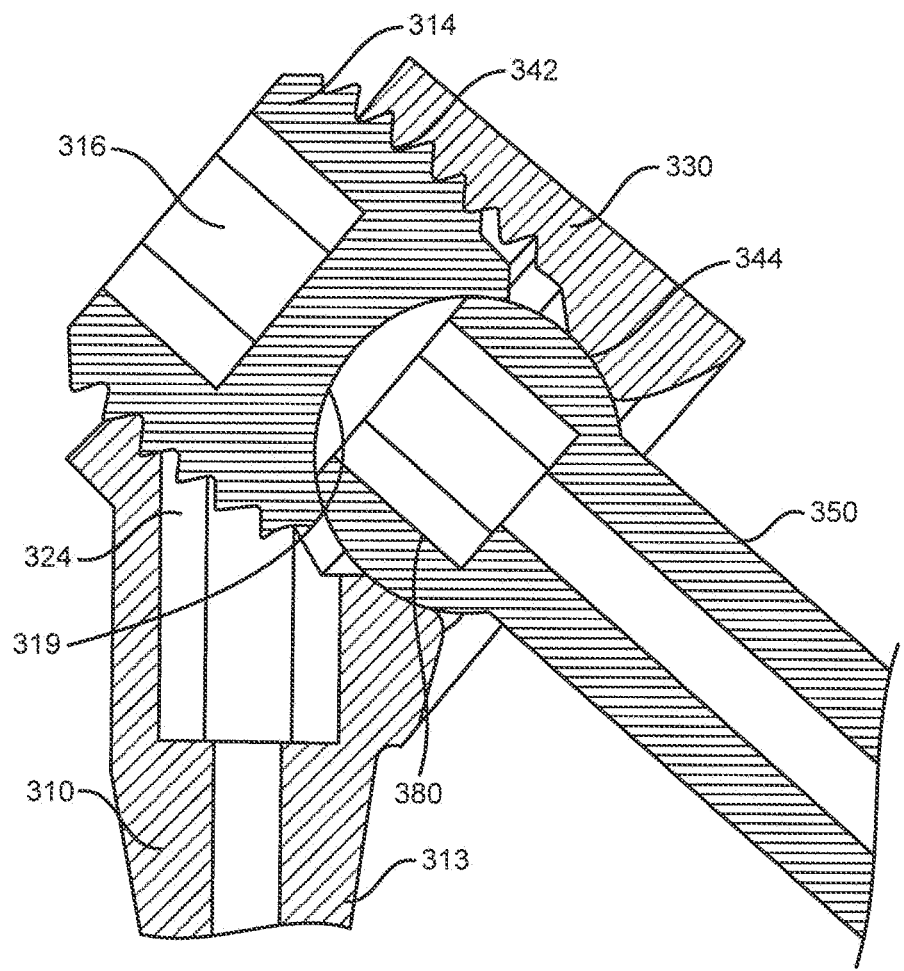
FIG. 16A illustrates a partial cross-sectional view of the bone fixation system of FIG. 14, in accordance with one or more aspects of the present invention.
Figure 16B:
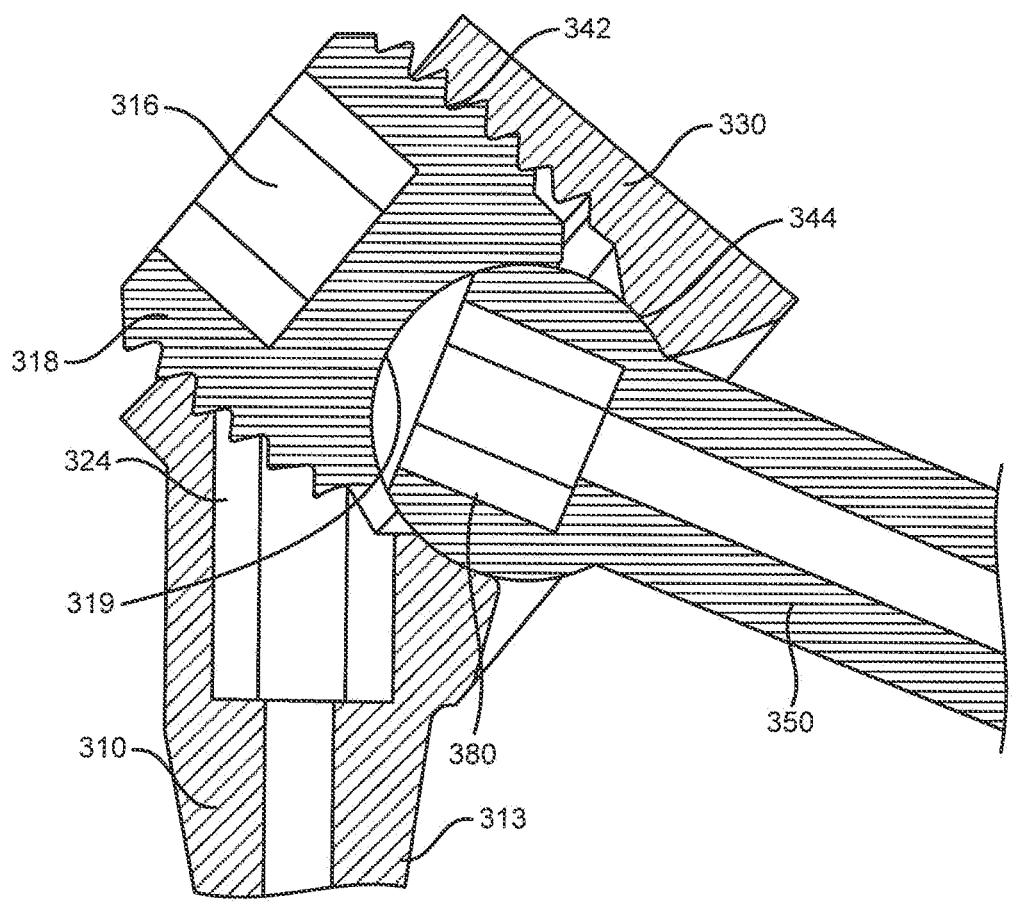
FIG. 16B illustrates another partial cross-sectional view of the bone fixation system of FIG. 14, in accordance with one or more aspects of the present invention.

After second fastener 350 is positioned into bone in a selected direction and orientation relative to first fastener 310, set screw 314, as illustrated in FIGS. 19A-19D, may lock the orientation of second fastener 350 relative to first fastener 310. Set screw 314 may have any suitable size, configuration and means for securing polyaxial screw head 380 to seat 344 in a selected orientation relative to first fastener 310. In one embodiment shown in FIGS. 19A-19D, set screw 314 may include a top surface 315, side surface 317 and a bottom surface 319. Set screw 314 may also include a tool engagement opening 316 extending into set screw 314 from top surface 315 toward bottom surface 319. In one example, set screw 314 may be cannulated, but in other examples may not. In addition, set screw 314 may include threads 318 on side surface 317 extending, for example, from top surface 315 to bottom surface 319, or along a portion thereof. As shown in FIGS. 16A and 16B, bottom surface 319 is sized and shaped to retain head 380 with the aid of seat 344.

The concave contour of bottom surface 319 of set screw 380 is configured to match or correspond to head 380 of second fastener 350 in order to, for example, maximize surface contact and, therefore, maximize the rigidity of the system. In one embodiment, bottom surface 219 may include a surface treatment, such as, for example, surface etching, which engages and/or interacts with head 380 of second fastener 350 to provide, for example, enhanced rigidity through a friction fit that prevents shifting of second fastener 350 once secured. In one example, head 380 may also include a surface treatment or similar surface etching that engages and/or interacts with bottom surface 319 of set screw 314. When properly installed, the entire head 330 and a portion of shaft 320 of first fastener 310 and/or shaft 370 of second fastener 350 are positioned and reside outside the bone(s) in which first fastener 310 and second fastener 350 are inserted. By positioning head 330 outside the vertebrae, bone fixation system 300 is configured to aid in the fusion of multi-levels of vertebrae. For example, head 330 positioned outside the vertebrae allows for a wider range of angular relationship between first fastener 310 and second fastener 350 for fastening to adjacent vertebrae or vertebrae spaced farther up or down the spine from each other.

Figure 21:
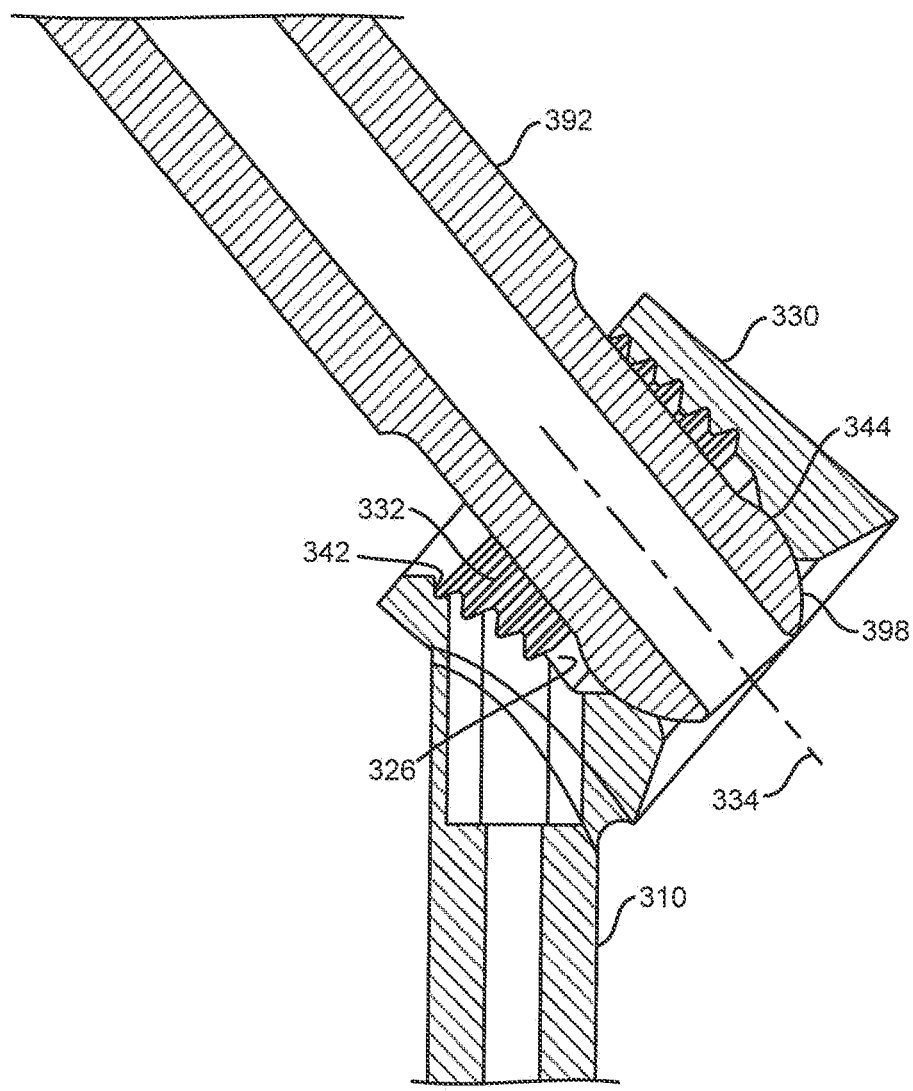
FIG. 21 illustrates a partial cross-sectional view of the embodiment of the drill guide of FIG. 20 for use with the bone fixation system of FIG. 14, in accordance with one or more aspects of the present invention.
Figure 22A:
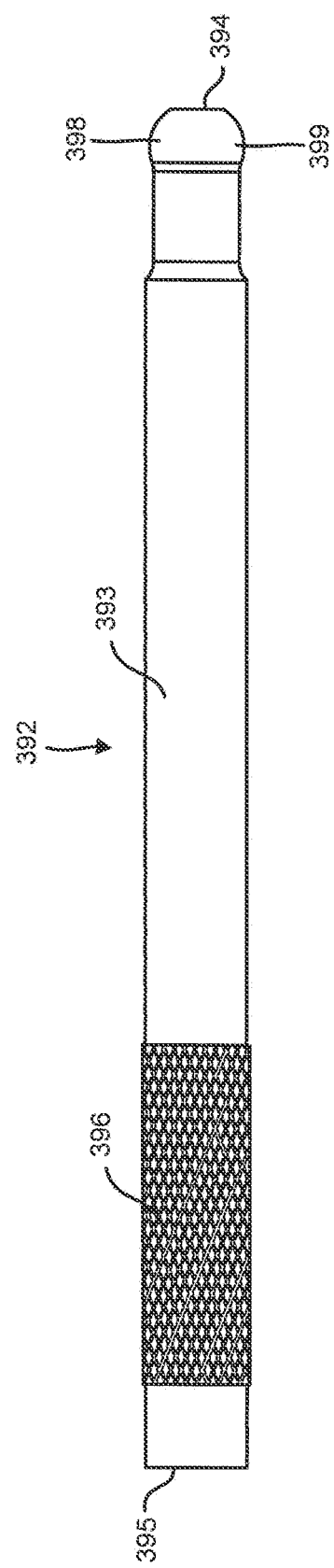
FIG. 22A illustrates a side view of the drill guide FIG. 20, in accordance with one or more aspects of the present invention.
Figure 22B:
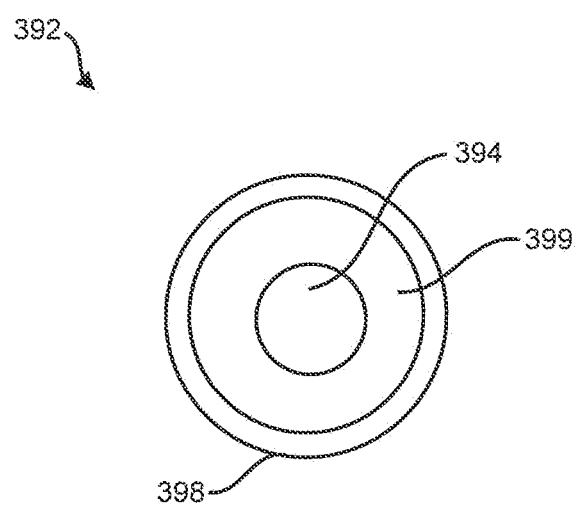
FIG. 22B illustrates a top view of the drill guide of FIG. 20, in accordance with one or more aspects of the present invention.
Figure 22C:
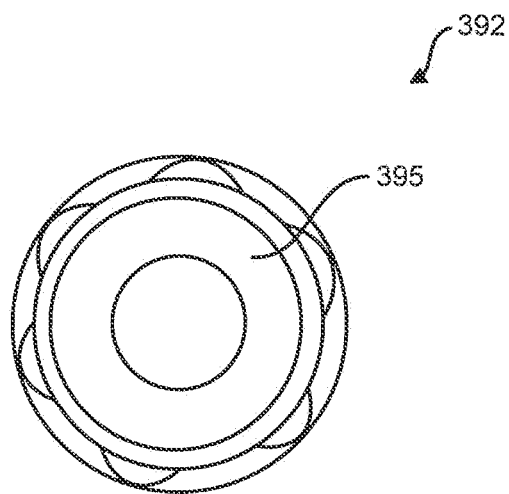
FIG. 22C illustrates a bottom view of the drill guide of FIG. 20, in accordance with one or more aspects of the present invention.
Figure 22D:
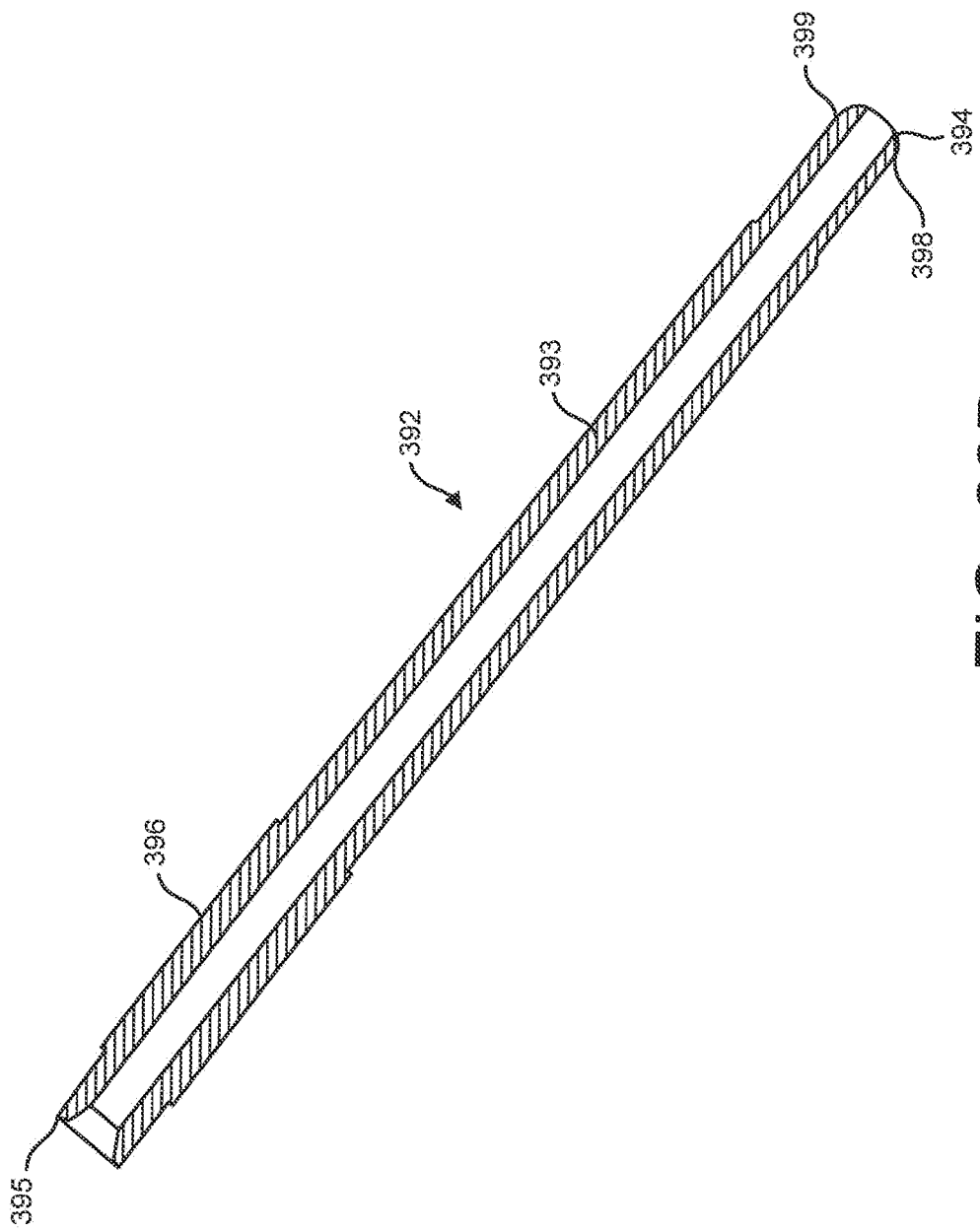
FIG. 22D illustrates a cross-sectional view of the drill guide of FIG. 20, in accordance with one or more aspects of the present invention.
Figure 23:
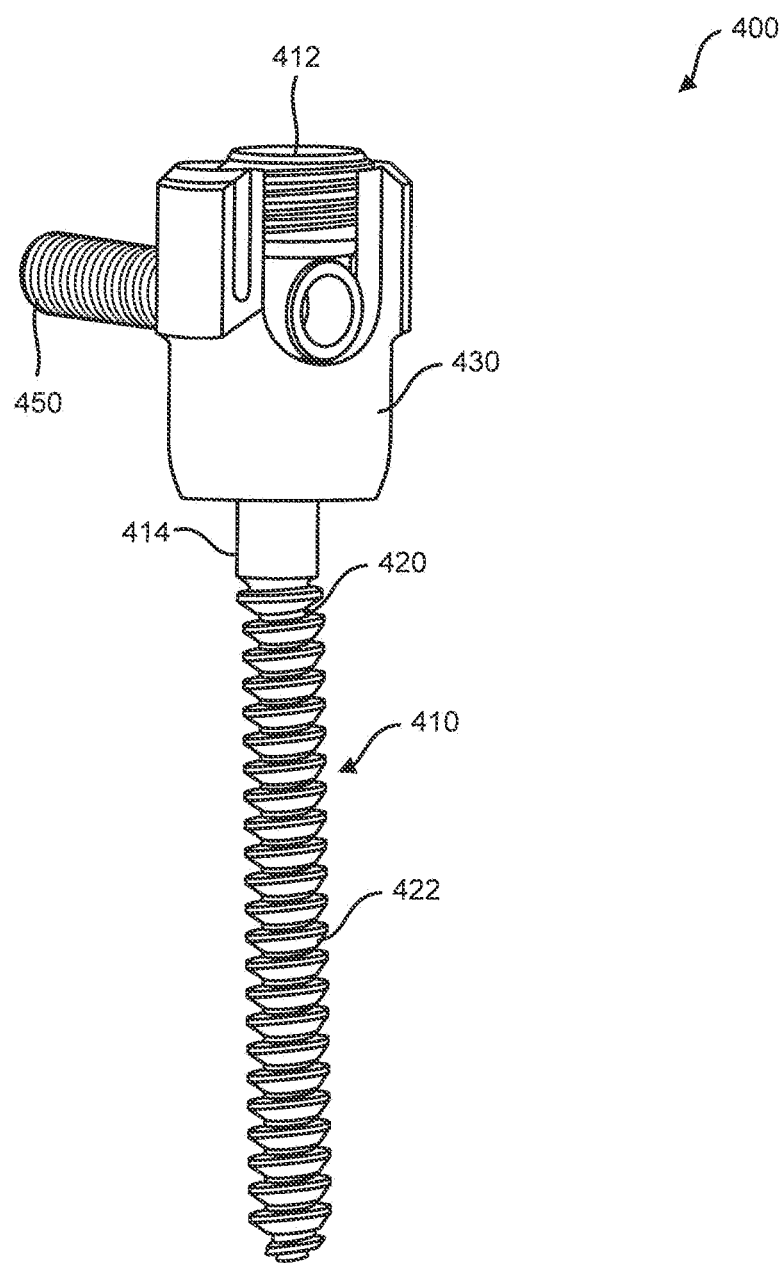
FIG. 23 illustrates a perspective view of another embodiment of a bone fixation system, in accordance with one or more aspects of the present invention.
Figure 24:
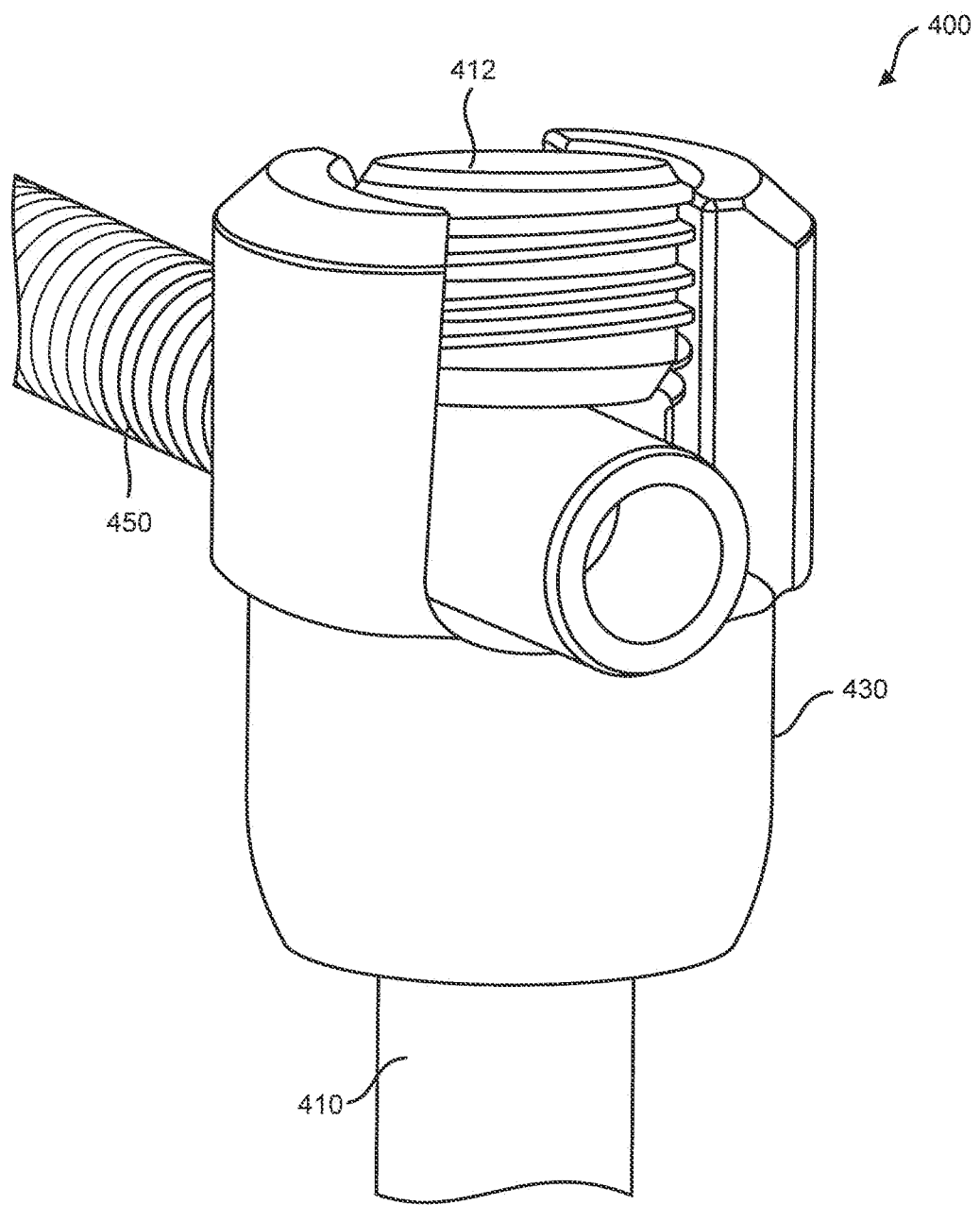
FIG. 24 illustrates a partial perspective view of the bone fixation system shown in FIG. 23, in accordance with one or more aspects of the present invention.
Figure 25:
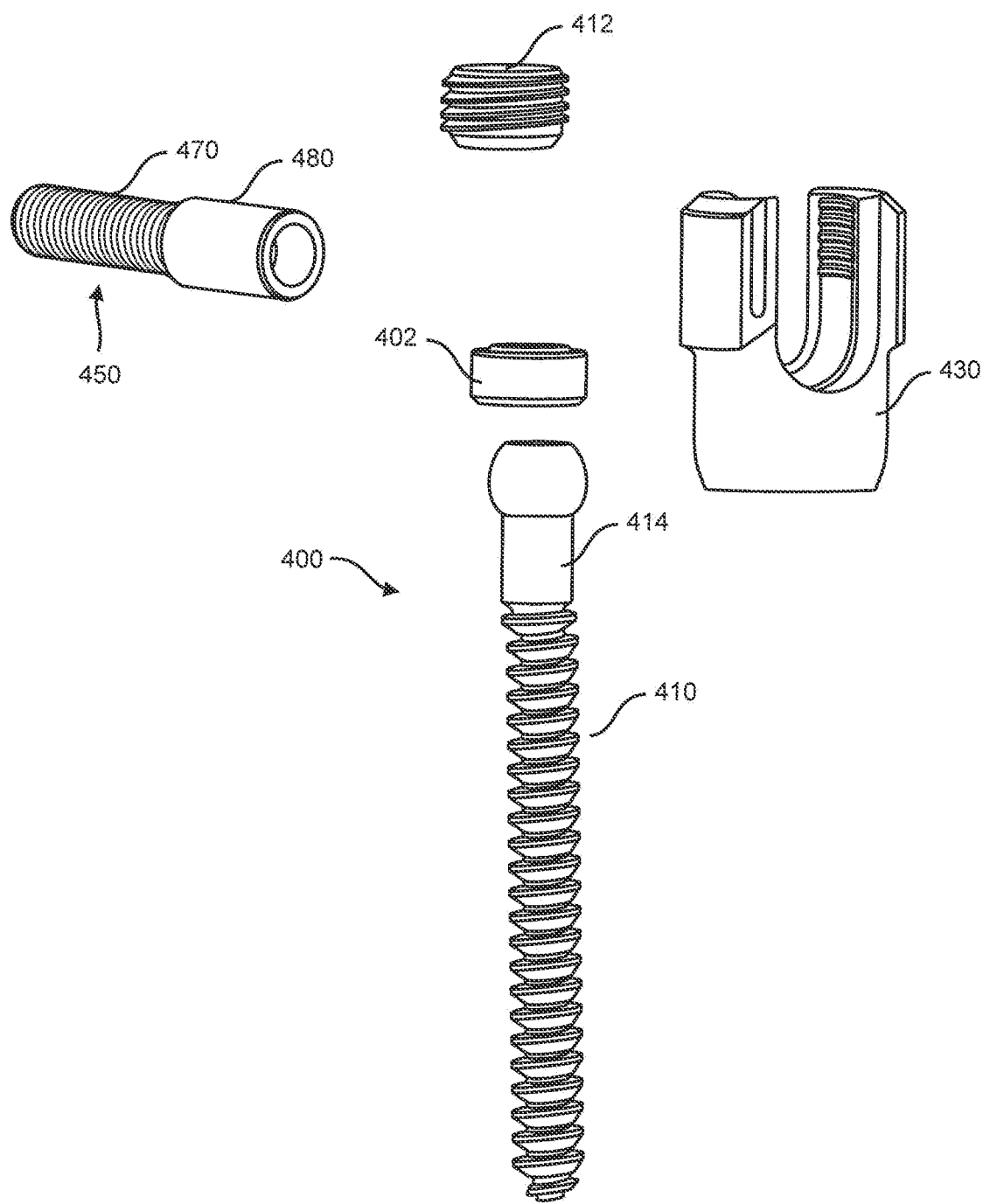
FIG. 25 illustrates an exploded view of the bone fixation system shown in FIG. 23, in accordance with one or more aspects of the present invention.

Prior to insertion of second fastener 350 through first fastener 310 and into a second desired bone, an angle guide may be used to select the appropriate angle of second fastener 350 with respect to first fastener 310. FIGS. 20-22D illustrate one embodiment of an angle guide that may be used in system 300. As illustrated in FIGS. 22A-22D, angle guide 392 may include a hollow elongated shaft 393 having a first end 394, a second end 395, a handle portion 396 proximate second end 395 and a head 398 at first end 394. Head 398 includes an exterior surface 399. Exterior surface 399 may be configured, sized and shaped to engage at least a portion of seat 344 of interior surface 336 of head 330 of first fastener 310. As illustrated in FIG. 21, head 398 of angle guide 392 is received by and inserted into passageway 332 until exterior surface 399 engages seat 344 to then allow a drill to be used to pre-drill a hole prior to insertion of second fastener 350. Exterior surface 399 may include a mating bulbous configuration to seat 344, matching, in one example, bulbous portion of exterior surface 390 of head 380 of second fastener 350, to allow angular positioning of angle guide 392 within passageway 332 of head 330. In this example, a surgeon may be able to position angle guide 392 at a desired angle relative to longitudinal axis 334 of head 330.

In one example, system 300 may be inserted into the spine of a patient. System 300 may be implanted by first preparing a patient's vertebrae for insertion of the bone fixation system 300. With a patient in the prone position, a surgeon may make an incision approximately 2 cm to midline. Next, the proper location and orientation of first or primary fastener 310 is determined. Using an A/P fluoroscopy, the cephalad pedicle is identified. A Jamshidi needle may then be placed through the soft tissues so that the tip is in the middle of the cephalad pedicle. Next, the Jamshidi needle is then positioned so that a "bullseye" image is seen on A/P fluoroscopy, guaranteeing a direct trajectory into the pedicle. A K-wire is then placed through the Jamshidi approximately 1 cm into the facet boney structure. The use of a K-wire technique via Jamshidis and cannulated screws ensures correct trajectories prior to insertion of the first and second fasteners without the need for image guidance, thereby improving safety while decreasing cost.

Fluoroscopy is then placed into the lateral position to conform that the trajectory is appropriate. The Jamshidi is removed and the K-wire is advanced through the pedicle into the vertebral body. Next, over the K-wire, a "pilot" hole is created using a tap. A cannulated screw driver tool is engaged with engagement opening 324 of first fastener 310. First fastener 310 (with the cannulated screw driver tool) is then placed over the K-wire and first fastener 310 is inserted or screwed into the cephalad pedicle. The K-wire is then removed and the position of first or primary fastener 310 is confirmed with lateral fluoroscopy. After first fastener 310 is properly located, the cannulated screw driver tool is removed.

Next, the area is prepared for insertion of second or secondary fastener 350. First, head 398 of angle guide 392 is inserted into passageway 330 of head 330 of first fastener 310. A Jamshidi needle is then placed through angle guide 392. Using lateral fluoroscopy, the proper and appropriate trajectory for second fastener 350 to intersect the caudal pedicle is determined. When the proper location is determined, the surgeon gently taps the Jamshidi needle into the bone to secure the appropriate position. Next, a K-wire is placed through the Jamshidi needle and the trajectory is confirmed though lateral and A/P Fluoroscopy. Under lateral fluoroscopy, the K-wire is advanced into the caudal pedicle, and the Jamshidi needle and angle guide 392 are removed. After angle guide 392 is removed, a pilot hole is drilled using a cannulated drill bit over the K-wire. Them, a surgeon will confirm position on lateral and A/P Fluoroscopy before removing the K-wire.

Next, a cannulated screw driver tool engages tool engagement opening 383 of second fastener 350. Second fastener 350 is then advanced over the K-wire to the desired depth until head 380 fully seats onto seat 344 formed in interior surface 336 of passageway 332 of head 330 of first fastener 310. The placement of second fastener 350 is then verified using lateral fluoroscopy. Next, a surgeon uses a cannulated screw driver tool to engage tool engagement opening 316 of set screw 314. Set screw 314 (with the cannulated screw driver tool) is placed over the same K-wire and inserted or screwed into head 330 of first fastener 310 until bottom surface 319 of set screw 314 contacts head 380 of first fastener 310 and secures head 380 against seat 344. Next, the final placement of system 300 is confirmed using A/P and lateral fluoroscopy and then the K-wire is removed. Finally, the patient's incision may be closed.

Figure 19A:
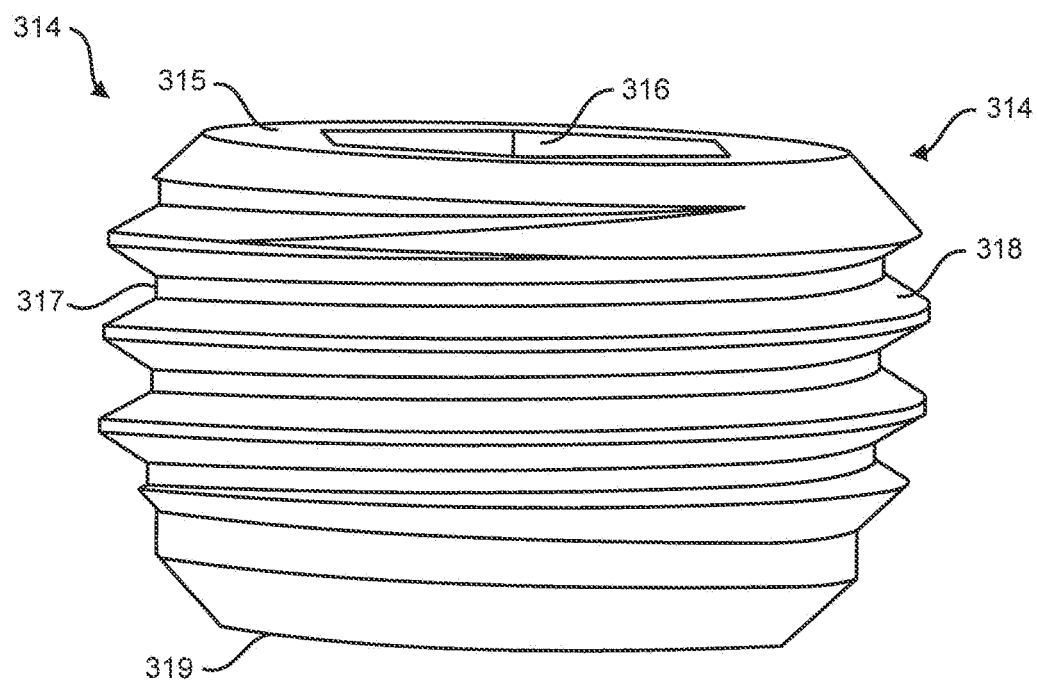
FIG. 19A illustrates a perspective view of one embodiment of a set screw of the bone fixation system of FIG. 14, in accordance with one or more aspects of the present invention.
Figure 19B:
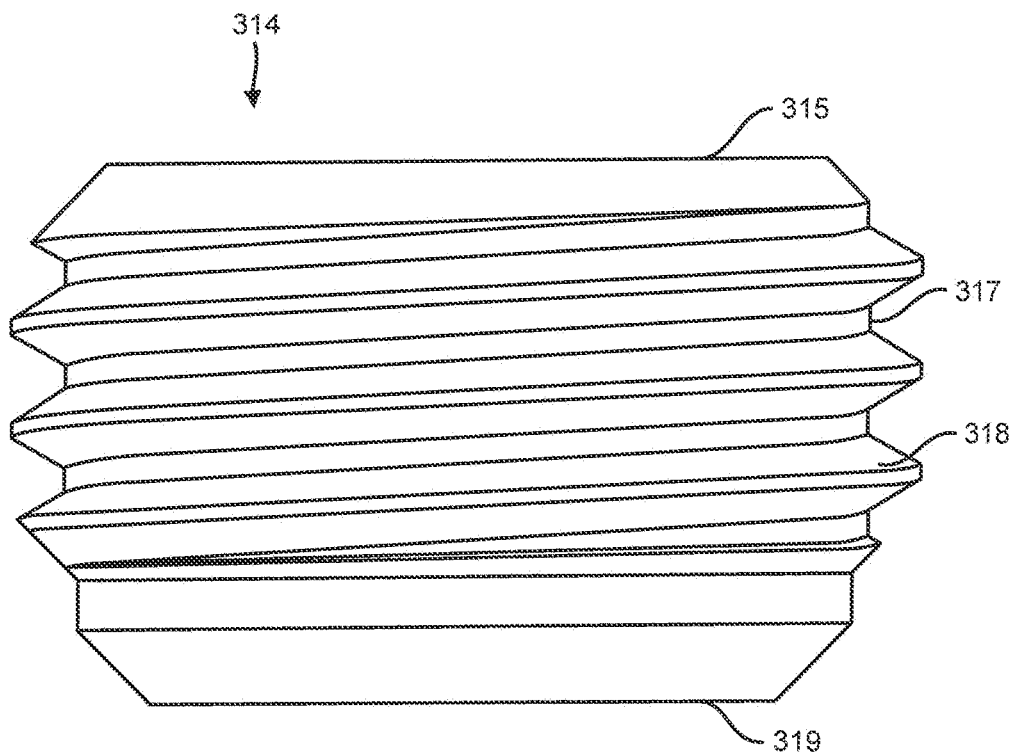
FIG. 19B illustrates a side view of the set screw of FIG. 19A, in accordance with one or more aspects of the present invention.
Figure 19C:
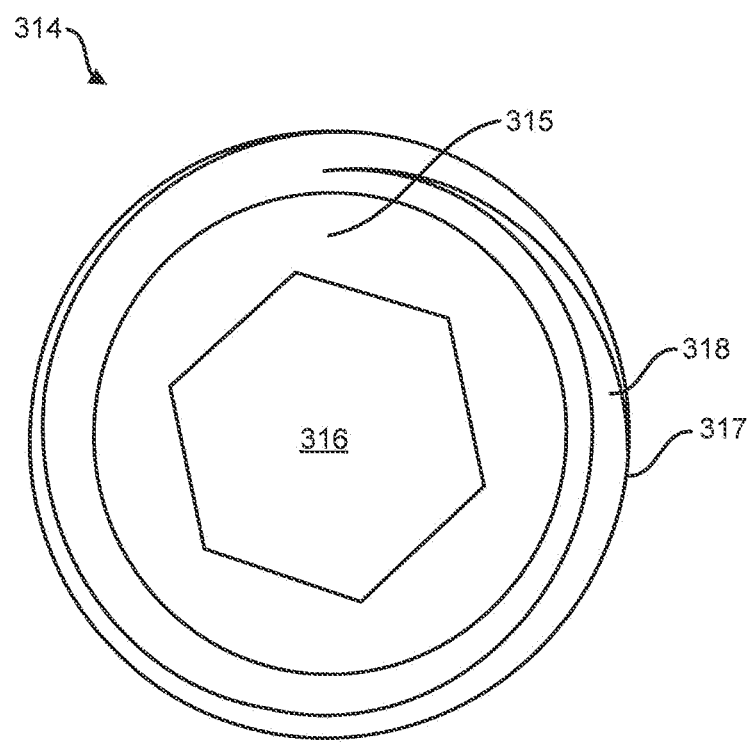
FIG. 19C illustrates a top view of the set screw of FIG. 19A, in accordance with one or more aspects of the present invention.
Figure 19D:
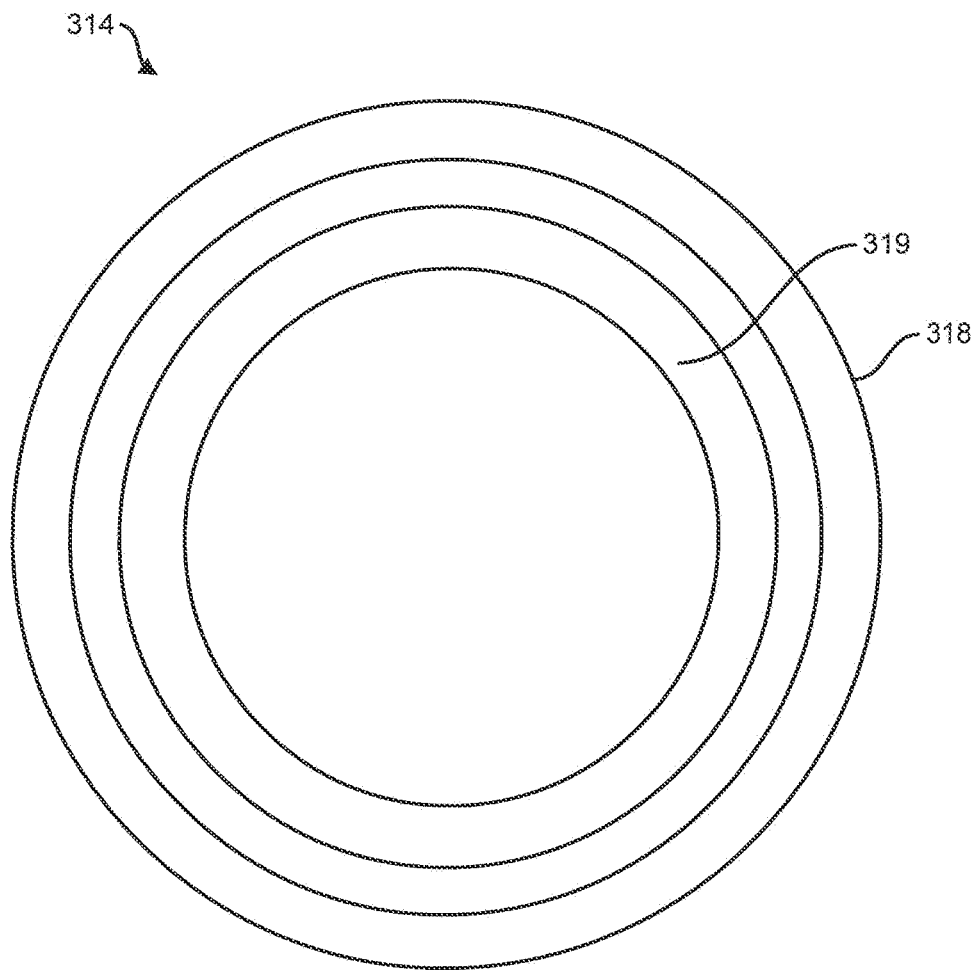
FIG. 19D illustrates a bottom view of the set screw of FIG. 19A, in accordance with one or more aspects of the present invention.
Figure 20:
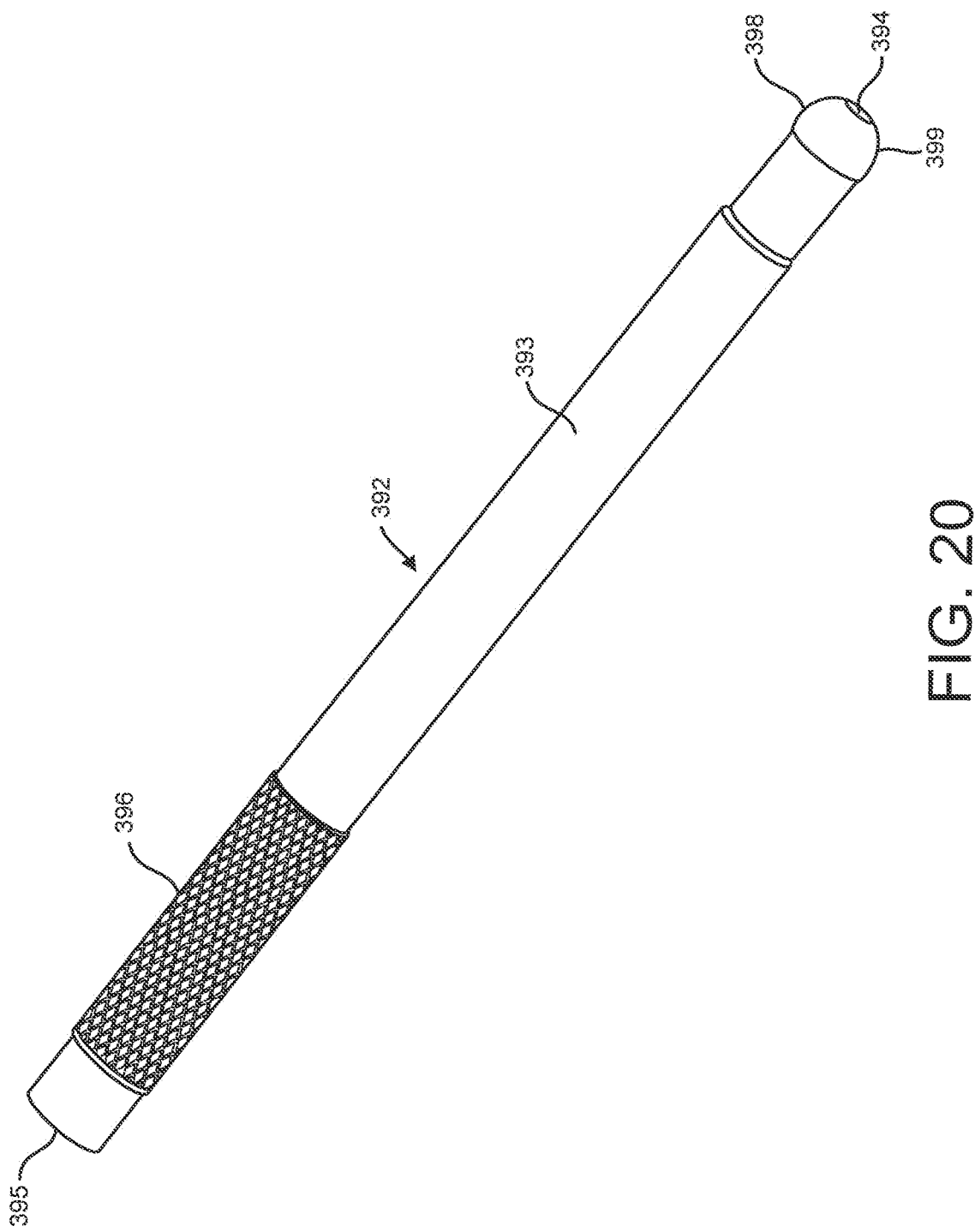
FIG. 20 illustrates a perspective view of one embodiment of a drill guide for use with the bone fixation system of FIG. 14, in accordance with one or more aspects of the present invention.

In the system 300 illustrated in FIGS. 19-19D, second fastener 350 may be of fixed orientation or be orientated in various angles relative to first fastener 110 depending on the designed embodiment. The specific angle configuration of second fastener 350 relative to first fastener 310 is locked into place by set screw 314 within passageway 332. In one example, system 300 may have the ability to angulate second fastener 350 approximately twelve degrees in any direction on spherical or bulbous head 380 relative to axis 334 of first fastener 310 that is necessary when a Jamshidi needle or K-wire is inserted through second fastener 350. Without a needle or K-wire insert through second fastener 350, system 300 may have the ability to angulate second fastener 350 up to approximately forty degrees relative to axis 334 of first fastener 310. In one example, the angle configuration of longitudinal axis 321 of first fastener 310 relative to longitudinal axis 362 of second fastener 350 ranges between approximately thirty-three degrees to approximately sixty-seven degrees. In another example, when longitudinal axis 362 of second fastener 350 is aligned with axis 334 of head 340, the angle between longitudinal axis 321 of first fastener 310 relative to longitudinal axis 362 of second fastener 350 is approximately fifty degrees.

Another embodiment of a bone fixation system 400 is shown in FIGS. 23-30D. Bone fixation system 400 may include a first fastener 410 for anchoring into, for example, a first vertebrae, a second fastener 450 for anchoring into, for example, a second vertebrae, a head 430, a spacer 402 and a set screw or locking cap 412.

As shown in FIGS. 27A-27D, first fastener 410 may include a shaft 420, a head 425 and a longitudinal axis 421. Shaft 420 may include a neck 414 connecting shaft 420 to the head 425. Shaft 420 includes an outer surface 414. Shaft 420 may include one or more bone engagement mechanisms 422 on at least a portion of outer surface 414 to facilitate a gripping engagement of first bone anchor to bone. In one example illustrated in FIG. 27A, shaft 420 may be, for example, threaded along its entire length, threaded along only a portion of the length, or non-threaded. In the illustrated embodiment, the external thread is a single lead thread that extend from a distal tip of the shaft to the proximal head portion. Other suitable bone engagement mechanisms may include, but are not limited to, one or more annular ridges, multiple threads, dual lead threads, variable pitched threads, longitudinal splines or other geometries, and/or any conventional bone engagement mechanism. Head 425 may include a top surface 426 and a side portion 427. Top surface 426 may include a tool engagement opening extending into head 424. Side portion 427 of head 425 may include an exterior surface shaped like, for example, a polyaxial screw head in the form of, for example, a bulbous head, hemispherical, or partially spherical head.

Figure 28A:
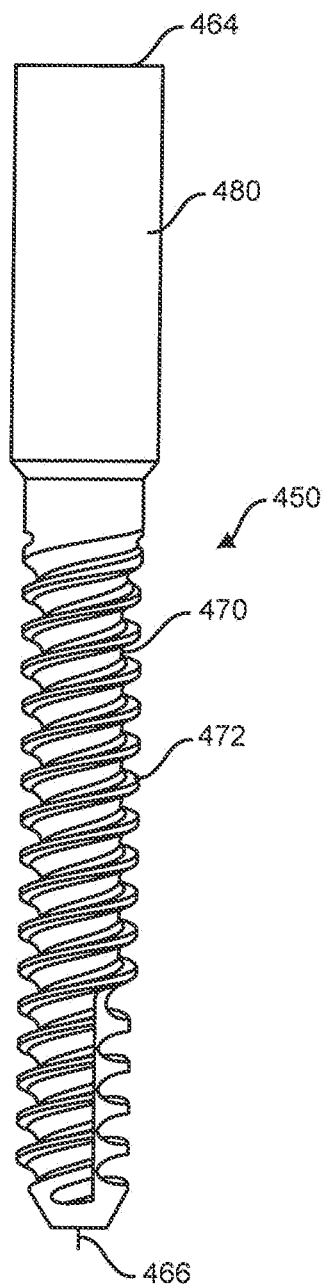
FIG. 28A illustrates a side view of one embodiment of a second fastener of the bone fixation system of FIG. 23, in accordance with one or more aspects of the present invention.
Figure 28B:
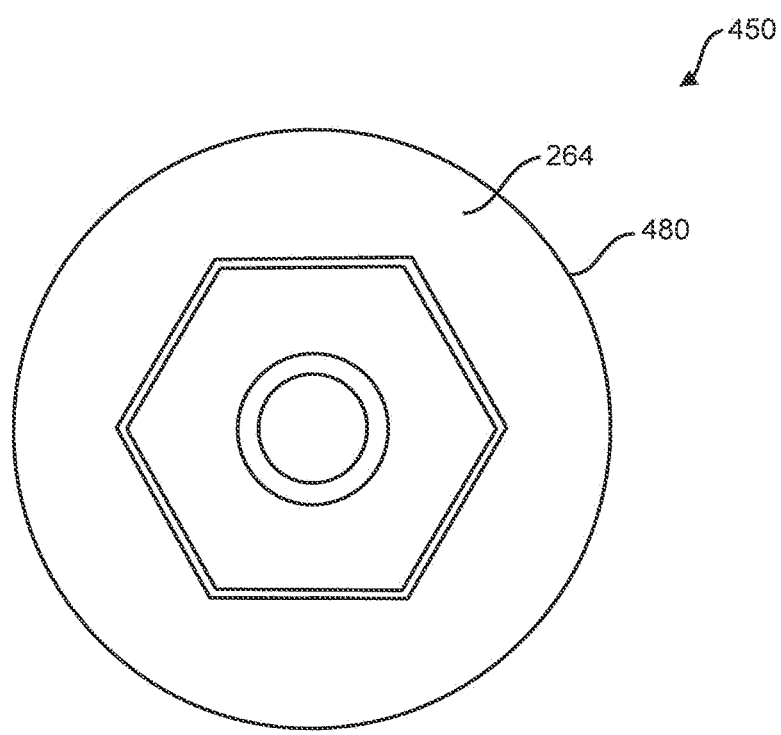
FIG. 28B illustrates a top view of the second fastener of FIG. 28A, in accordance with one or more aspects of the present invention.
Figure 28C:
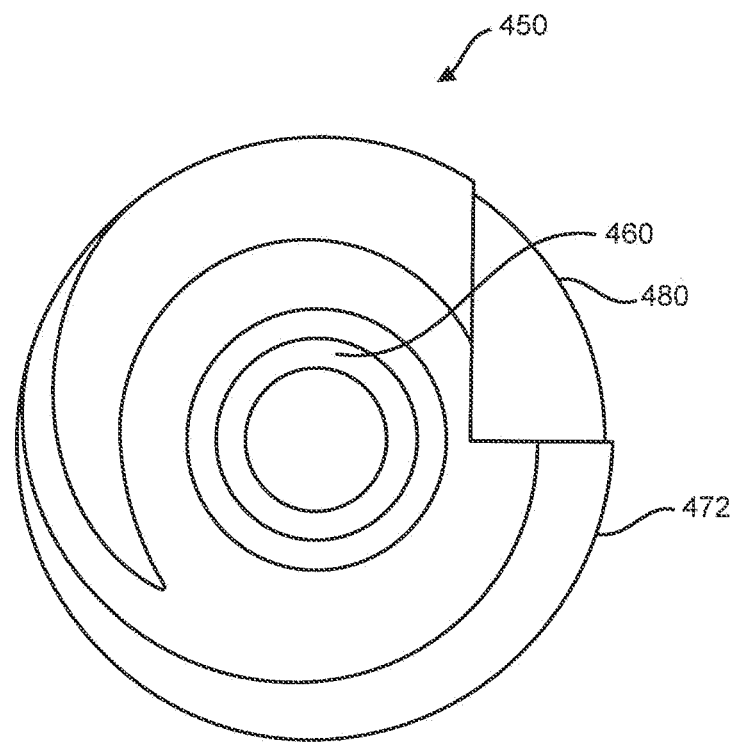
FIG. 28C illustrates a bottom view of the second fastener of FIG. 28A, in accordance with one or more aspects of the present invention.
Figure 29A:
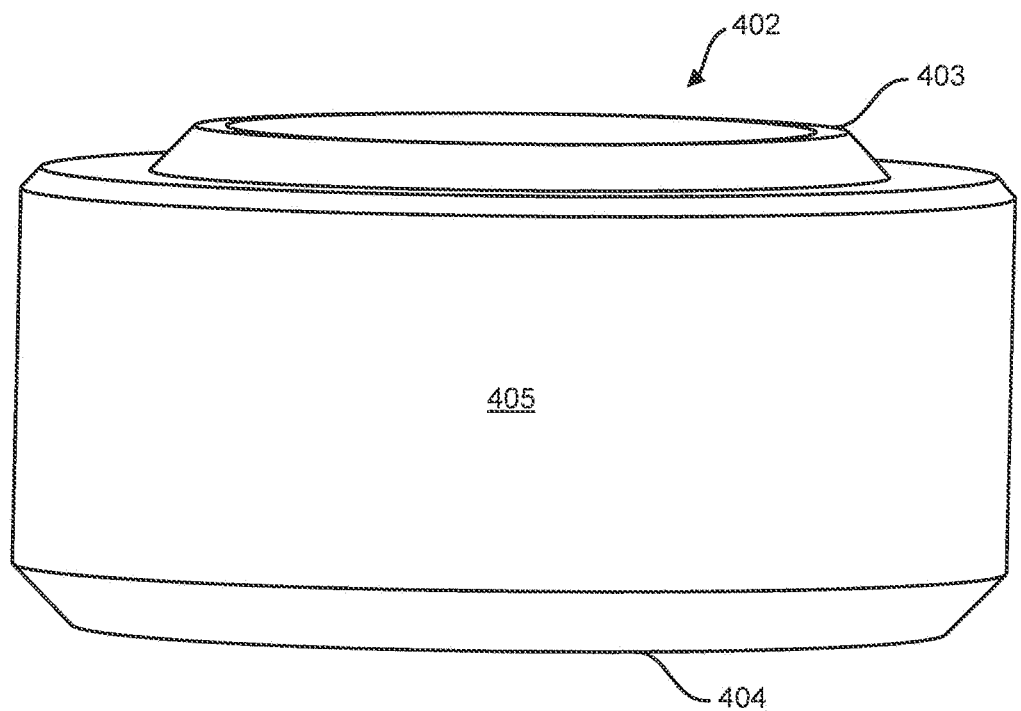
FIG. 29A illustrates a perspective view of one embodiment of a spacer of the bone fixation system of FIGS. 23-25, in accordance with one or more aspects of the present invention.
Figure 29B:
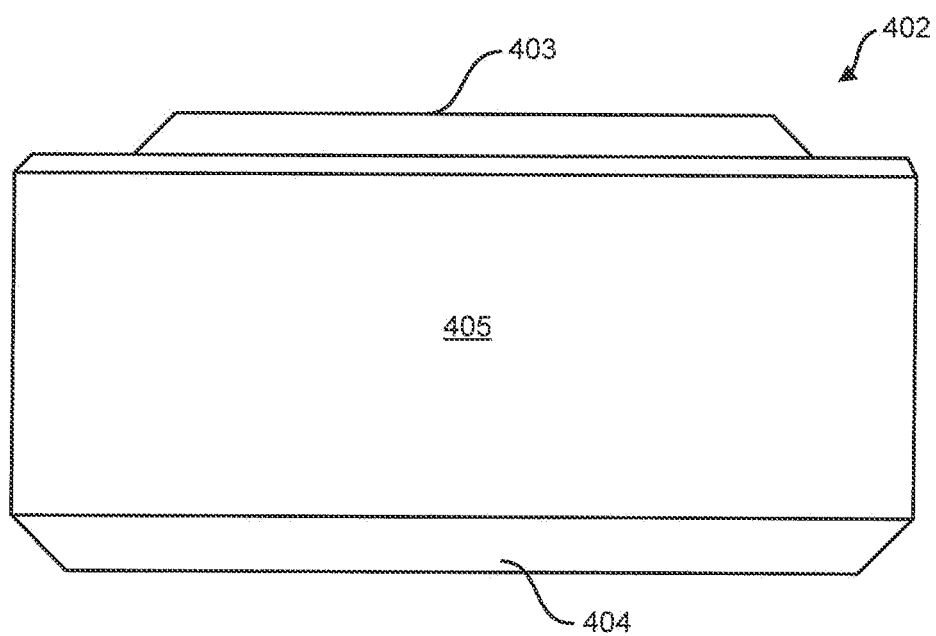
FIG. 29B illustrates a side view of the spacer of FIG. 29A, in accordance with one or more aspects of the present invention.
Figure 29C:
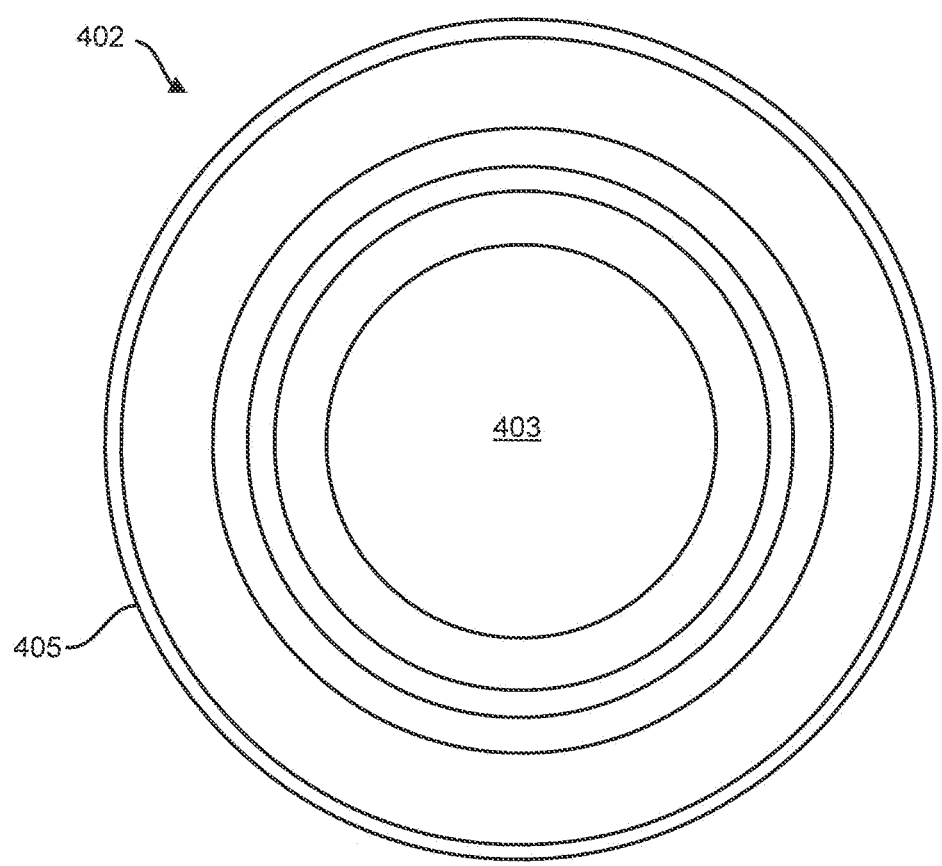
FIG. 29C illustrates a top view of the spacer of FIG. 29A, in accordance with one or more aspects of the present invention.
Figure 29D:
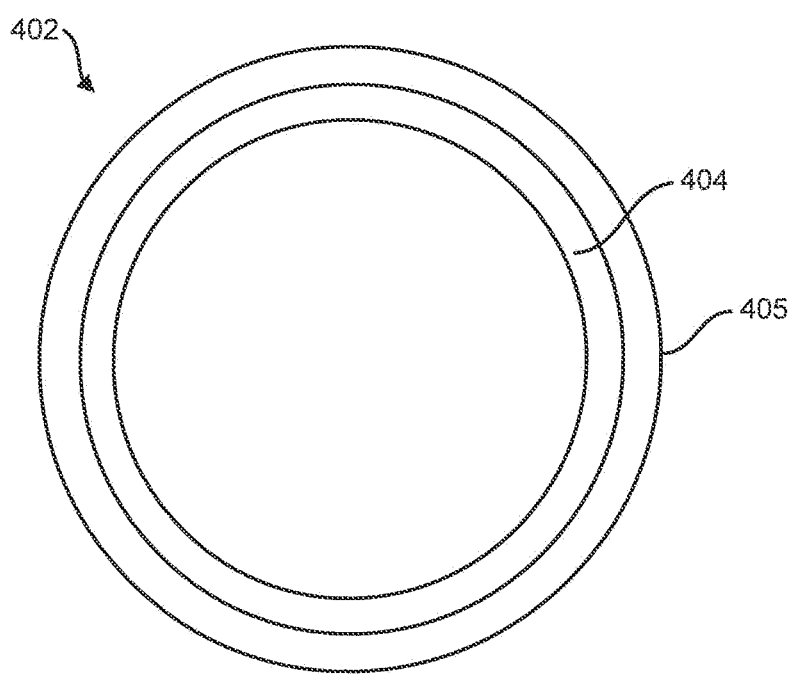
FIG. 29D illustrates a bottom view of the spacer of FIG. 29A, in accordance with one or more aspects of the present invention.
Figure 30A:
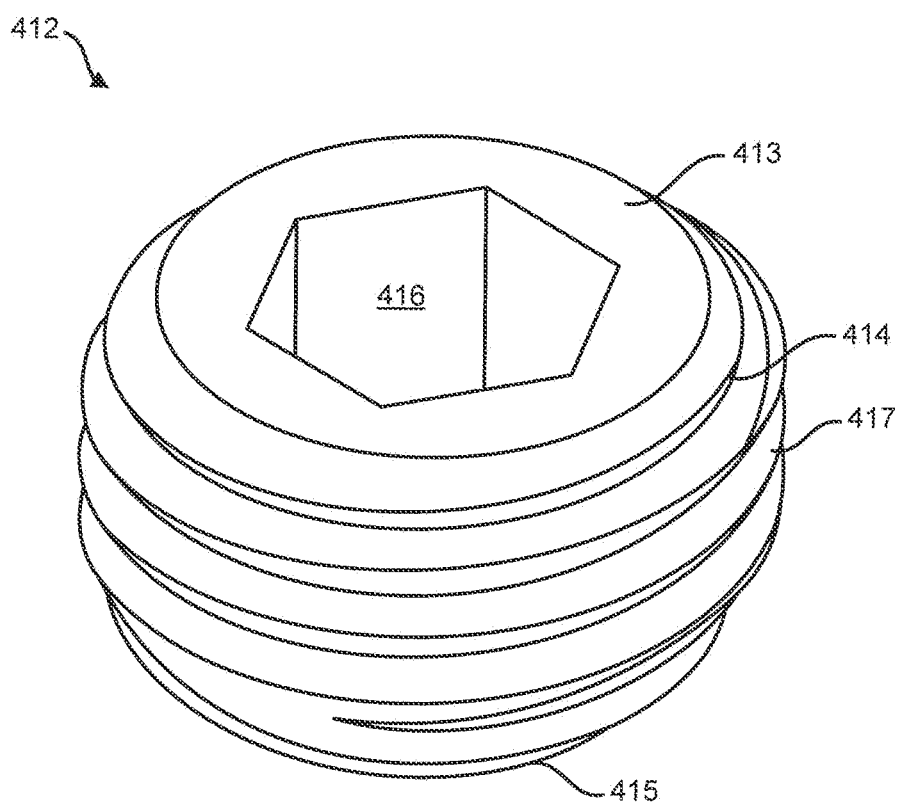
FIG. 30A illustrates a perspective view of one embodiment of a set screw of the bone fixation system of FIG. 23-25, in accordance with one or more aspects of the present invention.
Figure 30B:
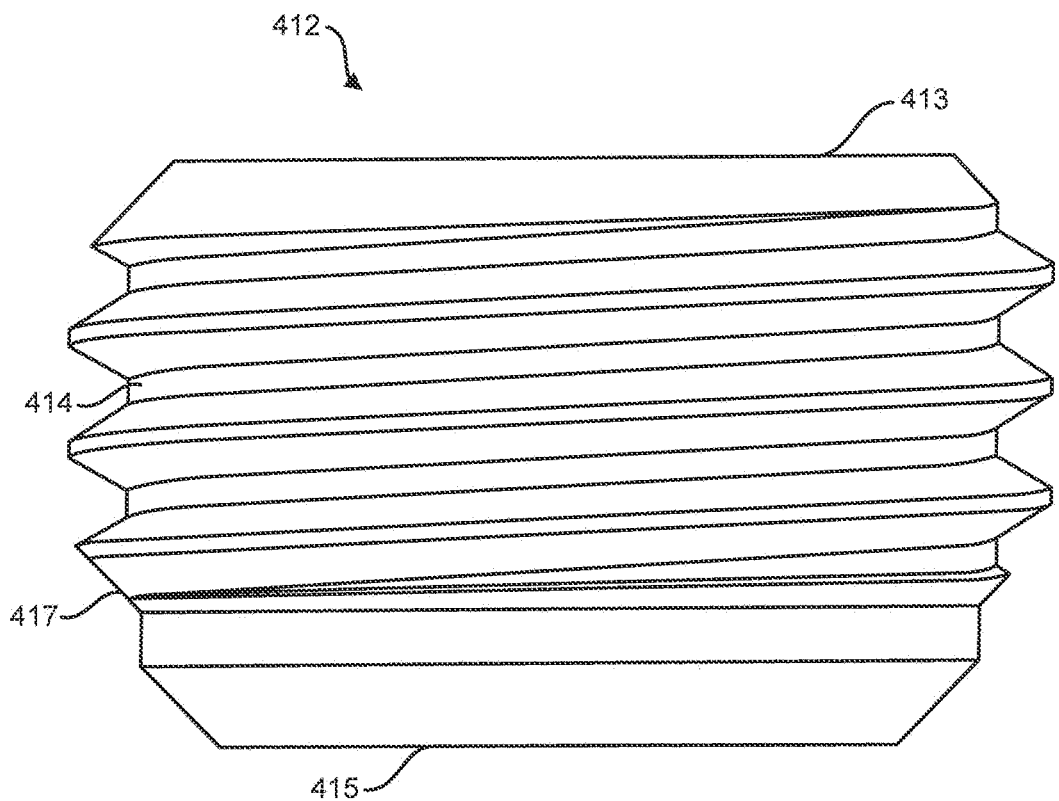
FIG. 30B illustrates a side view of the set screw of FIG. 30A, in accordance with one or more aspects of the present invention.
Figure 30C:
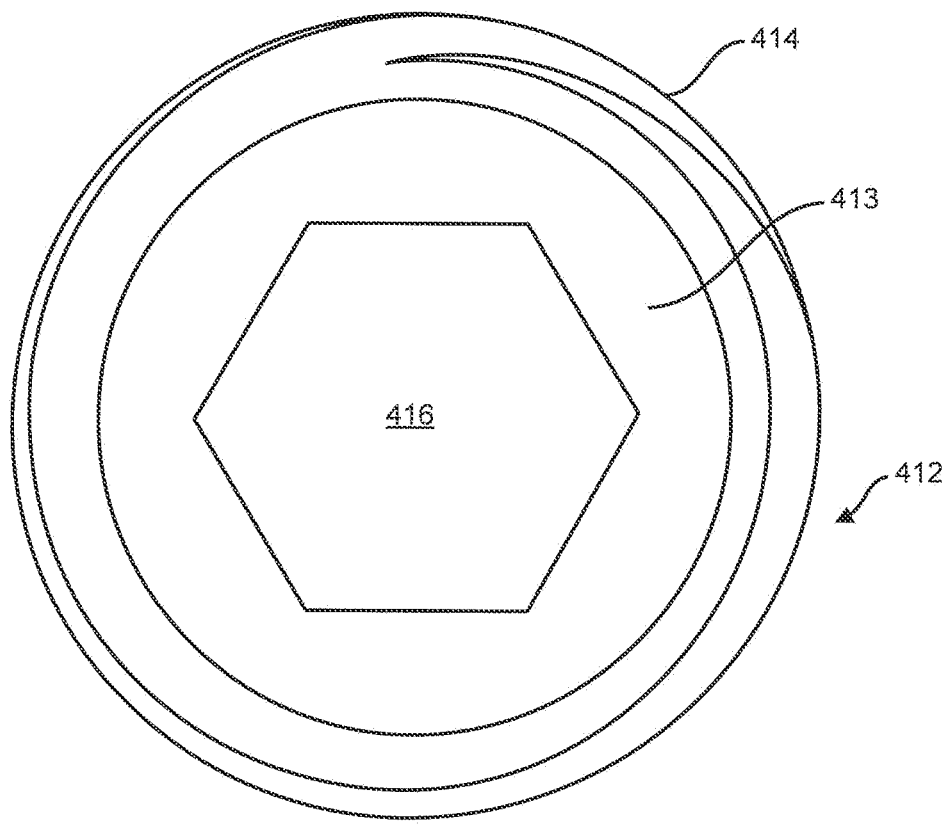
FIG. 30C illustrates a top view of the set screw of FIG. 30A, in accordance with one or more aspects of the present invention.
Figure 30D:
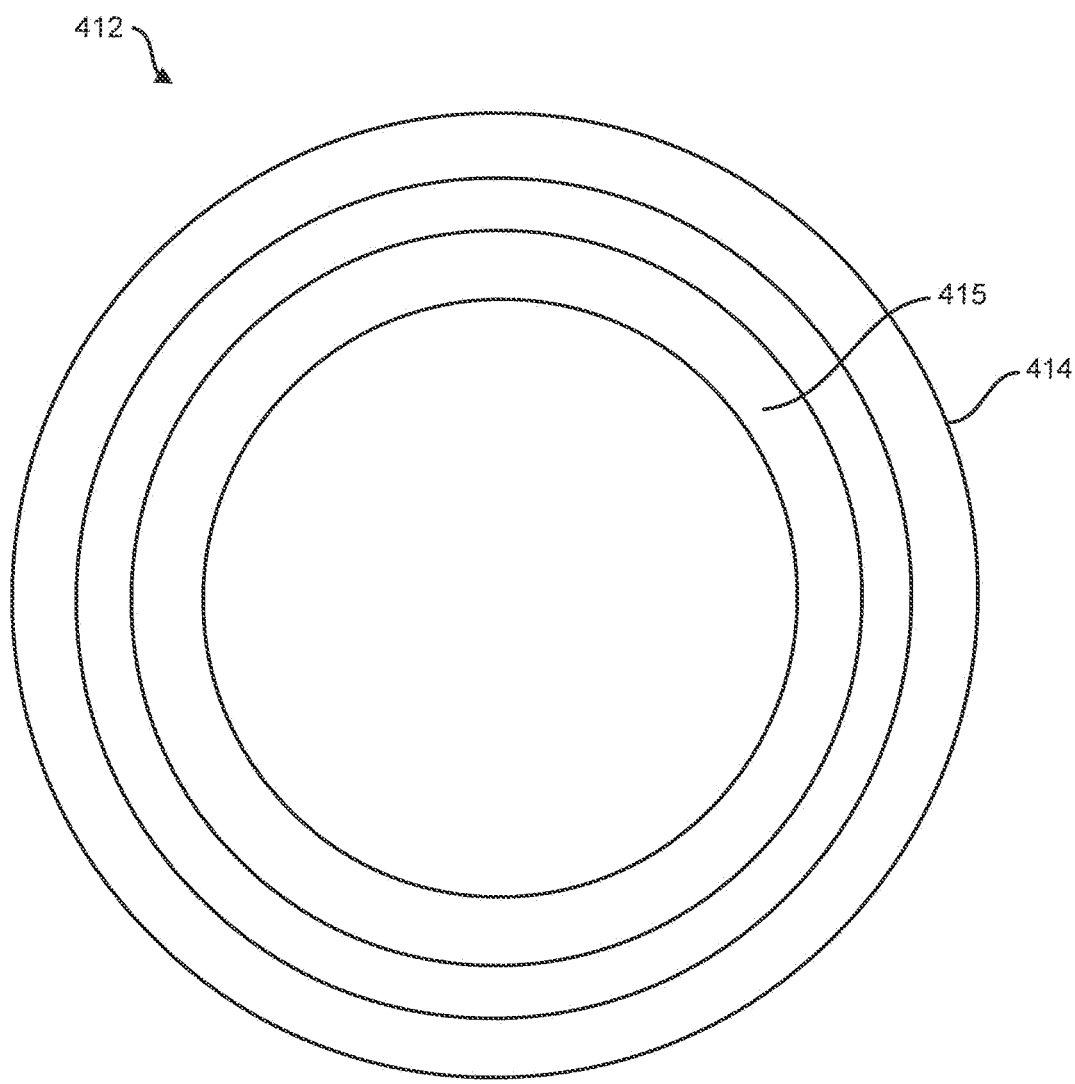
FIG. 30D illustrates a bottom view of the set screw of FIG. 30A, in accordance with one or more aspects of the present invention.

As illustrated in FIGS. 28A-28C, second fastener 450 may include a proximal end 464, a distal end 466, a shaft 470, and a head 480. Shaft 470 may include one or more bone engagement mechanisms 472 to facilitate a gripping engagement of second fastener to bone. Shaft 470 may be, for example, threaded along its entire length, threaded along only a portion of the length, or non-threaded. In the illustrated embodiment, the external thread is a single lead thread that extend from a distal tip of the shaft to the proximal head portion. Other suitable bone engagement mechanisms may include, but are not limited to, one or more annular ridges, multiple threads, dual lead threads, variable pitched threads, longitudinal splines or other geometries, and/or any conventional bone engagement mechanism.

Figure 26A:
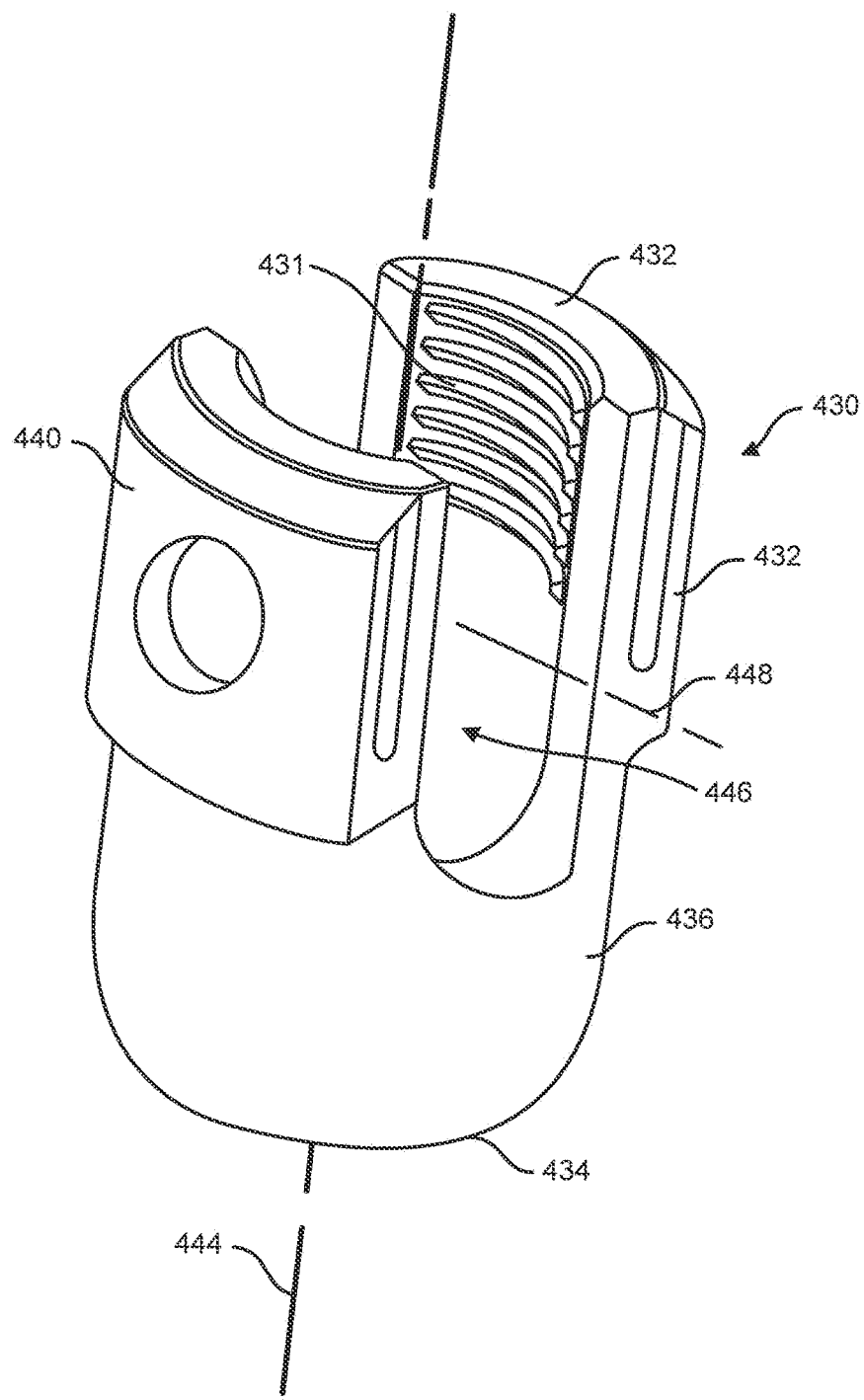
FIG. 26A illustrates one perspective view of one embodiment of a head for use with the bone fixation system of FIG. 23, in accordance with one or more aspects of the present invention.
Figure 26B:
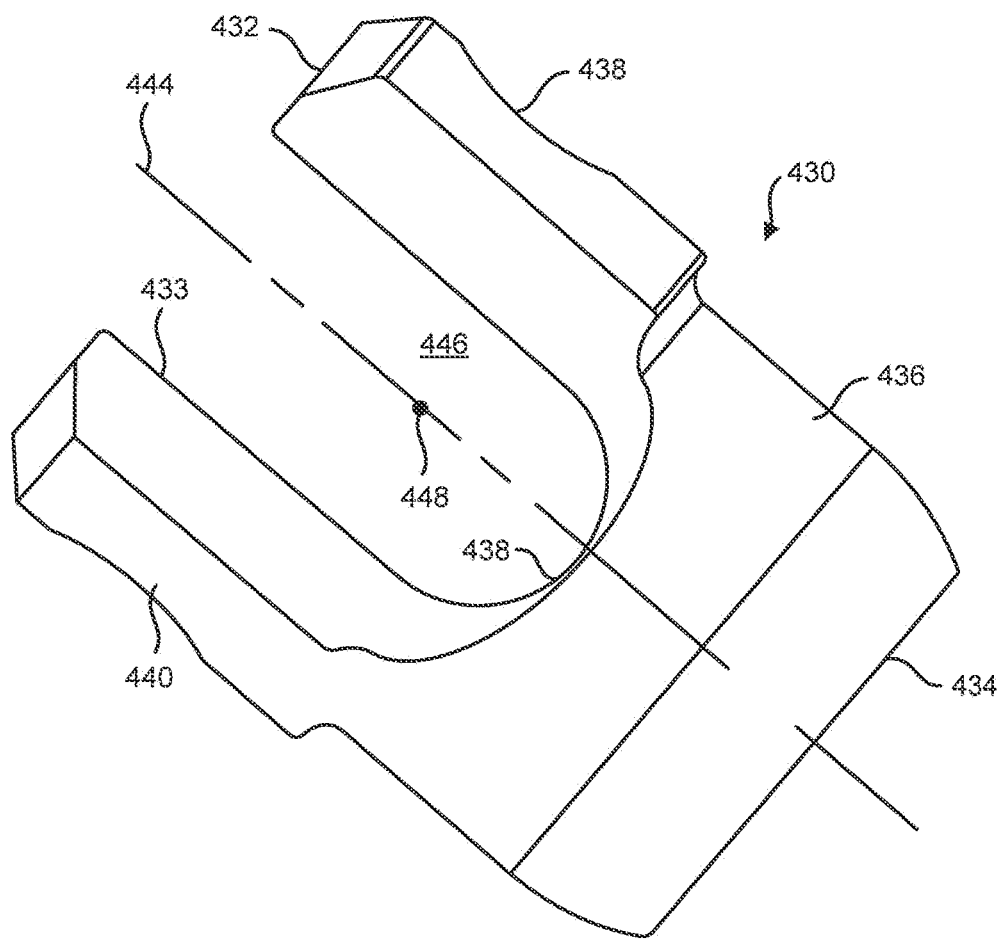
FIG. 26B illustrates a side view of the head shown of FIG. 26A, in accordance with one or more aspects of the present invention.
Figure 26C:
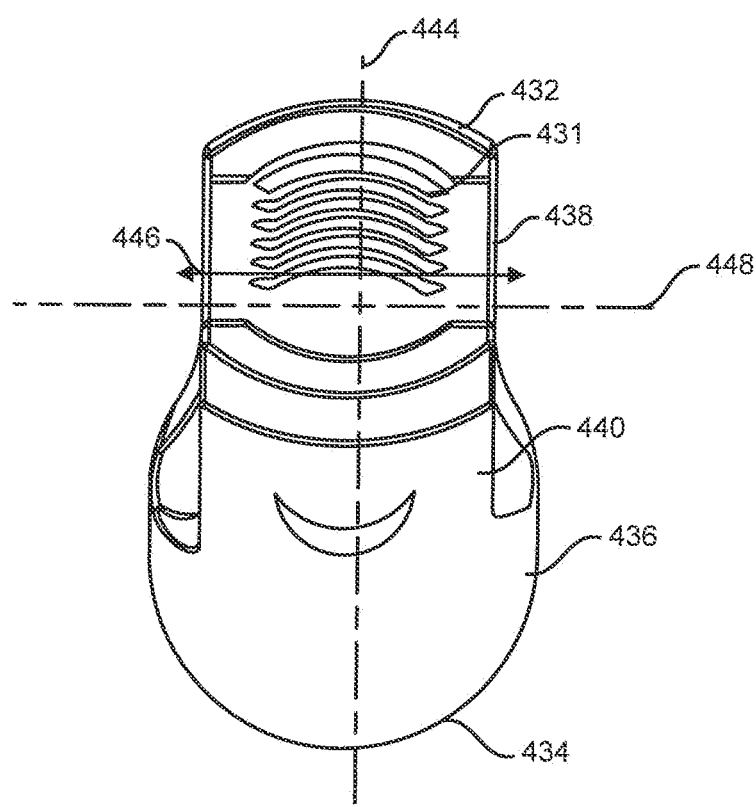
FIG. 26C illustrates another perspective view of the head shown of FIG. 26A, in accordance with one or more aspects of the present invention.

As illustrated in FIGS. 26A-26D, head 430 includes a cylindrical body 431. In one embodiment, the diameter of body 431 is greater than the diameter of shaft 420 extending to outer surface 414. Head 430 may include a top end 432, a bottom end 434, a base 436 extending from bottom end 434, and a first arm 438 and a second arm 440 extending upward from base 436 to top end 432. As illustrated in FIG. 26A, head 430 may form receiving portions for receiving both first fastener 410 and second fastener 450. Head 430 may define a first passageway 442 along axis 444 for receiving first fastener 410 and a second passageway 446 along axis 448 for receiving second fastener 450. In one example, axis 444 of first passageway 442 may be perpendicular to axis 448 of second passageway 436. In one example, first passageway 442 may be formed as a through hole extending from first end 432 to second end 434. In one embodiment, first end 432 and second end 434 extend beyond outer surface 414 of shaft 420. Second passageway 446 may be formed as a U-shaped slot or other suitable opening for receiving second fastener 450 and retaining, at least, a portion of head 480 of second fastener 450.

Figure 26D:
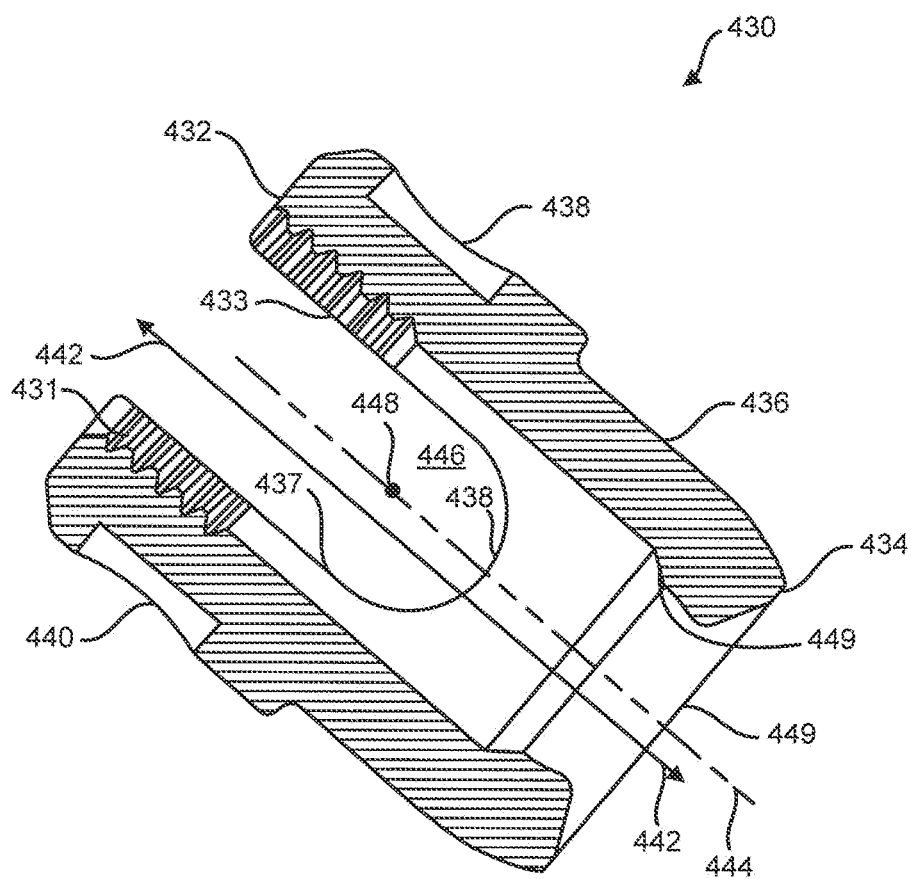
FIG. 26D illustrates a cross-sectional view of the head shown of FIG. 26A, in accordance with one or more aspects of the present invention.
Figure 27A:
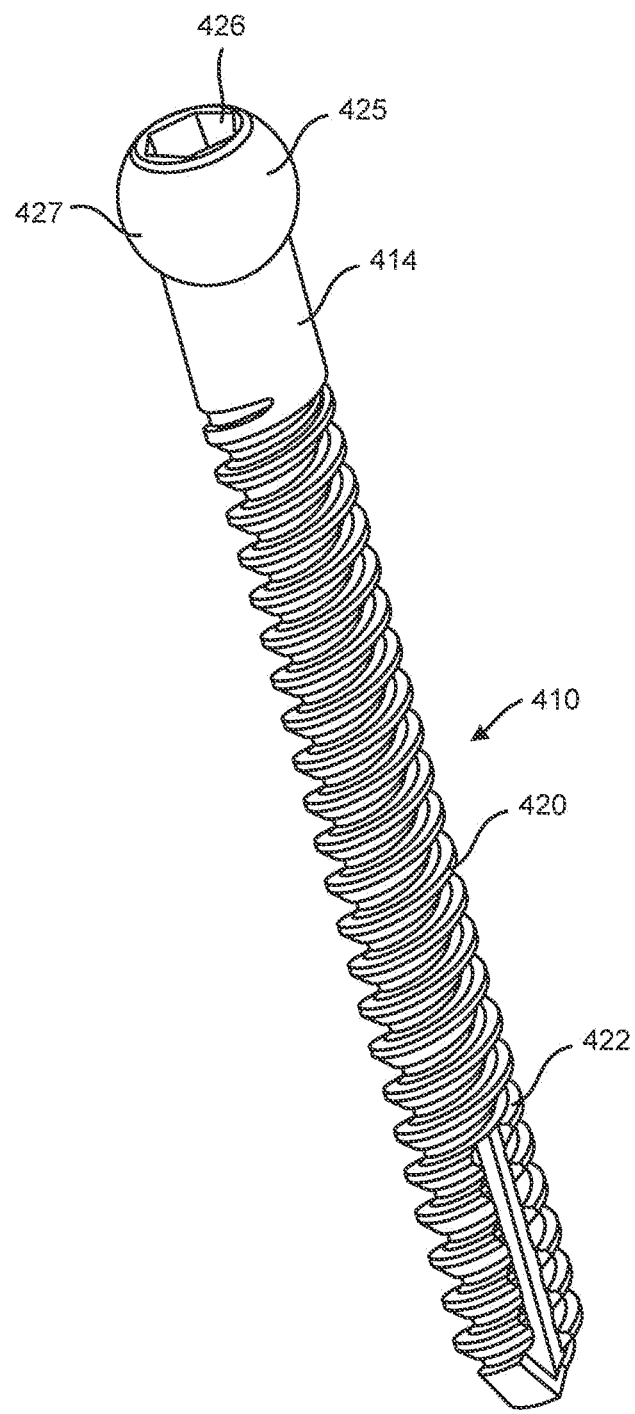
FIG. 27A illustrates a perspective view of one embodiment of a first fastener of the bone fixation system of FIG. 23, in accordance with one or more aspects of the present invention.
Figure 27B:
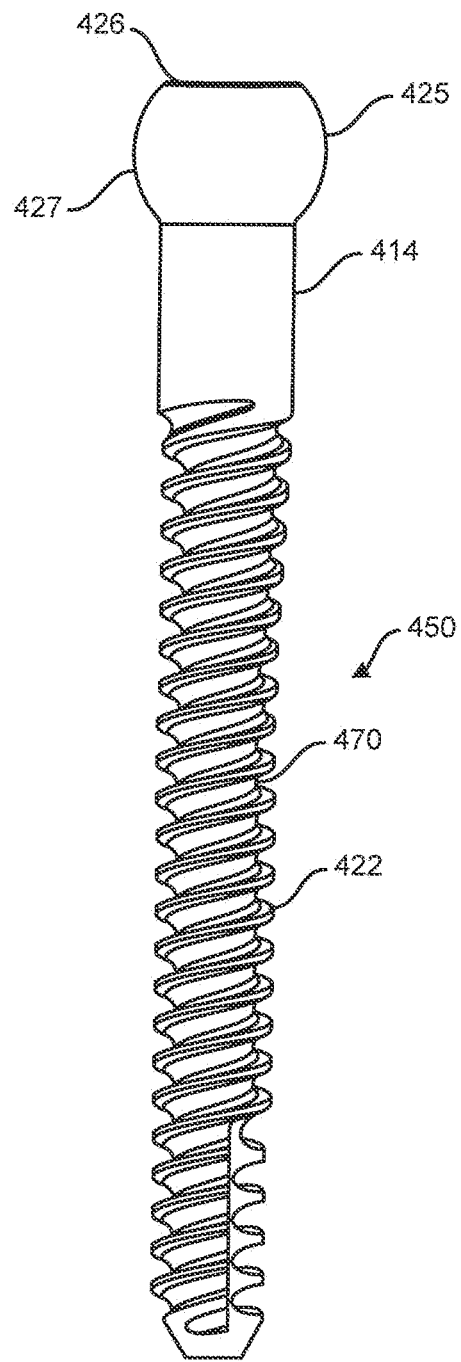
FIG. 27B illustrates a side view of the first fastener of FIG. 27A, in accordance with one or more aspects of the present invention.
Figure 27C:
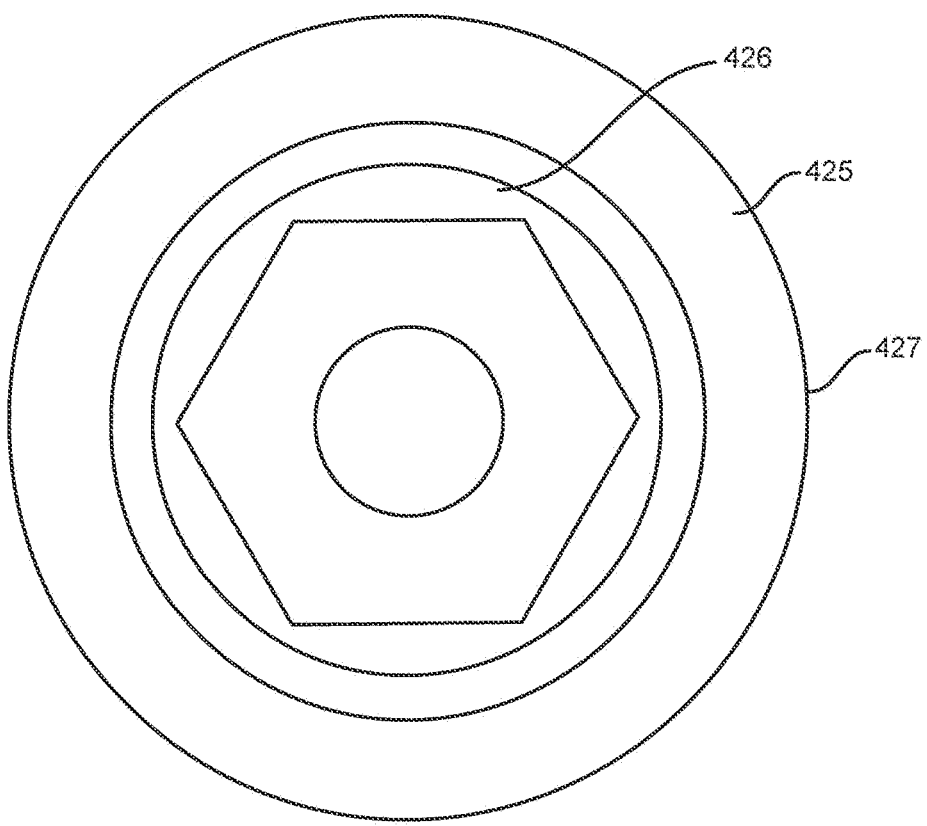
FIG. 27C illustrates a top view of the first fastener of FIG. 27A, in accordance with one or more aspects of the present invention.
Figure 27D:
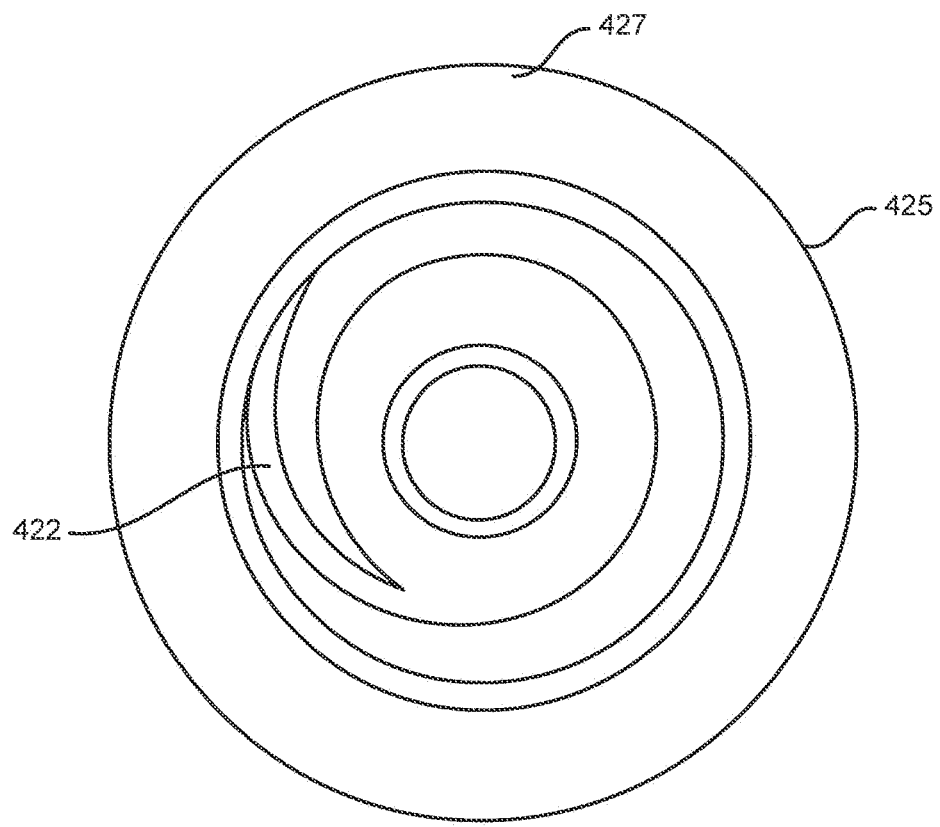
FIG. 27D illustrates a bottom view of the first fastener of FIG. 27A, in accordance with one or more aspects of the present invention.

In one example shown in FIG. 26D, U-shaped slot of a second passageway 446 includes a U-shaped interior surface 433 formed by the inner surfaces of first arm 438 and second arm 440 and a top surface 438 of base 436. This U-shaped slot may be sized and configured to receive head 480 of second fastener 450. Interior surface 433 may include, for example, a threaded portion 431 that extends along at least a portion of interior surface 433 from first end 432. Interior surface 433 may also include, for example, a non-threaded portion 437 that extends along at least a portion of interior surface 433 from first end threaded portion 431 to and including top surface 438 of base 436.

As illustrated in FIG. 26D, passageway 442 may also include a seat 449 that may extend along at least another portion of interior surface 433 within base 436 towards second end 434. In one example, seat 449 may be shaped to correspond and mate with the shape of a portion of outer surface 427 of head 425 of first fastener 410. Exterior surface 427 may be shaped to lie in or mate with seat 449 formed in interior surface of passageway 442 near second end 434. Seat 449 preferably has a shape that matches the shape of the exterior surface 427 and allows, for example, pivoting, spinning and rotation of first fastener 410 relative to axis 444. This configuration allows a range of motion along several different axes, e.g. multi-directional movement or rotation, of first fastener 410 relative to longitudinal axis 444. In this embodiment, the angulation achieved by system 400 with respect to second fastener 450 relative to first fastener 410 may be similar to that achieved by the example provided for system 300.

As illustrated in FIGS. 30A-30D, set screw or locking cap 412 may include a top surface 413, side surface 414 and a bottom surface 415. Set screw 412 may also include a tool engagement opening 416 extending into set screw 412 from top surface 213 toward bottom surface 415. In addition, set screw 412 may include threads 417 on side surface 414 extending, for example, from top surface 413 to bottom surface 415, or along a portion thereof. Bottom surface 415 may be sized and shaped to engage at least a portion of the side surface of head 480 of second fastener 450. Threads 417 are sized and configured to engage threaded portion 431 that extends along at least a portion of interior surface 433 from first end 432 of head 430.

As illustrated in FIGS. 29A-29D, spacer 402 includes a top surface 403, a bottom surface 404 and a side surface 405. Spacer 402 is sized and configured to be disposed between top surface 426 of first fastener 410 and the side surface of head 480 of second fastener 450.

The system 400 may be implanted by first preparing a patient's vertebrae for insertion of the bone fixation system 400. Next, a surgeon obtains a first fastener 410 and head 430. First fastener 410 is inserted through first passageway 442 until head 425 of first fastener 410 engages seat 449 within base 436 of head 430. First fastener 410 is then inserted into bone in a selected direction and orientation. Next, spacer 402 is positioned onto of top surface 426 of first fastener 410. Then, second fastener 450 is inserted through second passageway 446 and positioned into bone in a selected direction and orientation relative to first fastener 410. Second fastener 450 is locked into place by set screw 412. Head 480 of second fastener 450 is locked between bottom surface 415 of set screw 412 and top surface 403 of spacer 402 as set screw 412 is screwed into passageway 442. As set screw 412 is screwed down onto the side surface of head 480, first fastener 410 is also being set into place through the force translated through the contact of spacer 402 with the side surface of head 480 of second fastener 450 and top surface 426. In the system 400 illustrated in FIGS. 23-30D, first fastener 410 may be orientated in various angles relative to second fastener 450. The specific angle configuration of first fastener 410 relative to second fastener 450 is locked into place set screw 412 within passageway head 430.

Similar to the prior embodiments, a drill guide may be used to pre-drill holes in the bone for both first fastener 410 and second fastener 450. Alternative constructions and configurations of a drill guide may also be used in accordance with the principles of the present invention.

In each of the embodiments described herein, first and second fasteners, drill guides and other components may include through holes to accommodate, for example, K-wires, drills and Jamshidi needles to assist with positioning and orientation during surgery. For example, first fastener 110 and second fastener 150 include through holes along their longitudinal axis to accommodate, for example, K-wires. In addition, alternative methods may be employed to install the various systems described herein. For example, a surgical robot or an image guidance system may be used to perform or aid in performing all or portions of the various steps required to properly install a system constructed in accordance with one or more aspects within a patient.

Although the fasteners shown and described through the present description, such as fasteners 110, 210, 310 and 410 and 150, 250, 350 and 450 are shown as being straight, it is also contemplated that one or more of these fasteners may have curved shafts that may be driven into the patient's vertebrae rather than screwed, or the shafts of these fasteners may also be slightly curved.

As may be recognized by those of ordinary skill in the art based on the teachings herein, numerous changes and modifications may be made to the above-described and other embodiments of the present invention without departing from the scope of the invention. The fasteners, elongate members, and other components of the devices and/or systems as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the devices and systems may include more or fewer components or features than the embodiments as described and illustrated herein. For example, the components and features of FIGS. 1-30D may all be used interchangeably and in alternative combinations as would be modified or altered by one of skill in the art. Accordingly, this detailed description of the currently-preferred embodiments is to be taken as illustrative, as opposed to limiting the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

The invention claimed is:

1. A bone fixation system, comprising:
  a first fastener comprising a threaded shaft for engaging bone tissue, the threaded shaft defining a cannula; and a head extending from a proximal portion of the threaded shaft, wherein the head is cylindrical, the head comprising:
an interior cavity defining:
a threaded passageway configured to receive a second fastener, wherein the threaded passageway is oriented oblique to a longitudinal axis of the first fastener, and wherein the threaded passageway comprises a seat configured to engage a portion of the head of the second fastener in a fixed relationship; and
wherein an exterior portion of the head couples to a first end of the threaded shaft, wherein the head has a longitudinal axis extending parallel with the threaded passageway, and wherein the longitudinal axis of the cylindrical head is oriented oblique to a longitudinal axis of the threaded shaft of the first fastener.

2. The bone fixation system of claim 1, wherein the seat comprises a surface configured to receive a portion of the head of the second fastener, and wherein the threaded passageway is sized and configured to couple to the second fastener.

3. The bone fixation system of claim 1, wherein the first fastener further comprises, a non-threaded tool engagement opening in communication with the cannula, wherein the non-threaded tool engagement opening is configured to receive a screwdriver tool.

4. The bone fixation system of claim 3, wherein the cannula is in communication with the threaded passageway via the non-threaded tool engagement opening.

5. The bone fixation system of claim 1, wherein the head comprises a proximal surface oriented obliquely to a non-threaded tool engagement opening.

6. The bone fixation system of claim 5, wherein the head comprises a circular opening through the proximal surface, and wherein the circular opening is offset to provide clearance to access the non-threaded tool engagement opening.

7. The bone fixation system of claim 5, wherein a proximal portion of the second fastener includes a tapering external surface that tapers radially, and wherein the tapering external surface contacts a portion of the seat of the first fastener when the second fastener is coupled to the first fastener.

8. The bone fixation system of claim 1, wherein a non-threaded tool engagement opening extends through a threaded surface of the threaded passageway.

9. The bone fixation system of claim 1, wherein the threaded passageway is configured to receive a threaded head of the second fastener.

10. The bone fixation system of claim 1, wherein the cannula of the threaded shaft of the first fastener is offset from the threaded passageway of the head of the first fastener, wherein the head further comprises:
a top surface; and
a bottom surface opposite the top surface,
wherein the top surface of the head is angled oblique to the longitudinal axis of the first fastener.

11. A bone fixation system, comprising:
a first bone fastener comprising a head and a threaded shaft, wherein an exterior surface of the head couples to a first end of the threaded shaft, wherein the head has a longitudinal axis and the longitudinal axis of the head is oriented oblique to a longitudinal axis of the threaded shaft of the first bone fastener; and
a second bone fastener, comprising:
a shaft defining a cannula; and
a head extending from a shaft, the head comprising an interior cavity defining:
a non-threaded tool engagement feature configured to receive a screwdriver tool, and
wherein the head of the second bone fastener is configured to be received within the head of the first bone fastener.

12. The bone fixation system of claim 11, wherein the head of the first bone fastener comprises an internal cavity having a threaded passageway oriented at an oblique angle relative to a longitudinal axis of the first bone fastener.

13. The bone fixation system of claim 11, wherein the head of the second bone fastener comprises an external surface, and wherein the external surface is threaded.

14. The bone fixation system of claim 13, wherein the threads of the head of the second bone fastener are sized to engage the threads of a threaded passageway of the first bone fastener when the second bone fastener is fixedly coupled to the first bone fastener.

15. The bone fixation system of claim 11, wherein the non-threaded tool engagement feature of the second bone fastener is configured to receive a hex screwdriver feature.

16. The bone fixation system of claim 11, wherein the shaft of the second bone fastener comprises a distal threaded portion and a proximal neck portion, wherein the proximal neck portion comprises a smooth external surface.

17. The bone fixation system of claim 16, wherein the proximal neck portion is integrally connected to a distal portion of the head.

18. The bone fixation system of claim 12, wherein when the second bone fastener is inserted into the threaded passageway of the first bone fastener, the second bone fastener is oriented at a fixed angle relative to the longitudinal axis of the first bone fastener.

19. The bone fixation system of claim 11, further comprising a drill guide tool for facilitating placement of the second bone fastener into bone tissue, wherein the drill guide tool comprises:
a threaded head configured to be threaded into a threaded passageway of the first bone fastener; and
a cannulated shaft configured to receive a drilling tool to form a hole in the bone tissue for the second bone fastener.

20. The bone fixation system of claim 11, wherein the first bone fastener further comprises a non-threaded tool engagement feature, wherein the non-threaded tool engagement feature extends through a threaded surface of a threaded passageway from the threaded passageway to an exterior surface of the head positioned between a first opening and a second opening of the threaded passageway.

* * * * *